United States Patent
Artymiuk et al.

(10) Patent No.: US 10,030,062 B2
(45) Date of Patent: Jul. 24, 2018

(54) GROWTH HORMONE FUSION PROTEINS WITH GROWTH HORMONE RECEPTOR AGONIST ACTIVITY

(71) Applicants: Peter Artymiuk, Sheffield (GB); Ian Wilkinson, Sheffield (GB); Richard Ross, Sheffield (GB)

(72) Inventors: Peter Artymiuk, Sheffield (GB); Ian Wilkinson, Sheffield (GB); Richard Ross, Sheffield (GB)

(73) Assignee: ASTERION LIMITED, Sheffield (GB)

( * ) Notice: Subject to any disclaimer, the term of this patent is extended or adjusted under 35 U.S.C. 154(b) by 0 days.

(21) Appl. No.: 15/283,404

(22) Filed: Oct. 2, 2016

(65) Prior Publication Data

US 2017/0015724 A1 Jan. 19, 2017

Related U.S. Application Data

(62) Division of application No. 14/004,684, filed as application No. PCT/GB2012/050550 on Mar. 14, 2012, now Pat. No. 9,493,536.

(30) Foreign Application Priority Data

Mar. 15, 2011 (GB) .................................. 1104285.0

(51) Int. Cl.
*A61K 38/27* (2006.01)
*C07K 14/61* (2006.01)
*C07K 14/72* (2006.01)
*C12N 5/10* (2006.01)
*C12N 15/63* (2006.01)
*C07K 14/71* (2006.01)
*A61K 38/00* (2006.01)

(52) U.S. Cl.
CPC ............. *C07K 14/61* (2013.01); *C07K 14/71* (2013.01); *C07K 14/72* (2013.01); *A61K 38/00* (2013.01); *C07K 2319/00* (2013.01); *C07K 2319/02* (2013.01); *C07K 2319/21* (2013.01)

(58) Field of Classification Search
None
See application file for complete search history.

(56) References Cited

U.S. PATENT DOCUMENTS

| 7,446,183 B2 | 11/2008 | Ross et al. |
| 7,524,649 B2 | 4/2009 | Ross |
| 8,273,552 B2 | 9/2012 | Artymiuk |
| 8,293,709 B2 | 10/2012 | Ross |
| 8,470,559 B2 | 6/2013 | Ross |

FOREIGN PATENT DOCUMENTS

| GB | 2389115 | 3/2003 |
| WO | 01/96565 | 12/2001 |
| WO | 2004/090135 | 10/2004 |
| WO | 2006/010891 | 1/2006 |
| WO | 2006/001770 | 2/2006 |
| WO | 2008/032059 | 3/2008 |
| WO | 2009/013461 | 1/2009 |

OTHER PUBLICATIONS

Walsh et al. Protein Science 12: 1960-1970, 2003.*
De Vos et al. Science 255: 306-312, 1992.
Clackson et al. J. Mol. Biol. 277: 1111-1128, 1998.
Schiffer et al. J. Mol. Biol. 316: 277-289, 2002.
Arman et al., "Novel Growth Hormone Receptor Gene Mutation in a Patient with Laron Syndrome," J. Ped End and Metab., 23: 407-414, 210.
Birzniece et al., "Growth hormone receptor modulators," Rev Endocr Metab Disord, 10:145-156, 2009.
Huo et al., "Computational alanine scanning of the 1:1 human growth hormone-receptor complex Antibodies Against a Peptide Sequence Within the HIV Envelope Protein Crossreacts with Human Interleukin-2," J. Comp. Chem., 23: 15-27, 2002.
Verkhivker et al., "Computational detection of the binding-site hot spot at the remodeled human growth hormone-receptor interface," Proteins, 53: 201/219, 2003.
Wilkinson et al., "A ligand-receptor fusion of growth hormone forms a dimer and is a potent long-acting agonist," Nat Med, 13:1108-1113, 2007.
Yang et al., "Activation of growth hormone receptors by growth hormone and growth hormone antagonist dimers: Insights into receptor triggering," Mol Endocrin, 22: 978-988, 2008.

* cited by examiner

*Primary Examiner* — Christine J Saoud
(74) *Attorney, Agent, or Firm* — JMB Davis Ben-David

(57) ABSTRACT

We disclose growth hormone fusion proteins that have increased in vivo stability and activity; nucleic acid molecules encoding said proteins and methods of treatment of growth hormone related diseases that would benefit from growth hormone agonists or antagonists.

16 Claims, 19 Drawing Sheets

FIGURE 1A – AMINO ACID SEQUENCE OF HUMAN GHR EXTRACELLULAR DOMAIN

MDLWQLLLTLALAGSSDA
FSGSEATAAILSRAPWSLQSVNPGLKTNSSKEPKFTKCRSPERETFSCHWTDEVHHGTK
NLGPIQLFYTRRNTQEWTQEWKECPDYVSAGENSCYFNSSFTSIWIPYCIKLTSNGGTV
DEKCFSVDEIVQPDPPIALNWTLLNVSLTGIHADIQVRWEAPRNADIQKGWMVLEYELQ
YKEVNETKWKMMDPILTTSVPVYSLKVDKEYEVRVRSKQRNSGNYGEFSEVLYVTLPQM
SQ

FIGURE 1B – AMINO ACID SEQUENCE OF HUMAN GHR EXTRACELLULAR DOMAIN – W104A MUTATION.

MDLWQLLLTLALAGSSDA
FSGSEATAAILSRAPWSLQSVNPGLKTNSSKEPKFTKCRSPERETFSCHWTDEVHHGTK
NLGPIQLFYTRRNTQEWTQEWKECPDYVSAGENSCYFNSSFTSIAIPYCIKLTSNGGTV
DEKCFSVDEIVQPDPPIALNWTLLNVSLTGIHADIQVRWEAPRNADIQKGWMVLEYELQ
YKEVNETKWKMMDPILTTSVPVYSLKVDKEYEVRVRSKQRNSGNYGEFSEVLYVTLPQM
SQ

Figure 2 human growth hormone

MATGSRTSLLLAFGLLCLPWLQEGSA
FPTIPLSRLFDNAMLRAHRLHQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
EGIQTLMGRLEDGSPRTGQIFKQTYSKFDTNSHNDDALLKNYGLLYCFRKDMDKVETFL
RIVQCRSVEGSCGF

Figure 3 1B7-V1 matgsrtslllafgllclpwlqegsa
FPTIPLSRLFDNAMLRAHRLHQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
EGIQTLMGRLEDGSPRTGQIFKQTYSKFDTNSHNDDALLKNYGLLYCFRKDMDKVETFL
RIVQCRSVEGSCGFGGRGGGGSGGGGSGGGGSGGGGSEFFSGSEATAAILSRAPWSLQS
VNPGLKTNSSKEPKFTKCRSPERETFSCHWTDEVHHGTKNLGPIQLFYTRRNTQEWTQE
WKECPDYVSAGENSCYFNSSFTSIWIPYCIKLTSNGGTVDEKCFSVDEIVQPDPPIALN
WTLLNVSLTGIHADIQVRWEAPRNADIQKGWMVLEYELQYKEVNETKWKMMDPILTTSV
PVYSLKVDKEYEVRVRSKQRNSGNYGEFSEVLYVTLPQMSQ

Figure 4 1B7-V2 matgsrtslllafgllclpwlqegsa
FPTIPLSRLFDNAMLRAHRLHQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
EGIQTLMGRLEDGSPRTGQIFKQTYSKFDTNSHNDDALLKNYGLLYCFRKDMDKVETFL
RIVQCRSVEGSCGFGGGGSGGGGSGGGGSGGGGSGGGGSFSGSEATAAILSRAPWSLQS
VNPGLKTNSSKEPKFTKCRSPERETFSCHWTDEVHHGTKNLGPIQLFYTRRNTQEWTQE
WKECPDYVSAGENSCYFNSSFTSIWIPYCIKLTSNGGTVDEKCFSVDEIVQPDPPIALN
WTLLNVSLTGIHADIQVRWEAPRNADIQKGWMVLEYELQYKEVNETKWKMMDPILTTSV
PVYSLKVDKEYEVRVRSKQRNSGNYGEFSEVLYVTLPQMSQ

Figure 5 1B7-V3 matgsrtslllafgllclpwlqegsa
FPTIPLSRLFDNAMLRAHRLHQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
EGIQTLMGRLEDGSPRTGQIFKQTYSKFDTNSHNDDALLKNYGLLYCFRKDMDKVETFL
RIVQCRSVEGSCGFFSGSEATAAILSRAPWSLQSVNPGLKTNSSKEPKFTKCRSPERET
FSCHWTDEVHHGTKNLGPIQLFYTRRNTQEWTQEWKECPDYVSAGENSCYFNSSFTSIW
IPYCIKLTSNGGTVDEKCFSVDEIVQPDPPIALNWTLLNVSLTGIHADIQVRWEAPRNA
DIQKGWMVLEYELQYKEVNETKWKMMDPILTTSVPVYSLKVDKEYEVRVRSKQRNSGNY
GEFSEVLYVTLPQMSQ

Figure 6 1B8v1

MATGSRTSLLLAFGLLCLPWLQEGSA
FPTIPLSRLFDNAMLRAHRLHQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
ERIQTLMGRLEDGSPRTGQIFKQTYSKFDTNSHNDDALLKNYGLLYCFRKDMDKVETFL
RIVQCRSVEGSCGFGGRGGGGSGGGGSGGGGSGGGGSEFFSGSEATAAILSRAPWSLQS
VNPGLKTNSSKEPKFTKCRSPERETFSCHWTDEVHHGTKNLGPIQLFYTRRNTQEWTQE
WKECPDYVSAGENSCYFNSSFTSIWIPYCIKLTSNGGTVDEKCFSVDEIVQPDPPIALN
WTLLNVSLTGIHADIQVRWEAPRNADIQKGWMVLEYELQYKEVNETKWKMMDPILTTSV
PVYSLKVDKEYEVRVRSKQRNSGNYGEFSEVLYVTLPQMSQ*

Figure 7 1B8v2

MATGSRTSLLLAFGLLCLPWLQEGSA
FPTIPLSRLFDNAMLRAHRLHQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
ERIQTLMGRLEDGSPRTGQIFKQTYSKFDTNSHNDDALLKNYGLLYCFRKDMDKVETFL
RIVQCRSVEGSCGFGGGGSGGGGSGGGGSGGGGSGGGGSFSGSEATAAILSRAPWSLQS
VNPGLKTNSSKEPKFTKCRSPERETFSCHWTDEVHHGTKNLGPIQLFYTRRNTQEWTQE
WKECPDYVSAGENSCYFNSSFTSIWIPYCIKLTSNGGTVDEKCFSVDEIVQPDPPIALN
WTLLNVSLTGIHADIQVRWEAPRNADIQKGWMVLEYELQYKEVNETKWKMMDPILTTSV
PVYSLKVDKEYEVRVRSKQRNSGNYGEFSEVLYVTLPQMSQ*

Figure 8 1B8v3

MATGSRTSLLLAFGLLCLPWLQEGSA
FPTIPLSRLFDNAMLRAHRLHQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
ERIQTLMGRLEDGSPRTGQIFKQTYSKFDTNSHNDDALLKNYGLLYCFRKDMDKVETFL
RIVQCRSVEGSCGFFSGSEATAAILSRAPWSLQSVNPGLKTNSSKEPKFTKCRSPERET
FSCHWTDEVHHGTKNLGPIQLFYTRRNTQEWTQEWKECPDYVSAGENSCYFNSSFTSIW
IPYCIKLTSNGGTVDEKCFSVDEIVQPDPPIALNWTLLNVSLTGIHADIQVRWEAPRNA
DIQKGWMVLEYELQYKEVNETKWKMMDPILTTSVPVYSLKVDKEYEVRVRSKQRNSGNY
GEFSEVLYVTLPQMSQ*

Figure 9 1B9v1

MATGSRTSLLLAFGLLCLPWLQEGSA
FPTIPLSRLFDNAMLRADRLNQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
ERIQTLMGRLEDGSPRTGQIFKQTYSKFDTNSHNDDALLKNYGLLYCFNADMSRVSTFL
RTVQCRSVEGSCGF<u>GGR</u>GGGGSGGGGSGGGGSGGGGS<u>EFF</u>SGSEATAAILSRAPWSLQS
VNPGLKTNSSKEPKFTKCRSPERETFSCHWTDEVHHGTKNLGPIQLFYTRRNTQEWTQE
WKECPDYVSAGENSCYFNSSFTSIWIPYCIKLTSNGGTVDEKCFSVDEIVQPDPPIALN
WTLLNVSLTGIHADIQVRWEAPRNADIQKGWMVLEYELQYKEVNETKWKMMDPILTTSV
PVYSLKVDKEYEVRVRSKQRNSGNYGEFSEVLYVTLPQMSQ*

Figure 10 1B9v2

MATGSRTSLLLAFGLLCLPWLQEGSA
FPTIPLSRLFDNAMLRADRLNQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
ERIQTLMGRLEDGSPRTGQIFKQTYSKFDTNSHNDDALLKNYGLLYCFNADMSRVSTFL
RTVQCRSVEGSCGFGGGGSGGGGSGGGGSGGGGSGGGGSFSGSEATAAILSRAPWSLQS
VNPGLKTNSSKEPKFTKCRSPERETFSCHWTDEVHHGTKNLGPIQLFYTRRNTQEWTQE
WKECPDYVSAGENSCYFNSSFTSIWIPYCIKLTSNGGTVDEKCFSVDEIVQPDPPIALN
WTLLNVSLTGIHADIQVRWEAPRNADIQKGWMVLEYELQYKEVNETKWKMMDPILTTSV
PVYSLKVDKEYEVRVRSKQRNSGNYGEFSEVLYVTLPQMSQ

Figure 11 1B9v3

MATGSRTSLLLAFGLLCLPWLQEGSA
FPTIPLSRLFDNAMLRADRLNQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
ERIQTLMGRLEDGSPRTGQIFKQTYSKFDTNSHNDDALLKNYGLLYCFNADMSRVSTFL
RTVQCRSVEGSCGFFSGSEATAAILSRAPWSLQSVNPGLKTNSSKEPKFTKCRSPERET
FSCHWTDEVHHGTKNLGPIQLFYTRRNTQEWTQEWKECPDYVSAGENSCYFNSSFTSIW
IPYCIKLTSNGGTVDEKCFSVDEIVQPDPPIALNWTLLNVSLTGIHADIQVRWEAPRNA
DIQKGWMVLEYELQYKEVNETKWKMMDPILTTSVPVYSLKVDKEYEVRVRSKQRNSGNY
GEFSEVLYVTLPQMSQ

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEEGIQTLMGRLEDGSPRTGQIFKQTYSKFDTNSHNDDALLKNYGLLYCFRKDMD
KVETFLRIVQCRSVEGSCGFGGRGGGGSGGGGSGGnGSGGGGSEFFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEEGIQTLMGRLEDGSPRTGQIFKQTYSKFDTNSHNDDALLKNYGLLYCFRKDMD
KVETFLRIVQCRSVEGSCGFGGGGSGGGGSGGnGSGGGGSGGGGSFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEEGIQTLMGRLEDGSPRTGQIFKQTYSKFDTNSHNDDALLKNYGLLYCFRKDMD
KVETFLRIVQCRSVEGSCGFGGRGGGGSGGGGSGGnGtGGGGSEFFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEEGIQTLMGRLEDGSPRTGQIFKQTYSKFDTNSHNDDALLKNYGLLYCFRKDMD
KVETFLRIVQCRSVEGSCGFGGGGSGGGGSGGnGt GGGGSGGGGSFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEEGIQTLMGRLEDGSPRTGQIFKQTYSKFDTNSHNDDALLKNYGLLYCFRKDMD
KVETFLRIVQCRSVEGSCGFGGRGGGGSGGGGSGwnGSGGGGSEFFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEEGIQTLMGRLEDGSPRTGQIFKQTYSKFDTNSHNDDALLKNYGLLYCFRKDMD
KVETFLRIVQCRSVEGSCGFGGGGSGGGGSGwnGSGGGGSGGGGSFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEEGIQTLMGRLEDGSPRTGQIFKQTYSKFDTNSHNDDALLKNYGLLYCFRKDMD
KVETFLRIVQCRSVEGSCGFGGRGGGGSGGGGSGGGGSnatGGGGSEFFSGSEATAA
ILSRAPWSLQSVNPGLKTNSSKEPKFTKCRSPERETFSCHWTDEVHHGTKNLGPIQL
FYTRRNTQEWTQEWKECPDYVSAGENSCYFNSSFTSIWIPYCIKLTSNGGTVDEKCF
SVDEIVQPDPPIALNWTLLNVSLTGIHADIQVRWEAPRNADIQKGWMVLEYELQYKE
VNETKWKMMDPILTTSVPVYSLKVDKEYEVRVRSKQRNSGNYGEFSEVLYVTLPQMS
Q*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEEGIQTLMGRLEDGSPRTGQIFKQTYSKFDTNSHNDDALLKNYGLLYCFRKDMD
KVETFLRIVQCRSVEGSCGFGGGGSGGGGSGGGGSnatGGGGSGGGGSFSGSEATAA
ILSRAPWSLQSVNPGLKTNSSKEPKFTKCRSPERETFSCHWTDEVHHGTKNLGPIQL
FYTRRNTQEWTQEWKECPDYVSAGENSCYFNSSFTSIWIPYCIKLTSNGGTVDEKCF
SVDEIVQPDPPIALNWTLLNVSLTGIHADIQVRWEAPRNADIQKGWMVLEYELQYKE
VNETKWKMMDPILTTSVPVYSLKVDKEYEVRVRSKQRNSGNYGEFSEVLYVTLPQMS
Q*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGF<u>GGR</u>GGGGSGGGGSGG<u>n</u>GGGGS<u>EF</u>FSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGFGGGGSGGGGSGGnGSGGGGSGGGGSFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGF<u>GGR</u>GGGGSGGGGSGG<u>n</u>GSGGGGS<u>EF</u>FSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGFGGGGSGGGGSGGnGSGGGGSGGGGSFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGFGGRGGGGSGGGGSGwnGSGGGGSEFFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGFGGGGSGGGGSGwnGSGGGGSGGGGSFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGFGGRGGGGSGGGGSGwnGSGGGGSEFFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGFGGGGSGGGGSGwnGSGGGGSGGGGSFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGFGGRGGGGSGGGGSGGGGSnatGGGGSEFFSGSEATAA
ILSRAPWSLQSVNPGLKTNSSKEPKFTKCRSPERETFSCHWTDEVHHGTKNLGPIQL
FYTRRNTQEWTQEWKECPDYVSAGENSCYFNSSFTSIWIPYCIKLTSNGGTVDEKCF
SVDEIVQPDPPIALNWTLLNVSLTGIHADIQVRWEAPRNADIQKGWMVLEYELQYKE
VNETKWKMMDPILTTSVPVYSLKVDKEYEVRVRSKQRNSGNYGEFSEVLYVTLPQMS
Q*

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGFGGGGSGGGGSGGGGSnatGGGGSGGGGSFSGSEATAA
ILSRAPWSLQSVNPGLKTNSSKEPKFTKCRSPERETFSCHWTDEVHHGTKNLGPIQL
FYTRRNTQEWTQEWKECPDYVSAGENSCYFNSSFTSIWIPYCIKLTSNGGTVDEKCF
SVDEIVQPDPPIALNWTLLNVSLTGIHADIQVRWEAPRNADIQKGWMVLEYELQYKE
VNETKWKMMDPILTTSVPVYSLKVDKEYEVRVRSKQRNSGNYGEFSEVLYVTLPQMS
Q

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGFGG̲R̲GGGGSGGGGSGGGGSnatGGGGSE̲F̲FSGSEATAA
ILSRAPWSLQSVNPGLKTNSSKEPKFTKCRSPERETFSCHWTDEVHHGTKNLGPIQL
FYTRRNTQEWTQEWKECPDYVSAGENSCYFNSSFTSIWIPYCIKLTSNGGTVDEKCF
SVDEIVQPDPPIALNWTLLNVSLTGIHADIQVRWEAPRNADIQKGWMVLEYELQYKE
VNETKWKMMDPILTTSVPVYSLKVDKEYEVRVRSKQRNSGNYGEFSEVLYVTLPQMS
Q

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGFGGGGSGGGGSGGGGSnatGGGGSGGGGSFSGSEATAA
ILSRAPWSLQSVNPGLKTNSSKEPKFTKCRSPERETFSCHWTDEVHHGTKNLGPIQL
FYTRRNTQEWTQEWKECPDYVSAGENSCYFNSSFTSIWIPYCIKLTSNGGTVDEKCF
SVDEIVQPDPPIALNWTLLNVSLTGIHADIQVRWEAPRNADIQKGWMVLEYELQYKE
VNETKWKMMDPILTTSVPVYSLKVDKEYEVRVRSKQRNSGNYGEFSEVLYVTLPQMS
Q

SEQUENCE LISTING

```
<160> NUMBER OF SEQ ID NOS: 73

<210> SEQ ID NO 1
<211> LENGTH: 256
<212> TYPE: PRT
<213> ORGANISM: Homo sapiens

<400> SEQUENCE: 1

Met Asp Leu Trp Gln Leu Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
                20                  25                  30

Pro Trp Ser Leu Gln Ser Val Asn Pro Gly Leu Lys Thr Asn Ser Ser
            35                  40                  45

Lys Glu Pro Lys Phe Thr Lys Cys Arg Ser Pro Glu Arg Glu Thr Phe
50                  55                  60

Ser Cys His Trp Thr Asp Glu Val His His Gly Thr Lys Asn Leu Gly
65                  70                  75                  80

Pro Ile Gln Leu Phe Tyr Thr Arg Arg Asn Thr Gln Glu Trp Thr Gln
                85                  90                  95

Glu Trp Lys Glu Cys Pro Asp Tyr Val Ser Ala Gly Glu Asn Ser Cys
            100                 105                 110

Tyr Phe Asn Ser Ser Phe Thr Ser Ile Trp Ile Pro Tyr Cys Ile Lys
        115                 120                 125

Leu Thr Ser Asn Gly Gly Thr Val Asp Glu Lys Cys Phe Ser Val Asp
    130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
                165                 170                 175

Ala Pro Arg Asn Ala Asp Ile Gln Lys Gly Trp Met Val Leu Glu Tyr
            180                 185                 190

Glu Leu Gln Tyr Lys Glu Val Asn Glu Thr Lys Trp Lys Met Met Asp
        195                 200                 205

Pro Ile Leu Thr Thr Ser Val Pro Val Tyr Ser Leu Lys Val Asp Lys
    210                 215                 220

Glu Tyr Glu Val Arg Val Arg Ser Lys Gln Arg Asn Ser Gly Asn Tyr
225                 230                 235                 240

Gly Glu Phe Ser Glu Val Leu Tyr Val Thr Leu Pro Gln Met Ser Gln
                245                 250                 255

<210> SEQ ID NO 2
<211> LENGTH: 256
<212> TYPE: PRT
<213> ORGANISM: artificial sequence
<220> FEATURE:
<223> OTHER INFORMATION: modified human GHR domain
```

<400> SEQUENCE: 2

Met Asp Leu Trp Gln Leu Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
            20                  25                  30

Pro Trp Ser Leu Gln Ser Val Asn Pro Gly Leu Lys Thr Asn Ser Ser
            35                  40                  45

Lys Glu Pro Lys Phe Thr Lys Cys Arg Ser Pro Glu Arg Glu Thr Phe
    50                  55                  60

Ser Cys His Trp Thr Asp Glu Val His Gly Thr Lys Asn Leu Gly
65                  70                  75                  80

Pro Ile Gln Leu Phe Tyr Thr Arg Arg Asn Thr Gln Glu Trp Thr Gln
                85                  90                  95

Glu Trp Lys Glu Cys Pro Asp Tyr Val Ser Ala Gly Glu Asn Ser Cys
            100                 105                 110

Tyr Phe Asn Ser Ser Phe Thr Ser Ile Ala Ile Pro Tyr Cys Ile Lys
        115                 120                 125

Leu Thr Ser Asn Gly Gly Thr Val Asp Glu Lys Cys Phe Ser Val Asp
    130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
                165                 170                 175

Ala Pro Arg Asn Ala Asp Ile Gln Lys Gly Trp Met Val Leu Glu Tyr
            180                 185                 190

Glu Leu Gln Tyr Lys Glu Val Asn Glu Thr Lys Trp Lys Met Met Asp
        195                 200                 205

Pro Ile Leu Thr Thr Ser Val Pro Val Tyr Ser Leu Lys Val Asp Lys
    210                 215                 220

Glu Tyr Glu Val Arg Val Arg Ser Lys Gln Arg Asn Ser Gly Asn Tyr
225                 230                 235                 240

Gly Glu Phe Ser Glu Val Leu Tyr Val Thr Leu Pro Gln Met Ser Gln
                245                 250                 255

<210> SEQ ID NO 3
<211> LENGTH: 217
<212> TYPE: PRT
<213> ORGANISM: artificial sequence
<220> FEATURE:
<223> OTHER INFORMATION: human growth hormone

<400> SEQUENCE: 3

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp

```
                100                 105                 110
Leu Glu Pro Val Gln Phe Leu Arg Ser Val Phe Ala Asn Ser Leu Val
            115                 120                 125
Tyr Gly Ala Ser Asp Ser Asn Val Tyr Asp Leu Leu Lys Asp Leu Glu
        130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
        195                 200                 205
Arg Ser Val Glu Gly Ser Cys Gly Phe
    210                 215
```

<210> SEQ ID NO 4
<211> LENGTH: 480
<212> TYPE: PRT
<213> ORGANISM: artificial sequence
<220> FEATURE:
<223> OTHER INFORMATION: Growth hormone fusion

<400> SEQUENCE: 4

```
Met Ala Thr Gly Ser Arg Thr Ser Leu Leu Leu Ala Phe Gly Leu Leu
1               5                   10                  15
Cys Leu Pro Trp Leu Gln Glu Gly Ser Ala Phe Pro Thr Ile Pro Leu
            20                  25                  30
Ser Arg Leu Phe Asp Asn Ala Met Leu Arg Ala His Arg Leu His Gln
        35                  40                  45
Leu Ala Phe Asp Thr Tyr Gln Glu Phe Glu Glu Ala Tyr Ile Pro Lys
    50                  55                  60
Glu Gln Lys Tyr Ser Phe Leu Gln Asn Pro Gln Thr Ser Leu Cys Phe
65                  70                  75                  80
Ser Glu Ser Ile Pro Thr Pro Ser Asn Arg Glu Glu Thr Gln Gln Lys
                85                  90                  95
Ser Asn Leu Glu Leu Leu Arg Ile Ser Leu Leu Leu Ile Gln Ser Trp
            100                 105                 110
Leu Glu Pro Val Gln Phe Leu Arg Ser Val Phe Ala Asn Ser Leu Val
        115                 120                 125
Tyr Gly Ala Ser Asp Ser Asn Val Tyr Asp Leu Leu Lys Asp Leu Glu
    130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
        195                 200                 205
Arg Ser Val Glu Gly Ser Cys Gly Phe Gly Gly Arg Gly Gly Gly Gly
    210                 215                 220
Ser Gly Gly Gly Gly Ser Gly Gly Gly Gly Ser Gly Gly Gly Gly Ser
225                 230                 235                 240
Glu Phe Phe Ser Gly Ser Glu Ala Thr Ala Ala Ile Leu Ser Arg Ala
```

```
                245                 250                 255
Pro Trp Ser Leu Gln Ser Val Asn Pro Gly Leu Lys Thr Asn Ser Ser
                260                 265                 270

Lys Glu Pro Lys Phe Thr Lys Cys Arg Ser Pro Glu Arg Glu Thr Phe
            275                 280                 285

Ser Cys His Trp Thr Asp Glu Val His His Gly Thr Lys Asn Leu Gly
        290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
        355                 360                 365

Glu Ile Val Gln Pro Asp Pro Pro Ile Ala Leu Asn Trp Thr Leu Leu
370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
        435                 440                 445

Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480

<210> SEQ ID NO 5
<211> LENGTH: 480
<212> TYPE: PRT
<213> ORGANISM: artificial sequence
<220> FEATURE:
<223> OTHER INFORMATION: Growth hormone fusion

<400> SEQUENCE: 5

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
```

```
                130                 135                 140
Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Gly Ser Gly Gly Gly
    210                 215                 220

Gly Gly Ser Gly Gly Gly Ser Gly Gly Gly Ser Gly Gly Gly
225                 230                 235                 240

Gly Ser Phe Ser Gly Ser Glu Ala Thr Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
    290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
        355                 360                 365

Glu Ile Val Gln Pro Asp Pro Pro Ile Ala Leu Asn Trp Thr Leu Leu
    370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
        435                 440                 445

Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480

<210> SEQ ID NO 6
<211> LENGTH: 455
<212> TYPE: PRT
<213> ORGANISM: artificial sequence
<220> FEATURE:
<223> OTHER INFORMATION: Growth hormone fusion

<400> SEQUENCE: 6

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
```

```
            20                  25                  30
Ser Arg Leu Phe Asp Asn Ala Met Leu Arg Ala His Arg Leu His Gln
             35                  40                  45

Leu Ala Phe Asp Thr Tyr Gln Glu Phe Glu Glu Ala Tyr Ile Pro Lys
 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
             100                 105                 110

Leu Glu Pro Val Gln Phe Leu Arg Ser Val Phe Ala Asn Ser Leu Val
             115                 120                 125

Tyr Gly Ala Ser Asp Ser Asn Val Tyr Asp Leu Leu Lys Asp Leu Glu
         130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                 165                 170                 175

His Asn Asp Asp Ala Leu Leu Lys Asn Tyr Gly Leu Leu Tyr Cys Phe
             180                 185                 190

Arg Lys Asp Met Asp Lys Val Glu Thr Phe Leu Arg Ile Val Gln Cys
             195                 200                 205

Arg Ser Val Glu Gly Ser Cys Gly Phe Phe Ser Gly Ser Glu Ala Thr
         210                 215                 220

Ala Ala Ile Leu Ser Arg Ala Pro Trp Ser Leu Gln Ser Val Asn Pro
225                 230                 235                 240

Gly Leu Lys Thr Asn Ser Ser Lys Glu Pro Lys Phe Thr Lys Cys Arg
                 245                 250                 255

Ser Pro Glu Arg Glu Thr Phe Ser Cys His Trp Thr Asp Glu Val His
             260                 265                 270

His Gly Thr Lys Asn Leu Gly Pro Ile Gln Leu Phe Tyr Thr Arg Arg
         275                 280                 285

Asn Thr Gln Glu Trp Thr Gln Glu Trp Lys Glu Cys Pro Asp Tyr Val
         290                 295                 300

Ser Ala Gly Glu Asn Ser Cys Tyr Phe Asn Ser Ser Phe Thr Ser Ile
305                 310                 315                 320

Trp Ile Pro Tyr Cys Ile Lys Leu Thr Ser Asn Gly Gly Thr Val Asp
                 325                 330                 335

Glu Lys Cys Phe Ser Val Asp Glu Ile Val Gln Pro Asp Pro Pro Ile
             340                 345                 350

Ala Leu Asn Trp Thr Leu Leu Asn Val Ser Leu Thr Gly Ile His Ala
         355                 360                 365

Asp Ile Gln Val Arg Trp Glu Ala Pro Arg Asn Ala Asp Ile Gln Lys
     370                 375                 380

Gly Trp Met Val Leu Glu Tyr Glu Leu Gln Tyr Lys Glu Val Asn Glu
385                 390                 395                 400

Thr Lys Trp Lys Met Met Asp Pro Ile Leu Thr Thr Ser Val Pro Val
                 405                 410                 415

Tyr Ser Leu Lys Val Asp Lys Glu Tyr Glu Val Arg Val Arg Ser Lys
             420                 425                 430

Gln Arg Asn Ser Gly Asn Tyr Gly Glu Phe Ser Glu Val Leu Tyr Val
         435                 440                 445
```

```
Thr Leu Pro Gln Met Ser Gln
    450             455

<210> SEQ ID NO 7
<211> LENGTH: 480
<212> TYPE: PRT
<213> ORGANISM: artificial sequence
<220> FEATURE:
<223> OTHER INFORMATION: Growth hormone fusion

<400> SEQUENCE: 7

Met Ala Thr Gly Ser Arg Thr Ser Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Arg Gly Gly Gly Gly
    210                 215                 220

Ser Gly Gly Gly Gly Ser Gly Gly Gly Gly Ser Gly Gly Gly Gly Ser
225                 230                 235                 240

Glu Phe Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
    290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350
```

```
Leu Thr Ser Asn Gly Gly Thr Val Asp Glu Lys Cys Phe Ser Val Asp
        355                 360                 365

Glu Ile Val Gln Pro Asp Pro Ile Ala Leu Asn Trp Thr Leu Leu
    370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
        435                 440                 445

Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480

<210> SEQ ID NO 8
<211> LENGTH: 480
<212> TYPE: PRT
<213> ORGANISM: artificial sequence
<220> FEATURE:
<223> OTHER INFORMATION: Growth hormone fusion

<400> SEQUENCE: 8

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Gly Ser Gly Gly
    210                 215                 220

Gly Gly Ser Gly Gly Gly Gly Ser Gly Gly Gly Ser Gly Gly Gly
225                 230                 235                 240
```

```
Gly Ser Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
    290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
        355                 360                 365

Glu Ile Val Gln Pro Asp Pro Pro Ile Ala Leu Asn Trp Thr Leu Leu
    370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
        435                 440                 445

Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480

<210> SEQ ID NO 9
<211> LENGTH: 455
<212> TYPE: PRT
<213> ORGANISM: artificial sequence
<220> FEATURE:
<223> OTHER INFORMATION: Growth hormone fusion

<400> SEQUENCE: 9

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125
```

Tyr Gly Ala Ser Asp Ser Asn Val Tyr Asp Leu Leu Lys Asp Leu Glu
            130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Ser Gly Ser Glu Ala Thr
210                 215                 220

Ala Ala Ile Leu Ser Arg Ala Pro Trp Ser Leu Gln Ser Val Asn Pro
225                 230                 235                 240

Gly Leu Lys Thr Asn Ser Ser Lys Glu Pro Lys Phe Thr Lys Cys Arg
                245                 250                 255

Ser Pro Glu Arg Glu Thr Phe Ser Cys His Trp Thr Asp Glu Val His
            260                 265                 270

His Gly Thr Lys Asn Leu Gly Pro Ile Gln Leu Phe Tyr Thr Arg Arg
        275                 280                 285

Asn Thr Gln Glu Trp Thr Gln Glu Trp Lys Glu Cys Pro Asp Tyr Val
290                 295                 300

Ser Ala Gly Glu Asn Ser Cys Tyr Phe Asn Ser Ser Phe Thr Ser Ile
305                 310                 315                 320

Trp Ile Pro Tyr Cys Ile Lys Leu Thr Ser Asn Gly Gly Thr Val Asp
                325                 330                 335

Glu Lys Cys Phe Ser Val Asp Glu Ile Val Gln Pro Asp Pro Pro Ile
            340                 345                 350

Ala Leu Asn Trp Thr Leu Leu Asn Val Ser Leu Thr Gly Ile His Ala
        355                 360                 365

Asp Ile Gln Val Arg Trp Glu Ala Pro Arg Asn Ala Asp Ile Gln Lys
370                 375                 380

Gly Trp Met Val Leu Glu Tyr Glu Leu Gln Tyr Lys Glu Val Asn Glu
385                 390                 395                 400

Thr Lys Trp Lys Met Met Asp Pro Ile Leu Thr Thr Ser Val Pro Val
                405                 410                 415

Tyr Ser Leu Lys Val Asp Lys Glu Tyr Glu Val Arg Val Arg Ser Lys
            420                 425                 430

Gln Arg Asn Ser Gly Asn Tyr Gly Glu Phe Ser Glu Val Leu Tyr Val
        435                 440                 445

Thr Leu Pro Gln Met Ser Gln
    450                 455

<210> SEQ ID NO 10
<211> LENGTH: 480
<212> TYPE: PRT
<213> ORGANISM: artificial sequence
<220> FEATURE:
<223> OTHER INFORMATION: Growth hormone fusion

<400> SEQUENCE: 10

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

```
Ser Arg Leu Phe Asp Asn Ala Met Leu Arg Ala Asp Arg Leu Asn Gln
        35                  40                  45
Leu Ala Phe Asp Thr Tyr Gln Glu Phe Glu Glu Ala Tyr Ile Pro Lys
        50                  55                  60
Glu Gln Lys Tyr Ser Phe Leu Gln Asn Pro Gln Thr Ser Leu Cys Phe
65                  70                  75                  80
Ser Glu Ser Ile Pro Thr Pro Ser Asn Arg Glu Glu Thr Gln Gln Lys
                    85                  90                  95
Ser Asn Leu Glu Leu Leu Arg Ile Ser Leu Leu Leu Ile Gln Ser Trp
                100                 105                 110
Leu Glu Pro Val Gln Phe Leu Arg Ser Val Phe Ala Asn Ser Leu Val
                115                 120                 125
Tyr Gly Ala Ser Asp Ser Asn Val Tyr Asp Leu Leu Lys Asp Leu Glu
            130                 135                 140
Glu Arg Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Asn Ala Asp Met Ser Arg Val Ser Thr Phe Leu Arg Thr Val Gln Cys
            195                 200                 205
Arg Ser Val Glu Gly Ser Cys Gly Phe Gly Gly Arg Gly Gly Gly Gly
        210                 215                 220
Ser Gly Gly Gly Gly Ser Gly Gly Gly Gly Ser Gly Gly Gly Gly Ser
225                 230                 235                 240
Glu Phe Phe Ser Gly Ser Glu Ala Thr Ala Ala Ile Leu Ser Arg Ala
                245                 250                 255
Pro Trp Ser Leu Gln Ser Val Asn Pro Gly Leu Lys Thr Asn Ser Ser
            260                 265                 270
Lys Glu Pro Lys Phe Thr Lys Cys Arg Ser Pro Glu Arg Glu Thr Phe
        275                 280                 285
Ser Cys His Trp Thr Asp Glu Val His His Gly Thr Lys Asn Leu Gly
        290                 295                 300
Pro Ile Gln Leu Phe Tyr Thr Arg Arg Asn Thr Gln Glu Trp Thr Gln
305                 310                 315                 320
Glu Trp Lys Glu Cys Pro Asp Tyr Val Ser Ala Gly Glu Asn Ser Cys
                325                 330                 335
Tyr Phe Asn Ser Ser Phe Thr Ser Ile Trp Ile Pro Tyr Cys Ile Lys
            340                 345                 350
Leu Thr Ser Asn Gly Gly Thr Val Asp Glu Lys Cys Phe Ser Val Asp
            355                 360                 365
Glu Ile Val Gln Pro Asp Pro Pro Ile Ala Leu Asn Trp Thr Leu Leu
        370                 375                 380
Asn Val Ser Leu Thr Gly Ile His Ala Asp Ile Gln Val Arg Trp Glu
385                 390                 395                 400
Ala Pro Arg Asn Ala Asp Ile Gln Lys Gly Trp Met Val Leu Glu Tyr
                405                 410                 415
Glu Leu Gln Tyr Lys Glu Val Asn Glu Thr Lys Trp Lys Met Met Asp
            420                 425                 430
Pro Ile Leu Thr Thr Ser Val Pro Val Tyr Ser Leu Lys Val Asp Lys
            435                 440                 445
```

```
Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480

<210> SEQ ID NO 11
<211> LENGTH: 480
<212> TYPE: PRT
<213> ORGANISM: artificial sequence
<220> FEATURE:
<223> OTHER INFORMATION: Growth hormone fusion

<400> SEQUENCE: 11

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala Asp Arg Leu Asn Gln
            35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
    115                 120                 125

Tyr Gly Ala Ser Asp Ser Asn Val Tyr Asp Leu Leu Lys Asp Leu Glu
130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Asn Ala Asp Met Ser Arg Val Ser Thr Phe Leu Arg Thr Val Gln Cys
    195                 200                 205

Arg Ser Val Glu Gly Ser Cys Gly Phe Gly Gly Gly Ser Gly Gly
210                 215                 220

Gly Gly Ser Gly Gly Gly Ser Gly Gly Gly Ser Gly Gly Gly Gly
225                 230                 235                 240

Gly Ser Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
    275                 280                 285

Ser Cys His Trp Thr Asp Glu Val His His Gly Thr Lys Asn Leu Gly
290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335
```

```
Tyr Phe Asn Ser Ser Phe Thr Ser Ile Trp Ile Pro Tyr Cys Ile Lys
                340                 345                 350

Leu Thr Ser Asn Gly Gly Thr Val Asp Glu Lys Cys Phe Ser Val Asp
            355                 360                 365

Glu Ile Val Gln Pro Asp Pro Pro Ile Ala Leu Asn Trp Thr Leu Leu
        370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
        435                 440                 445

Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480

<210> SEQ ID NO 12
<211> LENGTH: 455
<212> TYPE: PRT
<213> ORGANISM: artificial sequence
<220> FEATURE:
<223> OTHER INFORMATION: Growth hormone fusion

<400> SEQUENCE: 12

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala Asp Arg Leu Asn Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Asn Ala Asp Met Ser Arg Val Ser Thr Phe Leu Arg Thr Val Gln Cys
        195                 200                 205

Arg Ser Val Glu Gly Ser Cys Gly Phe Phe Ser Gly Ser Glu Ala Thr
    210                 215                 220
```

```
Ala Ala Ile Leu Ser Arg Ala Pro Trp Ser Leu Gln Ser Val Asn Pro
225                 230                 235                 240

Gly Leu Lys Thr Asn Ser Ser Lys Glu Pro Lys Phe Thr Lys Cys Arg
            245                 250                 255

Ser Pro Glu Arg Glu Thr Phe Ser Cys His Trp Thr Asp Glu Val His
        260                 265                 270

His Gly Thr Lys Asn Leu Gly Pro Ile Gln Leu Phe Tyr Thr Arg Arg
    275                 280                 285

Asn Thr Gln Glu Trp Thr Gln Glu Trp Lys Glu Cys Pro Asp Tyr Val
290                 295                 300

Ser Ala Gly Glu Asn Ser Cys Tyr Phe Asn Ser Ser Phe Thr Ser Ile
305                 310                 315                 320

Trp Ile Pro Tyr Cys Ile Lys Leu Thr Ser Asn Gly Gly Thr Val Asp
            325                 330                 335

Glu Lys Cys Phe Ser Val Asp Glu Ile Val Gln Pro Asp Pro Pro Ile
            340                 345                 350

Ala Leu Asn Trp Thr Leu Leu Asn Val Ser Leu Thr Gly Ile His Ala
    355                 360                 365

Asp Ile Gln Val Arg Trp Glu Ala Pro Arg Asn Ala Asp Ile Gln Lys
370                 375                 380

Gly Trp Met Val Leu Glu Tyr Glu Leu Gln Tyr Lys Glu Val Asn Glu
385                 390                 395                 400

Thr Lys Trp Lys Met Met Asp Pro Ile Leu Thr Thr Ser Val Pro Val
            405                 410                 415

Tyr Ser Leu Lys Val Asp Lys Gly Tyr Glu Val Arg Val Arg Ser Lys
            420                 425                 430

Gln Arg Asn Ser Gly Asn Tyr Gly Glu Phe Ser Glu Val Leu Tyr Val
            435                 440                 445

Thr Leu Pro Gln Met Ser Gln
    450                 455

<210> SEQ ID NO 13
<211> LENGTH: 480
<212> TYPE: PRT
<213> ORGANISM: artificial sequence
<220> FEATURE:
<223> OTHER INFORMATION: Growth hormone fusion

<400> SEQUENCE: 13

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
            85                  90                  95

Ser Asn Leu Glu Leu Leu Arg Ile Ser Leu Leu Leu Ile Gln Ser Trp
        100                 105                 110

Leu Glu Pro Val Gln Phe Leu Arg Ser Val Phe Ala Asn Ser Leu Val
    115                 120                 125
```

```
Tyr Gly Ala Ser Asp Ser Asn Val Tyr Asp Leu Leu Lys Asp Leu Glu
    130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
        195                 200                 205
Arg Ser Val Glu Gly Ser Cys Gly Phe Gly Arg Gly Gly Gly Gly
    210                 215                 220
Ser Gly Gly Gly Ser Gly Gly Asn Gly Ser Gly Gly Gly Ser
225                 230                 235                 240
Glu Phe Phe Ser Gly Ser Glu Ala Thr Ala Ala Ile Leu Ser Arg Ala
                245                 250                 255
Pro Trp Ser Leu Gln Ser Val Asn Pro Gly Leu Lys Thr Asn Ser Ser
            260                 265                 270
Lys Glu Pro Lys Phe Thr Lys Cys Arg Ser Pro Glu Arg Glu Thr Phe
        275                 280                 285
Ser Cys His Trp Thr Asp Glu Val His His Gly Thr Lys Asn Leu Gly
    290                 295                 300
Pro Ile Gln Leu Phe Tyr Thr Arg Arg Asn Thr Gln Glu Trp Thr Gln
305                 310                 315                 320
Glu Trp Lys Glu Cys Pro Asp Tyr Val Ser Ala Gly Glu Asn Ser Cys
                325                 330                 335
Tyr Phe Asn Ser Ser Phe Thr Ser Ile Trp Ile Pro Tyr Cys Ile Lys
            340                 345                 350
Leu Thr Ser Asn Gly Gly Thr Val Asp Glu Lys Cys Phe Ser Val Asp
        355                 360                 365
Glu Ile Val Gln Pro Asp Pro Pro Ile Ala Leu Asn Trp Thr Leu Leu
    370                 375                 380
Asn Val Ser Leu Thr Gly Ile His Ala Asp Ile Gln Val Arg Trp Glu
385                 390                 395                 400
Ala Pro Arg Asn Ala Asp Ile Gln Lys Gly Trp Met Val Leu Glu Tyr
                405                 410                 415
Glu Leu Gln Tyr Lys Glu Val Asn Glu Thr Lys Trp Lys Met Met Asp
            420                 425                 430
Pro Ile Leu Thr Thr Ser Val Pro Val Tyr Ser Leu Lys Val Asp Lys
        435                 440                 445
Glu Tyr Glu Val Arg Val Arg Ser Lys Gln Arg Asn Ser Gly Asn Tyr
    450                 455                 460
Gly Glu Phe Ser Glu Val Leu Tyr Val Thr Leu Pro Gln Met Ser Gln
465                 470                 475                 480

<210> SEQ ID NO 14
<211> LENGTH: 480
<212> TYPE: PRT
<213> ORGANISM: artificial sequence
<220> FEATURE:
<223> OTHER INFORMATION: Growth hormone fusion

<400> SEQUENCE: 14

Met Ala Thr Gly Ser Arg Thr Ser Leu Leu Leu Ala Phe Gly Leu Leu
1               5                   10                  15
```

-continued

```
Cys Leu Pro Trp Leu Gln Glu Gly Ser Ala Phe Pro Thr Ile Pro Leu
             20                  25                  30
Ser Arg Leu Phe Asp Asn Ala Met Leu Arg Ala His Arg Leu His Gln
         35                  40                  45
Leu Ala Phe Asp Thr Tyr Gln Glu Phe Glu Glu Ala Tyr Ile Pro Lys
 50                  55                  60
Glu Gln Lys Tyr Ser Phe Leu Gln Asn Pro Gln Thr Ser Leu Cys Phe
 65                  70                  75                  80
Ser Glu Ser Ile Pro Thr Pro Ser Asn Arg Glu Glu Thr Gln Gln Lys
                 85                  90                  95
Ser Asn Leu Glu Leu Leu Arg Ile Ser Leu Leu Leu Ile Gln Ser Trp
            100                 105                 110
Leu Glu Pro Val Gln Phe Leu Arg Ser Val Phe Ala Asn Ser Leu Val
        115                 120                 125
Tyr Gly Ala Ser Asp Ser Asn Val Tyr Asp Leu Leu Lys Asp Leu Glu
130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
        195                 200                 205
Arg Ser Val Glu Gly Ser Cys Gly Phe Gly Gly Gly Ser Gly Gly
210                 215                 220
Gly Gly Ser Gly Gly Asn Gly Ser Gly Gly Gly Ser Gly Gly Gly
225                 230                 235                 240
Gly Ser Phe Ser Gly Ser Glu Ala Thr Ala Ala Ile Leu Ser Arg Ala
                245                 250                 255
Pro Trp Ser Leu Gln Ser Val Asn Pro Gly Leu Lys Thr Asn Ser Ser
            260                 265                 270
Lys Glu Pro Lys Phe Thr Lys Cys Arg Ser Pro Glu Arg Glu Thr Phe
        275                 280                 285
Ser Cys His Trp Thr Asp Glu Val His His Gly Thr Lys Asn Leu Gly
290                 295                 300
Pro Ile Gln Leu Phe Tyr Thr Arg Arg Asn Thr Gln Glu Trp Thr Gln
305                 310                 315                 320
Glu Trp Lys Glu Cys Pro Asp Tyr Val Ser Ala Gly Glu Asn Ser Cys
                325                 330                 335
Tyr Phe Asn Ser Ser Phe Thr Ser Ile Trp Ile Pro Tyr Cys Ile Lys
            340                 345                 350
Leu Thr Ser Asn Gly Gly Thr Val Asp Glu Lys Cys Phe Ser Val Asp
        355                 360                 365
Glu Ile Val Gln Pro Asp Pro Pro Ile Ala Leu Asn Trp Thr Leu Leu
370                 375                 380
Asn Val Ser Leu Thr Gly Ile His Ala Asp Ile Gln Val Arg Trp Glu
385                 390                 395                 400
Ala Pro Arg Asn Ala Asp Ile Gln Lys Gly Trp Met Val Leu Glu Tyr
                405                 410                 415
Glu Leu Gln Tyr Lys Glu Val Asn Glu Thr Lys Trp Lys Met Met Asp
            420                 425                 430
Pro Ile Leu Thr Thr Ser Val Pro Val Tyr Ser Leu Lys Val Asp Lys
```

```
                435                 440                 445
Glu Tyr Glu Val Arg Val Arg Ser Lys Gln Arg Asn Ser Gly Asn Tyr
        450                 455                 460

Gly Glu Phe Ser Glu Val Leu Tyr Val Thr Leu Pro Gln Met Ser Gln
465                 470                 475                 480

<210> SEQ ID NO 15
<211> LENGTH: 480
<212> TYPE: PRT
<213> ORGANISM: artificial sequence
<220> FEATURE:
<223> OTHER INFORMATION: Growth hormone fusion

<400> SEQUENCE: 15

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Arg Gly Gly Gly Gly
    210                 215                 220

Ser Gly Gly Gly Ser Gly Gly Asn Gly Thr Gly Gly Gly Ser
225                 230                 235                 240

Glu Phe Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His Gly Thr Lys Asn Leu Gly
    290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
```

```
                    325                 330                 335
Tyr Phe Asn Ser Ser Phe Thr Ser Ile Trp Ile Pro Tyr Cys Ile Lys
                340                 345                 350
Leu Thr Ser Asn Gly Gly Thr Val Asp Glu Lys Cys Phe Ser Val Asp
                355                 360                 365
Glu Ile Val Gln Pro Asp Pro Pro Ile Ala Leu Asn Trp Thr Leu Leu
            370                 375                 380
Asn Val Ser Leu Thr Gly Ile His Ala Asp Ile Gln Val Arg Trp Glu
385                 390                 395                 400
Ala Pro Arg Asn Ala Asp Ile Gln Lys Gly Trp Met Val Leu Glu Tyr
                405                 410                 415
Glu Leu Gln Tyr Lys Glu Val Asn Glu Thr Lys Trp Lys Met Met Asp
                420                 425                 430
Pro Ile Leu Thr Thr Ser Val Pro Val Tyr Ser Leu Lys Val Asp Lys
                435                 440                 445
Glu Tyr Glu Val Arg Val Arg Ser Lys Gln Arg Asn Ser Gly Asn Tyr
            450                 455                 460
Gly Glu Phe Ser Glu Val Leu Tyr Val Thr Leu Pro Gln Met Ser Gln
465                 470                 475                 480

<210> SEQ ID NO 16
<211> LENGTH: 480
<212> TYPE: PRT
<213> ORGANISM: artificial sequence
<220> FEATURE:
<223> OTHER INFORMATION: Growth hormone fusion

<400> SEQUENCE: 16

Met Ala Thr Gly Ser Arg Thr Ser Leu Leu Leu Ala Phe Gly Leu Leu
1               5                   10                  15
Cys Leu Pro Trp Leu Gln Glu Gly Ser Ala Phe Pro Thr Ile Pro Leu
                20                  25                  30
Ser Arg Leu Phe Asp Asn Ala Met Leu Arg Ala His Arg Leu His Gln
            35                  40                  45
Leu Ala Phe Asp Thr Tyr Gln Glu Phe Glu Glu Ala Tyr Ile Pro Lys
        50                  55                  60
Glu Gln Lys Tyr Ser Phe Leu Gln Asn Pro Gln Thr Ser Leu Cys Phe
65                  70                  75                  80
Ser Glu Ser Ile Pro Thr Pro Ser Asn Arg Glu Glu Thr Gln Gln Lys
                85                  90                  95
Ser Asn Leu Glu Leu Leu Arg Ile Ser Leu Leu Leu Ile Gln Ser Trp
            100                 105                 110
Leu Glu Pro Val Gln Phe Leu Arg Ser Val Phe Ala Asn Ser Leu Val
        115                 120                 125
Tyr Gly Ala Ser Asp Ser Asn Val Tyr Asp Leu Leu Lys Asp Leu Glu
    130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
        195                 200                 205
Arg Ser Val Glu Gly Ser Cys Gly Phe Gly Gly Gly Gly Ser Gly Gly
```

```
                210               215               220
Gly Gly Ser Gly Gly Asn Gly Thr Gly Gly Gly Ser Gly Gly
225             230              235             240

Gly Ser Phe Ser Gly Ser Glu Ala Thr Ala Ala Ile Leu Ser Arg Ala
                245             250             255

Pro Trp Ser Leu Gln Ser Val Asn Pro Gly Leu Lys Thr Asn Ser Ser
            260             265             270

Lys Glu Pro Lys Phe Thr Lys Cys Arg Ser Pro Glu Arg Glu Thr Phe
        275             280             285

Ser Cys His Trp Thr Asp Glu Val His His Gly Thr Lys Asn Leu Gly
    290             295             300

Pro Ile Gln Leu Phe Tyr Thr Arg Arg Asn Thr Gln Glu Trp Thr Gln
305             310             315             320

Glu Trp Lys Glu Cys Pro Asp Tyr Val Ser Ala Gly Glu Asn Ser Cys
                325             330             335

Tyr Phe Asn Ser Ser Phe Thr Ser Ile Trp Ile Pro Tyr Cys Ile Lys
            340             345             350

Leu Thr Ser Asn Gly Gly Thr Val Asp Glu Lys Cys Phe Ser Val Asp
        355             360             365

Glu Ile Val Gln Pro Asp Pro Pro Ile Ala Leu Asn Trp Thr Leu Leu
    370             375             380

Asn Val Ser Leu Thr Gly Ile His Ala Asp Ile Gln Val Arg Trp Glu
385             390             395             400

Ala Pro Arg Asn Ala Asp Ile Gln Lys Gly Trp Met Val Leu Glu Tyr
                405             410             415

Glu Leu Gln Tyr Lys Glu Val Asn Glu Thr Lys Trp Lys Met Met Asp
            420             425             430

Pro Ile Leu Thr Thr Ser Val Pro Val Tyr Ser Leu Lys Val Asp Lys
        435             440             445

Glu Tyr Glu Val Arg Val Arg Ser Lys Gln Arg Asn Ser Gly Asn Tyr
    450             455             460

Gly Glu Phe Ser Glu Val Leu Tyr Val Thr Leu Pro Gln Met Ser Gln
465             470             475             480

<210> SEQ ID NO 17
<211> LENGTH: 480
<212> TYPE: PRT
<213> ORGANISM: artificial sequence
<220> FEATURE:
<223> OTHER INFORMATION: Growth hormone fusion

<400> SEQUENCE: 17

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
```

```
            100                 105                 110
Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
            130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                    165                 170                 175

His Asn Asp Asp Ala Leu Leu Lys Asn Tyr Gly Leu Leu Tyr Cys Phe
                180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Gly Arg Gly Gly Gly
            210                 215                 220

Ser Gly Gly Gly Ser Gly Trp Asn Gly Ser Gly Gly Gly Ser
225                 230                 235                 240

Glu Phe Phe Ser Gly Ser Glu Ala Thr Ala Ala Ile Leu Ser Arg Ala
                    245                 250                 255

Pro Trp Ser Leu Gln Ser Val Asn Pro Gly Leu Lys Thr Asn Ser Ser
                260                 265                 270

Lys Glu Pro Lys Phe Thr Lys Cys Arg Ser Pro Glu Arg Glu Thr Phe
            275                 280                 285

Ser Cys His Trp Thr Asp Glu Val His His Gly Thr Lys Asn Leu Gly
290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                    325                 330                 335

Tyr Phe Asn Ser Ser Phe Thr Ser Ile Trp Ile Pro Tyr Cys Ile Lys
                340                 345                 350

Leu Thr Ser Asn Gly Gly Thr Val Asp Glu Lys Cys Phe Ser Val Asp
            355                 360                 365

Glu Ile Val Gln Pro Asp Pro Pro Ile Ala Leu Asn Trp Thr Leu Leu
370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                    405                 410                 415

Glu Leu Gln Tyr Lys Glu Val Asn Glu Thr Lys Trp Lys Met Met Asp
                420                 425                 430

Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
450                 455                 460

Gly Glu Phe Ser Glu Val Leu Tyr Val Thr Leu Pro Gln Met Ser Gln
465                 470                 475                 480

<210> SEQ ID NO 18
<211> LENGTH: 480
<212> TYPE: PRT
<213> ORGANISM: artificial sequence
<220> FEATURE:
<223> OTHER INFORMATION: Growth hormone fusion
```

```
<400> SEQUENCE: 18

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Gly Ser Gly Gly
210                 215                 220

Gly Gly Ser Gly Trp Asn Gly Ser Gly Gly Gly Ser Gly Gly Gly
225                 230                 235                 240

Gly Ser Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
        290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
        355                 360                 365

Glu Ile Val Gln Pro Asp Pro Pro Ile Ala Leu Asn Trp Thr Leu Leu
370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
            405                 410                 415
```

-continued

```
Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
        450                 455                 460

Gly Glu Phe Ser Glu Val Leu Tyr Val Thr Leu Pro Gln Met Ser Gln
465                 470                 475                 480

<210> SEQ ID NO 19
<211> LENGTH: 483
<212> TYPE: PRT
<213> ORGANISM: artificial sequence
<220> FEATURE:
<223> OTHER INFORMATION: Growth hormone fusion

<400> SEQUENCE: 19

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Arg Gly Gly Gly Gly
    210                 215                 220

Ser Gly Gly Gly Gly Ser Gly Gly Gly Gly Ser Asn Ala Thr Gly Gly
225                 230                 235                 240

Gly Gly Ser Glu Phe Phe Ser Gly Ser Glu Ala Thr Ala Ala Ile Leu
                245                 250                 255

Ser Arg Ala Pro Trp Ser Leu Gln Ser Val Asn Pro Gly Leu Lys Thr
            260                 265                 270

Asn Ser Ser Lys Glu Pro Lys Phe Thr Lys Cys Arg Ser Pro Glu Arg
        275                 280                 285

Glu Thr Phe Ser Cys His Trp Thr Asp Glu Val His His Gly Thr Lys
    290                 295                 300
```

```
Asn Leu Gly Pro Ile Gln Leu Phe Tyr Thr Arg Arg Asn Thr Gln Glu
305                 310                 315                 320

Trp Thr Gln Glu Trp Lys Glu Cys Pro Asp Tyr Val Ser Ala Gly Glu
                325                 330                 335

Asn Ser Cys Tyr Phe Asn Ser Ser Phe Thr Ser Ile Trp Ile Pro Tyr
            340                 345                 350

Cys Ile Lys Leu Thr Ser Asn Gly Gly Thr Val Asp Glu Lys Cys Phe
            355                 360                 365

Ser Val Asp Glu Ile Val Gln Pro Asp Pro Ile Ala Leu Asn Trp
        370                 375                 380

Thr Leu Leu Asn Val Ser Leu Thr Gly Ile His Ala Asp Ile Gln Val
385                 390                 395                 400

Arg Trp Glu Ala Pro Arg Asn Ala Asp Ile Gln Lys Gly Trp Met Val
                405                 410                 415

Leu Glu Tyr Glu Leu Gln Tyr Lys Glu Val Asn Glu Thr Lys Trp Lys
            420                 425                 430

Met Met Asp Pro Ile Leu Thr Thr Ser Val Pro Val Tyr Ser Leu Lys
        435                 440                 445

Val Asp Lys Glu Tyr Glu Val Arg Val Arg Ser Lys Gln Arg Asn Ser
    450                 455                 460

Gly Asn Tyr Gly Glu Phe Ser Glu Val Leu Tyr Val Thr Leu Pro Gln
465                 470                 475                 480

Met Ser Gln

<210> SEQ ID NO 20
<211> LENGTH: 483
<212> TYPE: PRT
<213> ORGANISM: artificial sequence
<220> FEATURE:
<223> OTHER INFORMATION: Growth hormone fusion

<400> SEQUENCE: 20

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
    115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175
```

```
His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Gly Ser Gly Gly
    210                 215                 220

Gly Gly Ser Gly Gly Gly Ser Asn Ala Thr Gly Gly Gly Ser
225                 230                 235                 240

Gly Gly Gly Gly Ser Phe Ser Gly Ser Glu Ala Thr Ala Ala Ile Leu
                245                 250                 255

Ser Arg Ala Pro Trp Ser Leu Gln Ser Val Asn Pro Gly Leu Lys Thr
            260                 265                 270

Asn Ser Ser Lys Glu Pro Lys Phe Thr Lys Cys Arg Ser Pro Glu Arg
        275                 280                 285

Glu Thr Phe Ser Cys His Trp Thr Asp Glu Val His His Gly Thr Lys
    290                 295                 300

Asn Leu Gly Pro Ile Gln Leu Phe Tyr Thr Arg Arg Asn Thr Gln Glu
305                 310                 315                 320

Trp Thr Gln Glu Trp Lys Glu Cys Pro Asp Tyr Val Ser Ala Gly Glu
                325                 330                 335

Asn Ser Cys Tyr Phe Asn Ser Ser Phe Thr Ser Ile Trp Ile Pro Tyr
            340                 345                 350

Cys Ile Lys Leu Thr Ser Asn Gly Gly Thr Val Asp Glu Lys Cys Phe
        355                 360                 365

Ser Val Asp Glu Ile Val Gln Pro Asp Pro Ile Ala Leu Asn Trp
    370                 375                 380

Thr Leu Leu Asn Val Ser Leu Thr Gly Ile His Ala Asp Ile Gln Val
385                 390                 395                 400

Arg Trp Glu Ala Pro Arg Asn Ala Asp Ile Gln Lys Gly Trp Met Val
                405                 410                 415

Leu Glu Tyr Glu Leu Gln Tyr Lys Glu Val Asn Glu Thr Lys Trp Lys
            420                 425                 430

Met Met Asp Pro Ile Leu Thr Thr Ser Val Pro Val Tyr Ser Leu Lys
        435                 440                 445

Val Asp Lys Glu Tyr Glu Val Arg Val Arg Ser Lys Gln Arg Asn Ser
    450                 455                 460

Gly Asn Tyr Gly Glu Phe Ser Glu Val Leu Tyr Val Thr Leu Pro Gln
465                 470                 475                 480

Met Ser Gln

<210> SEQ ID NO 21
<211> LENGTH: 480
<212> TYPE: PRT
<213> ORGANISM: artificial sequence
<220> FEATURE:
<223> OTHER INFORMATION: Growth hormone fusion

<400> SEQUENCE: 21

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
```

```
             50                  55                  60
Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
            130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Gly Gly Arg Gly Gly Gly Gly
            210                 215                 220

Ser Gly Gly Gly Gly Ser Gly Gly Asn Gly Ser Gly Gly Gly Gly Ser
225                 230                 235                 240

Glu Phe Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
            275                 280                 285

Ser Cys His Trp Thr Asp Glu Val His His Gly Thr Lys Asn Leu Gly
            290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
            355                 360                 365

Glu Ile Val Gln Pro Asp Pro Pro Ile Ala Leu Asn Trp Thr Leu Leu
370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
            450                 455                 460

Gly Glu Phe Ser Glu Val Leu Tyr Val Thr Leu Pro Gln Met Ser Gln
465                 470                 475                 480
```

<210> SEQ ID NO 22
<211> LENGTH: 480
<212> TYPE: PRT
<213> ORGANISM: artificial sequence
<220> FEATURE:
<223> OTHER INFORMATION: Growth hormone fusion

<400> SEQUENCE: 22

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Gly Ser Gly Gly
    210                 215                 220

Gly Gly Ser Gly Gly Asn Gly Ser Gly Gly Gly Ser Gly Gly Gly
225                 230                 235                 240

Gly Ser Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
    290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
        355                 360                 365
```

```
Glu Ile Val Gln Pro Asp Pro Ile Ala Leu Asn Trp Thr Leu Leu
        370             375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480
```

<210> SEQ ID NO 23
<211> LENGTH: 480
<212> TYPE: PRT
<213> ORGANISM: artificial sequence
<220> FEATURE:
<223> OTHER INFORMATION: Growth hormone fusion

<400> SEQUENCE: 23

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala Asp Arg Leu Asn Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Asn Ala Asp Met Ser Arg Val Ser Thr Phe Leu Arg Thr Val Gln Cys
        195                 200                 205

Arg Ser Val Glu Gly Ser Cys Gly Phe Gly Gly Arg Gly Gly Gly Gly
    210                 215                 220

Ser Gly Gly Gly Gly Ser Gly Gly Asn Gly Ser Gly Gly Gly Gly Ser
225                 230                 235                 240

Glu Phe Phe Ser Gly Ser Glu Ala Thr Ala Ala Ile Leu Ser Arg Ala
                245                 250                 255
```

```
Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Arg Glu Thr Phe
            275                 280                 285

Ser Cys His Trp Thr Asp Glu Val His His Gly Thr Lys Asn Leu Gly
            290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
            355                 360                 365

Glu Ile Val Gln Pro Asp Pro Pro Ile Ala Leu Asn Trp Thr Leu Leu
370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
            450                 455                 460

Gly Glu Phe Ser Glu Val Leu Tyr Val Thr Leu Pro Gln Met Ser Gln
465                 470                 475                 480

<210> SEQ ID NO 24
<211> LENGTH: 480
<212> TYPE: PRT
<213> ORGANISM: artificial sequence
<220> FEATURE:
<223> OTHER INFORMATION: Growth hormone fusion

<400> SEQUENCE: 24

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala Asp Arg Leu Asn Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
            85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140
```

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Asn Ala Asp Met Ser Arg Val Ser Thr Phe Leu Arg Thr Val Gln Cys
        195                 200                 205

Arg Ser Val Glu Gly Ser Cys Gly Phe Gly Gly Gly Ser Gly Gly
    210                 215                 220

Gly Gly Ser Gly Gly Asn Gly Ser Gly Gly Gly Ser Gly Gly
225                 230                 235                 240

Gly Ser Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
                260                 265                 270

Lys Glu Pro Lys Phe Thr Lys Cys Arg Ser Pro Glu Arg Glu Thr Phe
            275                 280                 285

Ser Cys His Trp Thr Asp Glu Val His His Gly Thr Lys Asn Leu Gly
            290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
                340                 345                 350

Leu Thr Ser Asn Gly Gly Thr Val Asp Glu Lys Cys Phe Ser Val Asp
            355                 360                 365

Glu Ile Val Gln Pro Asp Pro Pro Ile Ala Leu Asn Trp Thr Leu Leu
370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
            450                 455                 460

Gly Glu Phe Ser Glu Val Leu Tyr Val Thr Leu Pro Gln Met Ser Gln
465                 470                 475                 480

<210> SEQ ID NO 25
<211> LENGTH: 480
<212> TYPE: PRT
<213> ORGANISM: artificial sequence
<220> FEATURE:
<223> OTHER INFORMATION: Growth hormone fusion

<400> SEQUENCE: 25

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

```
Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                      70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
        130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
                180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Gly Gly Arg Gly Gly Gly Gly
        210                 215                 220

Ser Gly Gly Gly Gly Ser Gly Trp Asn Gly Ser Gly Gly Gly Gly Ser
225                 230                 235                 240

Glu Phe Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
                260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
        290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
                340                 345                 350

Leu Thr Ser Asn Gly Gly Thr Val Asp Glu Lys Cys Phe Ser Val Asp
        355                 360                 365

Glu Ile Val Gln Pro Asp Pro Pro Ile Ala Leu Asn Trp Thr Leu Leu
        370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
        435                 440                 445
```

Glu Tyr Glu Val Arg Val Arg Ser Lys Gln Arg Asn Ser Gly Asn Tyr
450                 455                 460

Gly Glu Phe Ser Glu Val Leu Tyr Val Thr Leu Pro Gln Met Ser Gln
465                 470                 475                 480

<210> SEQ ID NO 26
<211> LENGTH: 480
<212> TYPE: PRT
<213> ORGANISM: artificial sequence
<220> FEATURE:
<223> OTHER INFORMATION: Growth hormone fusion

<400> SEQUENCE: 26

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
    115                 120                 125

Tyr Gly Ala Ser Asp Ser Asn Val Tyr Asp Leu Leu Lys Asp Leu Glu
130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
    195                 200                 205

Arg Ser Val Glu Gly Ser Cys Gly Phe Gly Gly Gly Ser Gly Gly
210                 215                 220

Gly Gly Ser Gly Trp Asn Gly Ser Gly Gly Gly Ser Gly Gly Gly
225                 230                 235                 240

Gly Ser Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
    275                 280                 285

Ser Cys His Trp Thr Asp Glu Val His His Gly Thr Lys Asn Leu Gly
290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

-continued

Tyr Phe Asn Ser Ser Phe Thr Ser Ile Trp Ile Pro Tyr Cys Ile Lys
              340                 345                 350

Leu Thr Ser Asn Gly Gly Thr Val Asp Glu Lys Cys Phe Ser Val Asp
          355                 360                 365

Glu Ile Val Gln Pro Asp Pro Pro Ile Ala Leu Asn Trp Thr Leu Leu
      370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
        435                 440                 445

Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480

<210> SEQ ID NO 27
<211> LENGTH: 480
<212> TYPE: PRT
<213> ORGANISM: artificial sequence
<220> FEATURE:
<223> OTHER INFORMATION: Growth hormone fusion

<400> SEQUENCE: 27

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala Asp Arg Leu Asn Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Asn Ala Asp Met Ser Arg Val Ser Thr Phe Leu Arg Thr Val Gln Cys
        195                 200                 205

Arg Ser Val Glu Gly Ser Cys Gly Phe Gly Gly Arg Gly Gly Gly Gly
    210                 215                 220

```
Ser Gly Gly Gly Gly Ser Gly Trp Asn Gly Ser Gly Gly Gly Gly Ser
225                 230                 235                 240

Glu Phe Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
    290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
        355                 360                 365

Glu Ile Val Gln Pro Asp Pro Pro Ile Ala Leu Asn Trp Thr Leu Leu
370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
        435                 440                 445

Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480

<210> SEQ ID NO 28
<211> LENGTH: 480
<212> TYPE: PRT
<213> ORGANISM: artificial sequence
<220> FEATURE:
<223> OTHER INFORMATION: Growth hormone fusion

<400> SEQUENCE: 28

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala Asp Arg Leu Asn Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110
```

```
Leu Glu Pro Val Gln Phe Leu Arg Ser Val Phe Ala Asn Ser Leu Val
            115                 120                 125
Tyr Gly Ala Ser Asp Ser Asn Val Tyr Asp Leu Leu Lys Asp Leu Glu
        130                 135                 140
Glu Arg Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Asn Ala Asp Met Ser Arg Val Ser Thr Phe Leu Arg Thr Val Gln Cys
        195                 200                 205
Arg Ser Val Glu Gly Ser Cys Gly Phe Gly Gly Gly Ser Gly Gly
210                 215                 220
Gly Gly Ser Gly Trp Asn Gly Ser Gly Gly Gly Ser Gly Gly Gly
225                 230                 235                 240
Gly Ser Phe Ser Gly Ser Glu Ala Thr Ala Ala Ile Leu Ser Arg Ala
                245                 250                 255
Pro Trp Ser Leu Gln Ser Val Asn Pro Gly Leu Lys Thr Asn Ser Ser
            260                 265                 270
Lys Glu Pro Lys Phe Thr Lys Cys Arg Ser Pro Glu Arg Glu Thr Phe
        275                 280                 285
Ser Cys His Trp Thr Asp Glu Val His His Gly Thr Lys Asn Leu Gly
290                 295                 300
Pro Ile Gln Leu Phe Tyr Thr Arg Arg Asn Thr Gln Glu Trp Thr Gln
305                 310                 315                 320
Glu Trp Lys Glu Cys Pro Asp Tyr Val Ser Ala Gly Glu Asn Ser Cys
                325                 330                 335
Tyr Phe Asn Ser Ser Phe Thr Ser Ile Trp Ile Pro Tyr Cys Ile Lys
            340                 345                 350
Leu Thr Ser Asn Gly Gly Thr Val Asp Glu Lys Cys Phe Ser Val Asp
        355                 360                 365
Glu Ile Val Gln Pro Asp Pro Pro Ile Ala Leu Asn Trp Thr Leu Leu
370                 375                 380
Asn Val Ser Leu Thr Gly Ile His Ala Asp Ile Gln Val Arg Trp Glu
385                 390                 395                 400
Ala Pro Arg Asn Ala Asp Ile Gln Lys Gly Trp Met Val Leu Glu Tyr
                405                 410                 415
Glu Leu Gln Tyr Lys Glu Val Asn Glu Thr Lys Trp Lys Met Met Asp
            420                 425                 430
Pro Ile Leu Thr Thr Ser Val Pro Val Tyr Ser Leu Lys Val Asp Lys
        435                 440                 445
Glu Tyr Glu Val Arg Val Arg Ser Lys Gln Arg Asn Ser Gly Asn Tyr
450                 455                 460
Gly Glu Phe Ser Glu Val Leu Tyr Val Thr Leu Pro Gln Met Ser Gln
465                 470                 475                 480

<210> SEQ ID NO 29
<211> LENGTH: 483
<212> TYPE: PRT
<213> ORGANISM: artificial sequence
<220> FEATURE:
<223> OTHER INFORMATION: Growth hormone fusion

<400> SEQUENCE: 29
```

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Arg Gly Gly Gly Gly
    210                 215                 220

Ser Gly Gly Gly Gly Ser Gly Gly Gly Ser Asn Ala Thr Gly Gly
225                 230                 235                 240

Gly Gly Ser Glu Phe Phe Ser Gly Ser Glu Ala Thr Ala Ala Ile Leu
                245                 250                 255

Ser Arg Ala Pro Trp Ser Leu Gln Ser Val Asn Pro Gly Leu Lys Thr
            260                 265                 270

Asn Ser Ser Lys Glu Pro Lys Phe Thr Lys Cys Arg Ser Pro Glu Arg
        275                 280                 285

Glu Thr Phe Ser Cys His Trp Thr Asp Glu Val His His Gly Thr Lys
    290                 295                 300

Asn Leu Gly Pro Ile Gln Leu Phe Tyr Thr Arg Arg Asn Thr Gln Glu
305                 310                 315                 320

Trp Thr Gln Glu Trp Lys Glu Cys Pro Asp Tyr Val Ser Ala Gly Glu
                325                 330                 335

Asn Ser Cys Tyr Phe Asn Ser Ser Phe Thr Ser Ile Trp Ile Pro Tyr
            340                 345                 350

Cys Ile Lys Leu Thr Ser Asn Gly Gly Thr Val Asp Glu Lys Cys Phe
        355                 360                 365

Ser Val Asp Glu Ile Val Gln Pro Asp Pro Pro Ile Ala Leu Asn Trp
    370                 375                 380

Thr Leu Leu Asn Val Ser Leu Thr Gly Ile His Ala Asp Ile Gln Val
385                 390                 395                 400

Arg Trp Glu Ala Pro Arg Asn Ala Asp Ile Gln Lys Gly Trp Met Val
                405                 410                 415

Leu Glu Tyr Glu Leu Gln Tyr Lys Glu Val Asn Glu Thr Lys Trp Lys
```

Met Met Asp Pro Ile Leu Thr Thr Ser Val Pro Val Tyr Ser Leu Lys
            420                 425                 430

Val Asp Lys Glu Tyr Glu Val Arg Val Arg Ser Lys Gln Arg Asn Ser
    435                 440                 445

Gly Asn Tyr Gly Glu Phe Ser Glu Val Leu Tyr Val Thr Leu Pro Gln
465                 470                 475                 480

Met Ser Gln

<210> SEQ ID NO 30
<211> LENGTH: 483
<212> TYPE: PRT
<213> ORGANISM: artificial sequence
<220> FEATURE:
<223> OTHER INFORMATION: Growth hormone fusion

<400> SEQUENCE: 30

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Gly Ser Gly Gly
210                 215                 220

Gly Gly Ser Gly Gly Gly Ser Asn Ala Thr Gly Gly Gly Ser
225                 230                 235                 240

Gly Gly Gly Gly Ser Phe Ser Gly Ser Glu Ala Thr Ala Ala Ile Leu
                245                 250                 255

Ser Arg Ala Pro Trp Ser Leu Gln Ser Val Asn Pro Gly Leu Lys Thr
            260                 265                 270

Asn Ser Ser Lys Glu Pro Lys Phe Thr Lys Cys Arg Ser Pro Glu Arg
        275                 280                 285

Glu Thr Phe Ser Cys His Trp Thr Asp Glu Val His His Gly Thr Lys
290                 295                 300

```
Asn Leu Gly Pro Ile Gln Leu Phe Tyr Thr Arg Arg Asn Thr Gln Glu
305                 310                 315                 320

Trp Thr Gln Glu Trp Lys Glu Cys Pro Asp Tyr Val Ser Ala Gly Glu
            325                 330                 335

Asn Ser Cys Tyr Phe Asn Ser Ser Phe Thr Ser Ile Trp Ile Pro Tyr
            340                 345                 350

Cys Ile Lys Leu Thr Ser Asn Gly Gly Thr Val Asp Glu Lys Cys Phe
            355                 360                 365

Ser Val Asp Glu Ile Val Gln Pro Asp Pro Ile Ala Leu Asn Trp
370                 375                 380

Thr Leu Leu Asn Val Ser Leu Thr Gly Ile His Ala Asp Ile Gln Val
385                 390                 395                 400

Arg Trp Glu Ala Pro Arg Asn Ala Asp Ile Gln Lys Gly Trp Met Val
                405                 410                 415

Leu Glu Tyr Glu Leu Gln Tyr Lys Glu Val Asn Glu Thr Lys Trp Lys
            420                 425                 430

Met Met Asp Pro Ile Leu Thr Thr Ser Val Pro Val Tyr Ser Leu Lys
            435                 440                 445

Val Asp Lys Glu Tyr Glu Val Arg Val Arg Ser Lys Gln Arg Asn Ser
            450                 455                 460

Gly Asn Tyr Gly Glu Phe Ser Glu Val Leu Tyr Val Thr Leu Pro Gln
465                 470                 475                 480

Met Ser Gln

<210> SEQ ID NO 31
<211> LENGTH: 483
<212> TYPE: PRT
<213> ORGANISM: artificial sequence
<220> FEATURE:
<223> OTHER INFORMATION: Growth hormone fusion

<400> SEQUENCE: 31

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala Asp Arg Leu Asn Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175
```

His Asn Asp Asp Ala Leu Leu Lys Asn Tyr Gly Leu Leu Tyr Cys Phe
                180                 185                 190

Asn Ala Asp Met Ser Arg Val Ser Thr Phe Leu Arg Thr Val Gln Cys
            195                 200                 205

Arg Ser Val Glu Gly Ser Cys Gly Phe Gly Gly Arg Gly Gly Gly Gly
        210                 215                 220

Ser Gly Gly Gly Ser Gly Gly Gly Ser Asn Ala Thr Gly Gly
225                 230                 235                 240

Gly Gly Ser Glu Phe Phe Ser Gly Ser Glu Ala Thr Ala Ala Ile Leu
                245                 250                 255

Ser Arg Ala Pro Trp Ser Leu Gln Ser Val Asn Pro Gly Leu Lys Thr
            260                 265                 270

Asn Ser Ser Lys Glu Pro Lys Phe Thr Lys Cys Arg Ser Pro Glu Arg
        275                 280                 285

Glu Thr Phe Ser Cys His Trp Thr Asp Glu Val His His Gly Thr Lys
    290                 295                 300

Asn Leu Gly Pro Ile Gln Leu Phe Tyr Thr Arg Arg Asn Thr Gln Glu
305                 310                 315                 320

Trp Thr Gln Glu Trp Lys Glu Cys Pro Asp Tyr Val Ser Ala Gly Glu
                325                 330                 335

Asn Ser Cys Tyr Phe Asn Ser Ser Phe Thr Ser Ile Trp Ile Pro Tyr
            340                 345                 350

Cys Ile Lys Leu Thr Ser Asn Gly Gly Thr Val Asp Glu Lys Cys Phe
        355                 360                 365

Ser Val Asp Glu Ile Val Gln Pro Asp Pro Pro Ile Ala Leu Asn Trp
    370                 375                 380

Thr Leu Leu Asn Val Ser Leu Thr Gly Ile His Ala Asp Ile Gln Val
385                 390                 395                 400

Arg Trp Glu Ala Pro Arg Asn Ala Asp Ile Gln Lys Gly Trp Met Val
                405                 410                 415

Leu Glu Tyr Glu Leu Gln Tyr Lys Glu Val Asn Glu Thr Lys Trp Lys
            420                 425                 430

Met Met Asp Pro Ile Leu Thr Thr Ser Val Pro Val Tyr Ser Leu Lys
        435                 440                 445

Val Asp Lys Glu Tyr Glu Val Arg Val Arg Ser Lys Gln Arg Asn Ser
    450                 455                 460

Gly Asn Tyr Gly Glu Phe Ser Glu Val Leu Tyr Val Thr Leu Pro Gln
465                 470                 475                 480

Met Ser Gln

<210> SEQ ID NO 32
<211> LENGTH: 483
<212> TYPE: PRT
<213> ORGANISM: artificial sequence
<220> FEATURE:
<223> OTHER INFORMATION: Growth hormone fusion

<400> SEQUENCE: 32

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala Asp Arg Leu Asn Gln
            35                  40                  45

Leu Ala Phe Asp Thr Tyr Gln Glu Phe Glu Glu Ala Tyr Ile Pro Lys

```
        50                  55                  60
Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
                115                 120                 125

Tyr Gly Ala Ser Asp Ser Asn Val Tyr Asp Leu Leu Lys Asp Leu Glu
                130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
                180                 185                 190

Asn Ala Asp Met Ser Arg Val Ser Thr Phe Leu Arg Thr Val Gln Cys
                195                 200                 205

Arg Ser Val Glu Gly Ser Cys Gly Phe Gly Gly Gly Ser Gly Gly
210                 215                 220

Gly Gly Ser Gly Gly Gly Ser Asn Ala Thr Gly Gly Gly Ser
225                 230                 235                 240

Gly Gly Gly Gly Ser Phe Ser Gly Ser Glu Ala Thr Ala Ala Ile Leu
                245                 250                 255

Ser Arg Ala Pro Trp Ser Leu Gln Ser Val Asn Pro Gly Leu Lys Thr
                260                 265                 270

Asn Ser Ser Lys Glu Pro Lys Phe Thr Lys Cys Arg Ser Pro Glu Arg
                275                 280                 285

Glu Thr Phe Ser Cys His Trp Thr Asp Glu Val His His Gly Thr Lys
                290                 295                 300

Asn Leu Gly Pro Ile Gln Leu Phe Tyr Thr Arg Arg Asn Thr Gln Glu
305                 310                 315                 320

Trp Thr Gln Glu Trp Lys Glu Cys Pro Asp Tyr Val Ser Ala Gly Glu
                325                 330                 335

Asn Ser Cys Tyr Phe Asn Ser Ser Phe Thr Ser Ile Trp Ile Pro Tyr
                340                 345                 350

Cys Ile Lys Leu Thr Ser Asn Gly Gly Thr Val Asp Glu Lys Cys Phe
                355                 360                 365

Ser Val Asp Glu Ile Val Gln Pro Asp Pro Pro Ile Ala Leu Asn Trp
                370                 375                 380

Thr Leu Leu Asn Val Ser Leu Thr Gly Ile His Ala Asp Ile Gln Val
385                 390                 395                 400

Arg Trp Glu Ala Pro Arg Asn Ala Asp Ile Gln Lys Gly Trp Met Val
                405                 410                 415

Leu Glu Tyr Glu Leu Gln Tyr Lys Glu Val Asn Glu Thr Lys Trp Lys
                420                 425                 430

Met Met Asp Pro Ile Leu Thr Thr Ser Val Pro Val Tyr Ser Leu Lys
                435                 440                 445

Val Asp Lys Glu Tyr Glu Val Arg Val Arg Ser Lys Gln Arg Asn Ser
                450                 455                 460

Gly Asn Tyr Gly Glu Phe Ser Glu Val Leu Tyr Val Thr Leu Pro Gln
465                 470                 475                 480
```

Met Ser Gln

<210> SEQ ID NO 33
<211> LENGTH: 455
<212> TYPE: PRT
<213> ORGANISM: artificial sequence
<220> FEATURE:
<223> OTHER INFORMATION: Growth hormone fusion

<400> SEQUENCE: 33

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala Asp Arg Leu Asn Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Asn Ala Asp Met Ser Arg Val Ser Thr Phe Leu Arg Thr Val Gln Cys
        195                 200                 205

Arg Ser Val Glu Gly Ser Cys Gly Phe Phe Ser Gly Ser Glu Ala Thr
    210                 215                 220

Ala Ala Ile Leu Ser Arg Ala Pro Trp Ser Leu Gln Ser Val Asn Pro
225                 230                 235                 240

Gly Leu Lys Thr Asn Ser Ser Lys Glu Pro Lys Phe Thr Lys Cys Arg
                245                 250                 255

Ser Pro Glu Arg Glu Thr Phe Ser Cys His Trp Thr Asp Glu Val His
            260                 265                 270

His Gly Thr Lys Asn Leu Gly Pro Ile Gln Leu Phe Tyr Thr Arg Arg
        275                 280                 285

Asn Thr Gln Glu Trp Thr Gln Glu Trp Lys Glu Cys Pro Asp Tyr Val
    290                 295                 300

Ser Ala Gly Glu Asn Ser Cys Tyr Phe Asn Ser Ser Phe Thr Ser Ile
305                 310                 315                 320

Ala Ile Pro Tyr Cys Ile Lys Leu Thr Ser Asn Gly Gly Thr Val Asp
                325                 330                 335

Glu Lys Cys Phe Ser Val Asp Glu Ile Val Gln Pro Asp Pro Pro Ile
            340                 345                 350
```

```
Ala Leu Asn Trp Thr Leu Leu Asn Val Ser Leu Thr Gly Ile His Ala
        355                 360                 365

Asp Ile Gln Val Arg Trp Glu Ala Pro Arg Asn Ala Asp Ile Gln Lys
    370                 375                 380

Gly Trp Met Val Leu Glu Tyr Glu Leu Gln Tyr Lys Glu Val Asn Glu
385                 390                 395                 400

Thr Lys Trp Lys Met Met Asp Pro Ile Leu Thr Thr Ser Val Pro Val
                405                 410                 415

Tyr Ser Leu Lys Val Asp Lys Glu Tyr Glu Val Arg Val Arg Ser Lys
            420                 425                 430

Gln Arg Asn Ser Gly Asn Tyr Gly Glu Phe Ser Glu Val Leu Tyr Val
        435                 440                 445

Thr Leu Pro Gln Met Ser Gln
    450                 455

<210> SEQ ID NO 34
<211> LENGTH: 429
<212> TYPE: PRT
<213> ORGANISM: artificial sequence
<220> FEATURE:
<223> OTHER INFORMATION: Growth hormone fusion

<400> SEQUENCE: 34

Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Arg Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Asn Ala Asp Met Ser Arg Val Ser Thr Phe
                165                 170                 175

Leu Arg Thr Val Gln Cys Arg Ser Val Glu Gly Ser Cys Gly Phe Phe
            180                 185                 190

Ser Gly Ser Glu Ala Thr Ala Ala Ile Leu Ser Arg Ala Pro Trp Ser
        195                 200                 205

Leu Gln Ser Val Asn Pro Gly Leu Lys Thr Asn Ser Ser Lys Glu Pro
    210                 215                 220

Lys Phe Thr Lys Cys Arg Ser Pro Glu Arg Glu Thr Phe Ser Cys His
225                 230                 235                 240

Trp Thr Asp Glu Val His His Gly Thr Lys Asn Leu Gly Pro Ile Gln
                245                 250                 255
```

```
Leu Phe Tyr Thr Arg Arg Asn Thr Gln Glu Trp Thr Gln Glu Trp Lys
            260                 265                 270

Glu Cys Pro Asp Tyr Val Ser Ala Gly Glu Asn Ser Cys Tyr Phe Asn
        275                 280                 285

Ser Ser Phe Thr Ser Ile Ala Ile Pro Tyr Cys Ile Lys Leu Thr Ser
        290                 295                 300

Asn Gly Gly Thr Val Asp Glu Lys Cys Phe Ser Val Asp Glu Ile Val
305                 310                 315                 320

Gln Pro Asp Pro Pro Ile Ala Leu Asn Trp Thr Leu Leu Asn Val Ser
                325                 330                 335

Leu Thr Gly Ile His Ala Asp Ile Gln Val Arg Trp Glu Ala Pro Arg
            340                 345                 350

Asn Ala Asp Ile Gln Lys Gly Trp Met Val Leu Glu Tyr Glu Leu Gln
        355                 360                 365

Tyr Lys Glu Val Asn Glu Thr Lys Trp Lys Met Met Asp Pro Ile Leu
370                 375                 380

Thr Thr Ser Val Pro Val Tyr Ser Leu Lys Val Asp Lys Glu Tyr Glu
385                 390                 395                 400

Val Arg Val Arg Ser Lys Gln Arg Asn Ser Gly Asn Tyr Gly Glu Phe
                405                 410                 415

Ser Glu Val Leu Tyr Val Thr Leu Pro Gln Met Ser Gln
            420                 425

<210> SEQ ID NO 35
<211> LENGTH: 5
<212> TYPE: PRT
<213> ORGANISM: Artificial
<220> FEATURE:
<223> OTHER INFORMATION: peptide linking molecule

<400> SEQUENCE: 35

Gly Gly Gly Gly Ser
1               5

<210> SEQ ID NO 36
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (1)..(3)
<223> OTHER INFORMATION: wherein Xaa-Xaa-Xaa can comprise the
      glycosylation motif Asn-Xaa-Ser or Asn-Xaa-Thr
<220> FEATURE:
<221> NAME/KEY: MISC_FEATURE
<222> LOCATION: (1)..(5)
<223> OTHER INFORMATION: Xaa can be any naturally occurring amino acid
<220> FEATURE:
<221> NAME/KEY: MISC_FEATURE
<222> LOCATION: (2)..(4)
<223> OTHER INFORMATION: wherein Xaa-Xaa-Xaa can comprise the
      glycosylation motif Asn-Xaa-Ser or Asn-Xaa-Thr
<220> FEATURE:
<221> NAME/KEY: MISC_FEATURE
<222> LOCATION: (3)..(5)
<223> OTHER INFORMATION: wherein Xaa-Xaa-Xaa can comprise the
      glycosylation motif Asn-Xaa-Ser or Asn-Xaa-Thr

<400> SEQUENCE: 36

Xaa Xaa Xaa Xaa Xaa
1               5
```

```
<210> SEQ ID NO 37
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: wherein X is any amino acid residue apart from
      proline
<220> FEATURE:
<221> NAME/KEY: misc_feature
<222> LOCATION: (4)..(5)
<223> OTHER INFORMATION: Xaa can be any naturally occurring amino acid

<400> SEQUENCE: 37

Asn Xaa Ser Xaa Xaa
1               5

<210> SEQ ID NO 38
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: wherein X is any amino acid residue apart from
      proline
<220> FEATURE:
<221> NAME/KEY: misc_feature
<222> LOCATION: (5)..(5)
<223> OTHER INFORMATION: Xaa can be any naturally occurring amino acid

<400> SEQUENCE: 38

Xaa Asn Xaa Ser Xaa
1               5

<210> SEQ ID NO 39
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: wherein X is any amino acid residue apart from
      proline

<400> SEQUENCE: 39

Xaa Xaa Asn Xaa Ser
1               5

<210> SEQ ID NO 40
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (2)..(2)
```

```
<223> OTHER INFORMATION: wherein X is any amino acid residue except
      proline
<220> FEATURE:
<221> NAME/KEY: misc_feature
<222> LOCATION: (4)..(5)
<223> OTHER INFORMATION: Xaa can be any naturally occurring amino acid

<400> SEQUENCE: 40

Asn Xaa Thr Xaa Xaa
1               5

<210> SEQ ID NO 41
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: wherein X is any amino acid residue except
      proline
<220> FEATURE:
<221> NAME/KEY: misc_feature
<222> LOCATION: (5)..(5)
<223> OTHER INFORMATION: Xaa can be any naturally occurring amino acid

<400> SEQUENCE: 41

Xaa Asn Xaa Thr Xaa
1               5

<210> SEQ ID NO 42
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: wherein X is any amino acid residue except
      proline

<400> SEQUENCE: 42

Xaa Xaa Asn Xaa Thr
1               5

<210> SEQ ID NO 43
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: wherein X is any amino acid residue except
      proline

<400> SEQUENCE: 43

Asn Xaa Ser Gly Ser
1               5
```

```
<210> SEQ ID NO 44
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (3)..(3)
<223> OTHER INFORMATION: wherein X is any amino acid residue except
      proline

<400> SEQUENCE: 44

Gly Asn Xaa Ser Ser
1               5

<210> SEQ ID NO 45
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: wherein X is any amino acid residue except
      proline

<400> SEQUENCE: 45

Gly Gly Asn Xaa Ser
1               5

<210> SEQ ID NO 46
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: wherein X is any amino acid residue except
      proline

<400> SEQUENCE: 46

Asn Xaa Thr Gly Ser
1               5

<210> SEQ ID NO 47
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (3)..(3)
<223> OTHER INFORMATION: wherein X is any amino acid residue except
      proline

<400> SEQUENCE: 47

Gly Asn Xaa Thr Ser
1               5

<210> SEQ ID NO 48
<211> LENGTH: 5
<212> TYPE: PRT
<213> ORGANISM: artificial
<220> FEATURE:
<223> OTHER INFORMATION: peptide linker
<220> FEATURE:
```

<221> NAME/KEY: MISC_FEATURE
<222> LOCATION: (4)..(4)
<223> OTHER INFORMATION: wherein X is any amino acid residue except
      proline

<400> SEQUENCE: 48

Gly Gly Asn Xaa Thr
1               5

<210> SEQ ID NO 49
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: wherein X is any amino acid residue except
      proline

<400> SEQUENCE: 49

Asn Xaa Ser Ser Gly
1               5

<210> SEQ ID NO 50
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (3)..(3)
<223> OTHER INFORMATION: wherein X is any amino acid residue except
      proline

<400> SEQUENCE: 50

Ser Asn Xaa Ser Gly
1               5

<210> SEQ ID NO 51
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: wherein X is any amino acid residue except
      proline

<400> SEQUENCE: 51

Ser Ser Asn Xaa Ser
1               5

<210> SEQ ID NO 52
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: wherein X is any amino acid residue except
      proline

<400> SEQUENCE: 52

Asn Xaa Thr Ser Gly
1               5

<210> SEQ ID NO 53
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (3)..(3)
<223> OTHER INFORMATION: wherein X is any amino acid residue except
      proline

<400> SEQUENCE: 53

Ser Asn Xaa Thr Gly
1               5

<210> SEQ ID NO 54
<211> LENGTH: 5
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: wherein X is any amino acid residue except
      proline

<400> SEQUENCE: 54

Ser Ser Asn Xaa Thr
1               5

<210> SEQ ID NO 55
<211> LENGTH: 5
<212> TYPE: PRT
<213> ORGANISM: artificial
<220> FEATURE:
<223> OTHER INFORMATION: peptide linker

<400> SEQUENCE: 55

Ser Ser Ser Ser Gly
1               5

<210> SEQ ID NO 56
<211> LENGTH: 1486
<212> TYPE: DNA
<213> ORGANISM: artificial
<220> FEATURE:
<223> OTHER INFORMATION: nucleotide sequence encoding GH fusion protein
      1B7v0-Hist

<400> SEQUENCE: 56
gctagccacc atggctacag ctcccggac gtccctgctc ctggcttttg gcctgctctg      60
cctgccctgg cttcaagagg gcagtgcctt cccaaccatt cccttatcca ggcttttga    120 caacgctagt ctccgcgccc atcgtctgca ccagctggcc tttgacacct accaggagtt    180
tgaagaagcc tatatcccaa aggaacagaa gtattcattc ctgcagaacc cccagacctc    240
cctctgtttc tcagagtcta ttccgacacc ctccaacagg gaggaaacac aacagaaatc    300
caacctagag ctgctccgca tctccctgct gctcatccag tcgtggctgg agcccgtgca    360
gttcctcagg agtgtcttcg ccaacagcct ggtgtacggc gcctctgaca gcaacgtcta    420
tgacctccta aaggacctag aggaaggcat ccaaacgctg atggggaggc tggaagatgg    480

```
cagcccccgg actgggcaga tcttcaagca gacctacagc aagttcgaca caaactcaca      540
caacgatgac gcactactca agaactacgg gctgctctac tgcttcagga aggacatgga      600
caaggtcgag acattcctgc gcatcgtgca gtgccgctct gtggagggca gctgtggctt      660
cggcggccgc ggtggcggag gtagtggtgg cggaggtagc ggtggcggag gttctggtgg      720
cggaggttcc gaattctttt ctggaagtga ggccacagca gctatcctta gcagagcacc      780
ctggagtctg caaagtgtta atccaggcct aaagacaaat tcttctaagg agcctaaatt      840
caccaagtgc cgttcacctg agcgagagac ttttcatgc cactggacag atgaggttca      900
tcatggtaca agaacctag gacccataca gctgttctat accagaagga acactcaaga      960
atggactcaa gaatggaaag aatgccctga ttatgtttct gctggggaaa acagctgtta     1020
ctttaattca tcgtttacct ccatctggat accttattgt atcaagctaa ctagcaatgg     1080
tggtacagtg gatgaaaagt gtttctctgt tgatgaaata gtgcaaccag atccacccat     1140
tgccctcaac tggactttac tgaacgtcag tttaactggg attcatgcag atatccaagt     1200
gagatgggaa gcaccacgca atgcagatat tcagaaagga tggatggttc tggagtatga     1260
acttcaatac aaagaagtaa atgaaactaa atggaaaatg atggacccta tattgacaac     1320
atcagttcca gtgtactcat tgaaagtgga taaggaatat gaagtacgcg tgagatccaa     1380
acaacgaaac tctggaaatt atggcgagtt cagtgaggtg ctctatgtaa cacttcctca     1440
gatgagccaa aagcttttcg ataccggtca tcatcaccat caccat                    1486

<210> SEQ ID NO 57
<211> LENGTH: 279
<212> TYPE: DNA
<213> ORGANISM: artificial
<220> FEATURE:
<223> OTHER INFORMATION: nucleotide sequence encoding part of GH fusion
      protein

<400> SEQUENCE: 57
gatatccaag tgagatggga agcaccacgc aatgcagata ttcagaaagg atggatggtt       60
ctggagtatg aacttcaata caaagaagta aatgaaacta atggaaaat gatggacccct      120 atattgacaa catcagttcc agtgtactca ttgaaagtgg ataaggaata tgaagtacgc      180
gtgagatcca acaacgaaa ctctggaaat tatggcgagt tcagtgaggt gctctatgta      240
acacttcctc agatgagcca aaagcttttc gataccggt                             279

<210> SEQ ID NO 58
<211> LENGTH: 1501
<212> TYPE: DNA
<213> ORGANISM: artificial
<220> FEATURE:
<223> OTHER INFORMATION: nucleotide sequence encoding GH fusion protein
      1B7v2

<400> SEQUENCE: 58
gctagccacc atggctacag ctcccggac gtccctgctc ctggcttttg gcctgctctg       60
cctgccctgg cttcaagagg gcagtgcctt cccaaccatt cccttatcca ggcttttga      120 caacgctatg ctccgcgccc atcgtctgca ccagctggcc tttgacacct accaggagtt      180
tgaagaagcc tatatcccaa aggaacagaa gtattcattc ctgcagaacc cccagaccctc      240 cctctgtttc tcagagtcta ttccgacacc ctccaacagg gaggaaacac aacagaaatc      300
caacctagag ctgctccgca tctccctgct gctcatccag tcgtggctgg agcccgtgca      360
gttcctcagg agtgtcttcg ccaacagcct ggtgtacggc gcctctgaca gcaacgtcta      420
```

```
tgacctccta aaggacctag aggaaggcat ccaaacgctg atggggaggc tggaagatgg      480
cagcccccgg actgggcaga tcttcaagca gacctacagc aagttcgaca caaactcaca      540
caacgatgac gcactactca agaactacgg gctgctctac tgcttcagga aggacatgga     600
caaggtcgag acattcctgc gcatcgtgca gtgccgctct gtggagggca gctgtggctt      660
cggtggcgga ggtagtggtg gcggaggtag cggtggcgga ggttctggtg gcggaggttc     720
cggtggcgga ggtagttttt ctggaagtga ggccacagca gctatcctta gcagagcacc     780
ctggagtctg caaagtgtta atccaggcct aaagacaaat tcttctaagg agcctaaatt      840
caccaagtgc cgttcacctg agcgagagac ttttcatgc cactggacag atgaggttca      900
tcatggtaca aagaacctag gacccataca gctgttctat accagaagga cactcaaga     960 atggactcaa gaatggaaag aatgccctga ttatgtttct gctggggaaa acagctgtta    1020
ctttaattca tcgtttacct ccatctggat accttattgt atcaagctaa ctagcaatgg    1080
tggtacagtg gatgaaaagt gtttctctgt tgatgaaata gtgcaaccag atccacccat   1140
tgccctcaac tggactttac tgaacgtcag tttaactggg attcatgcag atatccaagt    1200
gagatgggaa gcaccacgca atgcagatat tcagaaagga tggatggttc tggagtatga    1260
acttcaatac aaagaagtaa atgaaactaa atggaaaatg atggacccta tattgacaac    1320
atcagttcca gtgtactcat tgaaagtgga taaggaatat gaagtgcgtg tgagatccaa    1380
acaacgaaac tctggaaatt atggcgagtt cagtgaggtg ctctatgtaa cacttcctca    1440
gatgagccaa taaagctttt cgaataaat cgataccggt catcatcacc atcaccattg    1500
a                                                                     1501
```

<210> SEQ ID NO 59
<211> LENGTH: 1490
<212> TYPE: DNA
<213> ORGANISM: artificial
<220> FEATURE:
<223> OTHER INFORMATION: nucleotide sequence encoding GH fusion protein
      1B7v2 Hist

<400> SEQUENCE: 59

```
gctagcccac catggctaca ggctcccgga cgtccctgct cctggctttt ggcctgctct      60
gcctgccctg gcttcaagag ggcagtgcct tcccaaccat tcccttatcc aggcttttg      120 acaacgctat gctccgcgcc catcgtctgc accagctggc ctttgacacc taccaggagt    180
ttgaagaagc ctatatccca aaggaacaga agtattcatt cctgcagaac ccccagacct    240
ccctctgttt ctcagagtct attccgacac cctccaacag ggaggaaaca caacagaaat    300
ccaacctaga gctgctccgc atctccctgc tgctcatcca gtcgtggctg gagcccgtgc     360
agttcctcag gagtgtcttc gccaacagcc tggtgtacgg cgcctctgac agcaacgtct    420
atgacctcct aaaggaccta gaggaaggca tccaaacgct gatggggagg ctggaagatg    480
gcagcccccg gactgggcag atcttcaagc agacctacag caagttcgac acaaactcac    540
acaacgatga cgcactactc aagaactacg gctgctcta ctgcttcagg aaggacatgg    600
acaaggtcga gacattcctg cgcatcgtgc agtgccgctc tgtggagggc agctgtggct   660
tcggtggcgg aggtagtggt ggcggaggta gcggtggcgg aggttctggt ggcggaggtt   720
ccggtggcgg aggtagtttt tctggaagtg aggccacagc agctatcctt agcagagcac    780
cctggagtct gcaaagtgtt aatccaggcc taaagacaaa ttcttctaag agcctaaat    840 tcaccaagtg ccgttcacct gagcgagaga cttttcatg ccactggaca gatgaggttc   900
```

```
atcatggtac aaagaaccta ggacccatac agctgttcta taccagaagg aacactcaag    960
aatggactca agaatggaaa gaatgccctg attatgtttc tgctggggaa aacagctgtt   1020
actttaattc atcgtttacc tccatctgga taccttattg tatcaagcta actagcaatg   1080
gtggtacagt ggatgaaaag tgtttctctg ttgatgaaat agtgcaacca gatccaccca   1140
ttgccctcaa ctggacttta ctgaacgtca gtttaactgg gattcatgca gatatccaag   1200
tgagatggga agcaccacgc aatgcagata ttcagaaagg atggatggtt ctggagtatg   1260
aacttcaata caagaagta atgaaacta atggaaaat gatggaccct atattgacaa   1320
catcagttcc agtgtactca ttgaaagtgg ataaggaata tgaagtacgc gtgagatcca   1380
aacaacgaaa ctctggaaat tatggcgagt tcagtgaggt gctctatgta acacttcctc   1440
agatgagcca aaagcttttc gataccggtc atcatcacca tcaccattga             1490

<210> SEQ ID NO 60
<211> LENGTH: 717
<212> TYPE: DNA
<213> ORGANISM: artificial
<220> FEATURE:
<223> OTHER INFORMATION: nucleotide sequence encoding GHR part of GH
      fusion protein 1B7

<400> SEQUENCE: 60
ttttctggaa gtgaggccac agcagctatc cttagcagag caccctggag tctgcaaagt     60
gttaatccag gcctaaagac aaattcttct aaggagccta aattcaccaa gtgccgttca    120
cctgagcgag agacttttc atgccactgg acagatgagg ttcatcatgg tacaaagaac    180
ctaggaccca tacagctgtt ctataccaga aggaacactc aagaatggac tcaagaatgg    240
aaagaatgcc ctgattatgt ttctgctggg gaaaacagct gttactttaa ttcatcgttt    300
acctccatcg caataccta ttgtatcaag ctaactagca atggtggtac agtggatgaa    360
aagtgtttct ctgttgatga aatagtgcaa ccagatccac ccattgccct caactggact    420
ttactgaacg tcagtttaac tgggattcat gcagatatcc aagtgagatg ggaagcacca    480
cgcaatgcag atattcagaa aggatggatg gttctggagt atgaacttca atacaaagaa    540
gtaaatgaaa ctaaatggaa aatgatggac cctatattga acacatcagt tccagtgtac    600
tcattgaaag tggataagga atatgaagta cgcgtgagat ccaaacaacg aaactctgga    660
aattatggcg agttcagtga ggtgctctat gtaacacttc tcagatgag ccaataa      717

<210> SEQ ID NO 61
<211> LENGTH: 28
<212> TYPE: DNA
<213> ORGANISM: artificial
<220> FEATURE:
<223> OTHER INFORMATION: nucleotide forward primer GHR

<400> SEQUENCE: 61
aaatttccta ggacccatac agctgttc                                         28

<210> SEQ ID NO 62
<211> LENGTH: 36
<212> TYPE: DNA
<213> ORGANISM: artificial
<220> FEATURE:
<223> OTHER INFORMATION: nucleotide reverse primer GHR

<400> SEQUENCE: 62
aattcatcgt ttacctccat cgcaatacct tattgt                                36
```

```
<210> SEQ ID NO 63
<211> LENGTH: 36
<212> TYPE: DNA
<213> ORGANISM: artificial
<220> FEATURE:
<223> OTHER INFORMATION: nucleotide reverse primer GHR

<400> SEQUENCE: 63
ttaagtagca aatggaggta gcgttatgga ataaca                               36

<210> SEQ ID NO 64
<211> LENGTH: 36
<212> TYPE: DNA
<213> ORGANISM: artificial
<220> FEATURE:
<223> OTHER INFORMATION: nucleotide reverse primer GHR

<400> SEQUENCE: 64
acaataaggt attgcgatgg aggtaaacga tgaatt                               36

<210> SEQ ID NO 65
<211> LENGTH: 28
<212> TYPE: DNA
<213> ORGANISM: artificial
<220> FEATURE:
<223> OTHER INFORMATION: nucleotide forward primer GHR

<400> SEQUENCE: 65
cagtttaact gggattcatg cagatatc                                        28

<210> SEQ ID NO 66
<211> LENGTH: 28
<212> TYPE: DNA
<213> ORGANISM: artificial
<220> FEATURE:
<223> OTHER INFORMATION: nucleotide reverse primer GHR

<400> SEQUENCE: 66
gtcaaattga ccctaagtac gtctatag                                        28

<210> SEQ ID NO 67
<211> LENGTH: 34
<212> TYPE: DNA
<213> ORGANISM: artificial
<220> FEATURE:
<223> OTHER INFORMATION: nucleotide primer GHR

<400> SEQUENCE: 67
aaatttgata tctgcatgaa tcccagttaa actg                                 34

<210> SEQ ID NO 68
<211> LENGTH: 34
<212> TYPE: DNA
<213> ORGANISM: artificial
<220> FEATURE:
<223> OTHER INFORMATION: nucleotide primer GHR

<400> SEQUENCE: 68
cctccatcgc aataccttat tgtatcaagc taac                                 34

<210> SEQ ID NO 69
<211> LENGTH: 238
<212> TYPE: PRT
<213> ORGANISM: Homo sapiens
```

```
<400> SEQUENCE: 69

Phe Ser Gly Ser Glu Ala Thr Ala Ala Ile Leu Ser Arg Ala Pro Trp
1               5                   10                  15

Ser Leu Gln Ser Val Asn Pro Gly Leu Lys Thr Asn Ser Ser Lys Glu
            20                  25                  30

Pro Lys Phe Thr Lys Cys Arg Ser Pro Glu Arg Glu Thr Phe Ser Cys
        35                  40                  45

His Trp Thr Asp Glu Val His His Gly Thr Lys Asn Leu Gly Pro Ile
    50                  55                  60

Gln Leu Phe Tyr Thr Arg Arg Asn Thr Gln Glu Trp Thr Gln Glu Trp
65                  70                  75                  80

Lys Glu Cys Pro Asp Tyr Val Ser Ala Gly Glu Asn Ser Cys Tyr Phe
                85                  90                  95

Asn Ser Ser Phe Thr Ser Ile Trp Ile Pro Tyr Cys Ile Lys Leu Thr
            100                 105                 110

Ser Asn Gly Gly Thr Val Asp Glu Lys Cys Phe Ser Val Asp Glu Ile
        115                 120                 125

Val Gln Pro Asp Pro Ile Ala Leu Asn Trp Thr Leu Leu Asn Val
    130                 135                 140

Ser Leu Thr Gly Ile His Ala Asp Ile Gln Val Arg Trp Glu Ala Pro
145                 150                 155                 160

Arg Asn Ala Asp Ile Gln Lys Gly Trp Met Val Leu Glu Tyr Glu Leu
                165                 170                 175

Gln Tyr Lys Glu Val Asn Glu Thr Lys Trp Lys Met Met Asp Pro Ile
            180                 185                 190

Leu Thr Thr Ser Val Pro Val Tyr Ser Leu Lys Val Asp Lys Glu Tyr
        195                 200                 205

Glu Val Arg Val Arg Ser Lys Gln Arg Asn Ser Gly Asn Tyr Gly Glu
    210                 215                 220

Phe Ser Glu Val Leu Tyr Val Thr Leu Pro Gln Met Ser Gln
225                 230                 235

<210> SEQ ID NO 70
<211> LENGTH: 191
<212> TYPE: PRT
<213> ORGANISM: Homo sapiens

<400> SEQUENCE: 70

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125
```

```
Glu Asp Gly Ser Pro Arg Thr Gly Gln Ile Phe Lys Gln Thr Tyr Ser
            130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 71
<211> LENGTH: 454
<212> TYPE: PRT
<213> ORGANISM: artificial sequence
<220> FEATURE:
<223> OTHER INFORMATION: fusion protein

<400> SEQUENCE: 71

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
            130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Gly
            180                 185                 190

Gly Arg Gly Gly Gly Ser Gly Gly Gly Ser Gly Gly Gly
        195                 200                 205

Ser Gly Gly Gly Ser Glu Phe Phe Ser Gly Ser Glu Ala Thr Ala
    210                 215                 220

Ala Ile Leu Ser Arg Ala Pro Trp Ser Leu Gln Ser Val Asn Pro Gly
225                 230                 235                 240

Leu Lys Thr Asn Ser Ser Lys Glu Pro Lys Phe Thr Lys Cys Arg Ser
                245                 250                 255

Pro Glu Arg Glu Thr Phe Ser Cys His Trp Thr Asp Glu Val His His
            260                 265                 270

Gly Thr Lys Asn Leu Gly Pro Ile Gln Leu Phe Tyr Thr Arg Arg Asn
        275                 280                 285

Thr Gln Glu Trp Thr Gln Glu Trp Lys Glu Cys Pro Asp Tyr Val Ser
    290                 295                 300
```

```
Ala Gly Glu Asn Ser Cys Tyr Phe Asn Ser Ser Phe Thr Ser Ile Trp
305                 310                 315                 320

Ile Pro Tyr Cys Ile Lys Leu Thr Ser Asn Gly Gly Thr Val Asp Glu
            325                 330                 335

Lys Cys Phe Ser Val Asp Glu Ile Val Gln Pro Asp Pro Ile Ala
            340                 345                 350

Leu Asn Trp Thr Leu Leu Asn Val Ser Leu Thr Gly Ile His Ala Asp
            355                 360                 365

Ile Gln Val Arg Trp Glu Ala Pro Arg Asn Ala Asp Ile Gln Lys Gly
            370                 375                 380

Trp Met Val Leu Glu Tyr Glu Leu Gln Tyr Lys Glu Val Asn Glu Thr
385                 390                 395                 400

Lys Trp Lys Met Met Asp Pro Ile Leu Thr Thr Ser Val Pro Val Tyr
            405                 410                 415

Ser Leu Lys Val Asp Lys Glu Tyr Glu Val Arg Val Arg Ser Lys Gln
            420                 425                 430

Arg Asn Ser Gly Asn Tyr Gly Glu Phe Ser Glu Val Leu Tyr Val Thr
            435                 440                 445

Leu Pro Gln Met Ser Gln
            450

<210> SEQ ID NO 72
<211> LENGTH: 454
<212> TYPE: PRT
<213> ORGANISM: artificial sequence
<220> FEATURE:
<223> OTHER INFORMATION: fusion protein

<400> SEQUENCE: 72

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Gly
            180                 185                 190

Gly Gly Gly Ser Gly Gly Gly Gly Ser Gly Gly Gly Gly Ser Gly Gly
            195                 200                 205
```

Gly Gly Ser Gly Gly Gly Ser Phe Ser Gly Ser Glu Ala Thr Ala
    210             215                 220

Ala Ile Leu Ser Arg Ala Pro Trp Ser Leu Gln Ser Val Asn Pro Gly
225             230                 235                 240

Leu Lys Thr Asn Ser Ser Lys Glu Pro Lys Phe Thr Lys Cys Arg Ser
                245                 250                 255

Pro Glu Arg Glu Thr Phe Ser Cys His Trp Thr Asp Glu Val His His
            260                 265                 270

Gly Thr Lys Asn Leu Gly Pro Ile Gln Leu Phe Tyr Thr Arg Arg Asn
        275                 280                 285

Thr Gln Glu Trp Thr Gln Glu Trp Lys Glu Cys Pro Asp Tyr Val Ser
290                 295                 300

Ala Gly Glu Asn Ser Cys Tyr Phe Asn Ser Ser Phe Thr Ser Ile Trp
305                 310                 315                 320

Ile Pro Tyr Cys Ile Lys Leu Thr Ser Asn Gly Gly Thr Val Asp Glu
                325                 330                 335

Lys Cys Phe Ser Val Asp Glu Ile Val Gln Pro Asp Pro Pro Ile Ala
            340                 345                 350

Leu Asn Trp Thr Leu Leu Asn Val Ser Leu Thr Gly Ile His Ala Asp
        355                 360                 365

Ile Gln Val Arg Trp Glu Ala Pro Arg Asn Ala Asp Ile Gln Lys Gly
370                 375                 380

Trp Met Val Leu Glu Tyr Glu Leu Gln Tyr Lys Glu Val Asn Glu Thr
385                 390                 395                 400

Lys Trp Lys Met Met Asp Pro Ile Leu Thr Thr Ser Val Pro Val Tyr
                405                 410                 415

Ser Leu Lys Val Asp Lys Glu Tyr Glu Val Arg Val Arg Ser Lys Gln
            420                 425                 430

Arg Asn Ser Gly Asn Tyr Gly Glu Phe Ser Glu Val Leu Tyr Val Thr
        435                 440                 445

Leu Pro Gln Met Ser Gln
    450

<210> SEQ ID NO 73
<211> LENGTH: 429
<212> TYPE: PRT
<213> ORGANISM: artificial sequence
<220> FEATURE:
<223> OTHER INFORMATION: fusion protein

<400> SEQUENCE: 73

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

```
Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Phe
            180                 185                 190

Ser Gly Ser Glu Ala Thr Ala Ala Ile Leu Ser Arg Ala Pro Trp Ser
        195                 200                 205

Leu Gln Ser Val Asn Pro Gly Leu Lys Thr Asn Ser Ser Lys Glu Pro
        210                 215                 220

Lys Phe Thr Lys Cys Arg Ser Pro Glu Arg Glu Thr Phe Ser Cys His
225                 230                 235                 240

Trp Thr Asp Glu Val His His Gly Thr Lys Asn Leu Gly Pro Ile Gln
                245                 250                 255

Leu Phe Tyr Thr Arg Arg Asn Thr Gln Glu Trp Thr Gln Glu Trp Lys
                260                 265                 270

Glu Cys Pro Asp Tyr Val Ser Ala Gly Glu Asn Ser Cys Tyr Phe Asn
            275                 280                 285

Ser Ser Phe Thr Ser Ile Trp Ile Pro Tyr Cys Ile Lys Leu Thr Ser
        290                 295                 300

Asn Gly Gly Thr Val Asp Glu Lys Cys Phe Ser Val Asp Glu Ile Val
305                 310                 315                 320

Gln Pro Asp Pro Pro Ile Ala Leu Asn Trp Thr Leu Leu Asn Val Ser
                325                 330                 335

Leu Thr Gly Ile His Ala Asp Ile Gln Val Arg Trp Glu Ala Pro Arg
            340                 345                 350

Asn Ala Asp Ile Gln Lys Gly Trp Met Val Leu Glu Tyr Glu Leu Gln
        355                 360                 365

Tyr Lys Glu Val Asn Glu Thr Lys Trp Lys Met Met Asp Pro Ile Leu
    370                 375                 380

Thr Thr Ser Val Pro Val Tyr Ser Leu Lys Val Asp Lys Glu Tyr Glu
385                 390                 395                 400

Val Arg Val Arg Ser Lys Gln Arg Asn Ser Gly Asn Tyr Gly Glu Phe
                405                 410                 415

Ser Glu Val Leu Tyr Val Thr Leu Pro Gln Met Ser Gln
            420                 425
```

GROWTH HORMONE FUSION PROTEINS WITH GROWTH HORMONE RECEPTOR AGONIST ACTIVITY

CROSS REFERENCE TO RELATED APPLICATIONS

This is a Divisional of co-pending U.S. patent application Ser. No. 14/004,684, filed Sep. 12, 2013, which is the US National Stage of International Patent Application No. PCT/GB2012/050550, filed Mar. 14, 2012, which in turn claimed priority to UK Patent Application No. 1104285.0, filed Mar. 15, 2011. The foregoing patent applications are incorporated by reference herein in their entirety.

FIELD

The invention relates to growth hormone fusion proteins comprising modified growth hormone receptor polypeptides that do not bind or show reduced binding to growth hormone; nucleic acid molecules encoding said proteins and methods of treatment that use said proteins.

BACKGROUND

Growth hormone (GH) is an anabolic cytokine hormone important for linear growth in childhood and normal body composition in adults[1]. The current therapeutic regimen for GH replacement requires once-daily subcutaneous injections which is inconvenient and expensive. A number of approaches have been taken to create long-acting preparations, including pegylation[2] and sustained-release formulations[3-5]. Pegylation has the disadvantage that it reduces affinity of hormone for receptor[2], and chemical modification with subsequent purification is expensive. Sustained-release formulations have proven efficacy[4-7] but such GH preparations are characterised by a dominant early-release profile, causing supraphysiological GH levels[3], manufacture is expensive and injections may be painful[4]. There is a need for growth hormone formulations that minimise manufacturing costs, have good pharmacokinetic profiles, are easy to administer, and acceptable to patients.

GH acts through a cell-surface type 1 cytokine receptor (GHR). In common with other cytokine receptors, the extracellular domain of the GHR is proteolytically cleaved and circulates as a binding protein (GHBP)[8]. Under physiological conditions GH is in part bound in the circulation in a 1:1 molar ratio by GHBP and this complex appears to be biologically inactive, protected from clearance and degradation[9,10]. A cross-linked complex of GH with GHBP has delayed clearance but no biological activity[11]. Co-administration of separately purified GHBP with GH in a 1:1 ratio can augment the anabolic actions of GH[12]. Thus, like many hormonal systems, binding in the circulation provides an inactive circulating reservoir in equilibrium with active free hormone[13]. GH binds sequentially with two membrane bound growth hormone receptors (GHR) via two separate sites on GH referred as site 1 and site 2. Site 1 is a high affinity binding site and site 2 a low affinity site. A single GH molecule binds 1 GHR via site 1. A second GHR is then recruited via site 2 to form a GHR:GH:GHR complex. The complex is then internalised and activates a signal transduction cascade leading to changes in gene expression. The extracellular domain of GHR exists as two linked domains each of approximately 100 amino acids (SD-100), the C-terminal SD-100 domain (b) being closest to the cell surface and the N-terminal SD-100 domain (a) being furthest away. It is a conformational change in these two domains that occurs on hormone binding with the formation of the trimeric complex GHR-GH-GHR.

In our co-pending applications WO01/96565, WO2009/013461 and currently unpublished PCT/GB2008/003056 we disclose growth hormone fusion proteins that behave as antagonists and agonists of growth hormone receptor activation. The fusion of native growth hormone and modified growth hormone to the extracellular domain of growth hormone receptor creates fusion proteins that have improved pharmacokinetics and pharmacodynamics with super agonist and antagonist activity.

SUMMARY

This disclosure relates to the modification of the extracellular domain of growth hormone receptor and the fusion of these modified polypeptides to growth hormone and modified growth hormone to create fusion proteins with altered PK and PD and their use in the treatment of diseases that would benefit from enhanced growth hormone activity and also inhibition of growth hormone receptor activation.

DESCRIPTION

According to an aspect of the invention there is provided a fusion protein comprising growth hormone or a modified growth hormone linked either directly or indirectly to a polypeptide comprising the amino acid sequence of a growth hormone receptor polypeptide wherein said receptor polypeptide is modified by addition, deletion or substitution of at least one amino acid residue wherein said receptor polypeptide substantially lacks growth hormone binding activity or has reduced growth hormone binding activity.

In a preferred embodiment of the invention said fusion protein comprises or consists of the extracellular binding domain of growth hormone receptor; preferably human growth hormone receptor.

In a preferred embodiment of the invention the fusion protein is modified in the growth hormone binding domain of said extracellular binding domain.

In a preferred embodiment of the invention said modification is one or more of the amino acid sequences selected from the group consisting of: W169, R43, E44, I103, W104, I105, P106, I164 and D165 as represented in FIG. 1a (SEQ ID NO: 1).

In a preferred embodiment of the invention said modification comprises or consists of deletion of amino acid residue tryptophan 104 of the amino acid sequence represented in FIG. 1a (SEQ ID NO: 1).

In a preferred embodiment of the invention said amino acid residue tryptophan 104 is substituted for one or more amino acid residues; preferably tryptophan 104 is substituted.

In an alternative preferred embodiment of the invention said modification comprises modification of amino acid residues 125-131 of the amino acid sequence in FIG. 1a (SEQ ID NO: 1). Preferably said modification is the deletion of all or part of amino acid residues 125-131.

In a preferred embodiment of the invention said fusion protein is an agonist. Preferably said fusion protein comprises the amino acid sequence represented in FIG. 2 (SEQ ID NO: 3).

In an alternative preferred embodiment of the invention said fusion protein is an antagonist.

In a preferred embodiment of the invention said fusion protein comprises at least one site 2 modification to growth hormone.

In a further preferred embodiment of the invention said fusion protein comprises at least one site 1 modification to growth hormone.

In an alternative preferred embodiment of the invention said fusion protein comprises a site 2 and site 1 modification.

In a preferred embodiment of the invention said fusion protein comprises growth hormone modified at amino acid residue glycine 120 of the amino acid sequence represented in FIG. 2 (SEQ ID NO: 3).

Preferably, the modification is substitution of glycine 120 with arginine; alanine; lysine; tryptophan; tyrosine; phenylalanine; or glutamic acid.

In a preferred embodiment of the invention said modification is substitution of glycine 120 for arginine or lysine or alanine In a preferred embodiment of the invention said modification is substitution of glycine 120 for arginine.

Preferably said fusion protein comprises the amino acid sequence modifications: histidine 18 with aspartic acid, histidine 21 with asparagine, glycine 120 with arginine, arginine 167 with asparagine, lysine 168 with alanine, aspartic acid 171 with serine, lysine 172 with arginine, glutamic acid 174 with serine and isoleucine 179 with threonine.

In a preferred embodiment of the invention said growth hormone or modified growth hormone is linked to said receptor polypeptide by a peptide linker; preferably a flexible peptide linker.

In a preferred embodiment of the invention said peptide linking molecule comprises at least one copy of the peptide Gly Gly Gly Gly Ser (SEQ ID NO: 35).

In a preferred embodiment of the invention said peptide linking molecule comprises 2, 3, 4, 5, 6 or 7 copies of the peptide Gly Gly Gly Gly Ser (SEQ ID NO: 35).

In an alternative preferred embodiment of the invention said peptide linker is modified to include at least one motif for the addition of at least one sugar moiety; preferably said motif comprises Asn-Xaa-Ser or Asn-Xaa-Thr.

In a preferred embodiment of the invention said peptide linker molecule comprises at least one copy of the motif ($Xaa_1$ $Xaa_2$ $Xaa_3$ $Xaa_4$ $Xaa_5$) wherein said motif comprises the glycosylation motif Asn-Xaa-Ser or Asn-Xaa-Thr (SEQ ID NO: 36).

In a preferred embodiment of the invention said peptide linker comprises at least one copy of an amino acid motif selected from the group consisting of:

$Asn_1$-$Xaa_2$-$Ser_3$ $Xaa_4$ $Xaa_5$ wherein $Xaa_2$ is any amino acid except proline (SEQ ID NO: 37);

$Xaa_1$ $Asn_2$-$Xaa_3$-$Ser_4$ $Xaa_5$ wherein $Xaa_3$ is any amino acid except proline (SEQ ID NO: 38);

$Xaa_1$ $Xaa_2$ $Asn_3$-$Xaa_4$-$Ser_5$ wherein $Xaa_4$ is any amino acid except proline (SEQ ID NO: 39);

$Asn_1$-$Xaa_2$-$Thr_3$ $Xaa_4$ $Xaa_5$ wherein $Xaa_2$ is any amino acid except proline (SEQ ID NO: 40);

$Xaa_1$ $Asn_2$-$Xaa_3$-$Thr_4$ $Xaa_5$ wherein $Xaa_3$ is any amino acid except proline (SEQ ID NO: 41); and $Xaa_1$ $Xaa_2$ $Asn_3$-$Xaa_4$-$Thr_5$wherein $Xaa_4$ is any amino acid except proline (SEQ ID NO: 42).

Preferably said peptide linker comprises at least one copy of a motif selected from the group consisting of:

$Asn_1$-$Xaa_2$-$Ser_3$ $Gly_4$ $Ser_5$ wherein $Xaa_2$ is any amino acid except proline (SEQ ID NO: 43);

$Gly_1$ $Asn_2$-$Xaa_3$-Ser4 $Ser_5$ wherein $Xaa_3$ is any amino acid except proline (SEQ ID NO: 44);

$Gly_1$ $Gly_2$ $Asn_3$-$Xaa_4$-$Ser_5$ wherein $Xaa_4$ is any amino acid except proline (SEQ ID NO: 45);

$Asn_1$-$Xaa_2$-$Thr_3$ $Gly_4$ $Ser_5$ wherein $Xaa_2$ is any amino acid except proline (SEQ ID NO: 46);

$Gly_1$ $Asn_2$-$Xaa_3$-$Thr_4$ $Ser_5$ wherein $Xaa_3$ is any amino acid except proline (SEQ ID NO: 47); and Glp $Gly_2$ $Asn_3$-$Xaa_4$-$Thr_5$wherein $Xaa_4$ is any amino acid except proline (SEQ ID NO: 48).

In an alternative preferred embodiment of the invention said peptide linker comprises at least one copy of a motif selected from the group consisting of:

$Asn_1$-$Xaa_2$-$Ser_3$ $Ser_4$ $Gly_5$ wherein $Xaa_2$ is any amino acid except proline (SEQ ID NO: 49);

$Ser_1$ $Asn_2$-$Xaa_3$-$Ser_4$ $Gly_5$ wherein $Xaa_3$ is any amino acid except proline (SEQ ID NO: 50);

$Ser_1$ $Ser_2$ $Asn_3$-$Xaa_4$-$Ser_5$ wherein $Xaa_4$ is any amino acid except proline (SEQ ID NO: 51);

$Asn_1$-$Xaa_2$-$Thr_3$ $Ser_4$ $Gly_5$ wherein $Xaa_2$ is any amino acid except proline (SEQ ID NO: 52);

$Ser_1$ $Asn_2$-$Xaa_3$-$Thr_4$ $Gly_5$ wherein $Xaa_3$ is any amino acid except proline (SEQ ID NO: 53); and $Ser_1$ $Ser_2$ $Asn_3$-$Xaa_4$-$Thr_5$ wherein $Xaa_a$ is any amino acid except proline (SEQ ID NO: 54).

In a preferred embodiment of the invention said peptide linker molecule comprises at least one copy of the motif ($Xaa_1$ $Xaa_2$ $Xaa_3$ $Xaa_4$ $Xaa_5$) wherein said motif comprises the glycosylation motif Asn-Xaa-Ser or Asn-Xaa-Thr and at least one copy of the motif (Gly Gly Gly Gly Ser) (SEQ ID NO: 35) wherein said peptide linker is 5-50 amino acids.

In a preferred embodiment of the invention said peptide linker comprises at least one copy of the motif ($Xaa_1$ $Xaa_2$ $Xaa_3$ $Xaa_4$ $Xaa_5$) wherein said motif comprises the glycosylation motif Asn-Xaa-Ser or Asn-Xaa-Thr and a copy of the motif (Ser Ser Ser Ser Gly) (SEQ ID NO: 55) wherein said peptide linker is 5-50 amino acids.

In a preferred embodiment of the invention said fusion polypeptide linker is modified by the addition of at least one sugar selected from the group consisting of: mannose, galactose, N-acetyl glucosamine, N-acetyl neuraminic acid, N-glycolyl neuraminic acid, N-acetyl galactosamine, fucose, glucose, rhamnose, xylose, or combinations of sugars, for example in an oligosacharide or scaffolded system.

Suitable carbohydrate moieties include monosaccharides, oligosaccharides and polysaccharides, and include any carbohydrate moiety that is present in naturally occurring glycoproteins or in biological systems. For example, optionally protected glycosyl or glycoside derivatives, for example optionally-protected glucosyl, glucoside, galactosyl or galactoside derivatives. Glycosyl and glycoside groups include both α and β groups. Suitable carbohydrate moieties include glucose, galactose, fucose, GlcNAc, GalNAc, sialic acid, and mannose, and oligosaccharides or polysaccharides comprising at least one glucose, galactose, fucose, GlcNAc, GalNAc, sialic acid, and/or mannose residue.

Any functional groups in the carbohydrate moiety may optionally be protected using protecting groups known in the art (see for example Greene et al, "Protecting groups in organic synthesis", 2nd Edition, Wiley, New York, 1991, the disclosure of which is hereby incorporated by reference). Suitable protecting groups for any —OH groups in the carbohydrate moiety include acetate (Ac), benzyl (Bn), silyl (for example tert-butyl dimethylsilyl (TBDMSi) and tert-butyldiphenylsilyl (TMDPSi)), acetals, ketals, and methoxymethyl (MOM). Any protecting groups may be removed before or after attachment of the carbohydrate moiety to the peptide linker.

In a preferred embodiment of the invention said sugars are unprotected.

Particularly preferred carbohydrate moieties include Glc (Ac)₄β-, Glc(Bn)₄β-, Gal(Ac)₄β-, Gal(Bn)₄β-, Glc(Ac)₄α(1, 4)Glc(Ac)₃α(1,4)Glc(Ac)₄β-, β-Glc, β-Gal, -Et-β-Gal, -Et-β-Glc, Et-α-Glc, -Et-α-Man, -Et-Lac, -β-Glc(Ac)₂, -β-Glc (Ac)₃, -Et-α-Glc(Ac)₂, -Et-α-Glc(Ac)₃, -Et-α-Glc(Ac)₄, -Et-β-Glc(Ac)₂, -Et-β-Glc(Ac)₃, -Et-β-Glc(Ac)₄, -Et-α-Man (Ac)₃, -Et-α-Man(Ac)₄, -Et-β-Gal(Ac)₃, -Et-β-Gal(Ac)₄, -Et-Lac(Ac)₅, -Et-Lac(Ac)₆, -Et-Lac(Ac)₇, and their deprotected equivalents.

Preferably, any saccharide units making up the carbohydrate moiety which are derived from naturally occurring sugars will each be in the naturally occurring enantiomeric form, which may be either the D-form (e.g. D-glucose or D-galactose), or the L-form (e.g. L-rhamnose or L-fucose). Any anomeric linkages may be α- or β-linkages.

In a still further alternative embodiment of the invention said fusion protein does not comprise a peptide linking molecule and is a direct fusion of growth hormone or modified growth hormone and the receptor polypeptide According to a further aspect of the invention there is provided a fusion protein comprising the amino acid sequence as represented in FIG. 3 (SEQ ID NO: 4) wherein said amino acid sequence is modified by substitution at amino acid residue tryptophan 346.

According to a further aspect of the invention there is provided a fusion protein comprising the amino acid sequence as represented in FIG. 4 (SEQ ID NO: 5) wherein said amino acid sequence is modified by substitution at amino acid residue tryptophan 346.

According to a further aspect of the invention there is provided a fusion protein comprising the amino acid sequence as represented in FIG. 5 (SEQ ID NO: 6) wherein said amino acid sequence is modified by substitution at amino acid residue tryptophan 321.

According to a further aspect of the invention there is provided a fusion protein comprising the amino acid sequence as represented in FIG. 6 (SEQ ID NO: 7) wherein said amino acid sequence is modified by substitution at amino acid residue tryptophan 346.

According to a further aspect of the invention there is provided a fusion protein comprising the amino acid sequence as represented in FIG. 7 (SEQ ID NO: 8) wherein said amino acid sequence is modified by substitution at amino acid residue tryptophan 346.

According to a further aspect of the invention there is provided a fusion protein comprising the amino acid sequence as represented in FIG. 8 (SEQ ID NO: 9) wherein said amino acid sequence is modified by substitution at amino acid residue tryptophan 321.

According to a further aspect of the invention there is provided a fusion protein comprising the amino acid sequence as represented in FIG. 9 (SEQ ID NO: 10) wherein said amino acid sequence is modified by substitution at amino acid residue tryptophan 346.

According to a further aspect of the invention there is provided a fusion protein comprising the amino acid sequence as represented in FIG. 10 (SEQ ID NO: 11) wherein said amino acid sequence is modified by substitution at amino acid residue tryptophan 346.

According to a further aspect of the invention there is provided a fusion protein comprising the amino acid sequence as represented in FIG. 11 (SEQ ID NO: 12) wherein said amino acid sequence is modified by substitution at amino acid residue tryptophan 321.

According to a further aspect of the invention there is provided a fusion protein comprising the amino acid sequence as represented in FIG. 12 (SEQ ID NO: 13) wherein said amino acid sequence is modified by substitution at amino acid residue tryptophan 346.

According to a further aspect of the invention there is provided a fusion protein comprising the amino acid sequence as represented in FIG. 13 (SEQ ID NO: 14) wherein said amino acid sequence is modified by substitution at amino acid residue tryptophan 346.

According to a further aspect of the invention there is provided a fusion protein comprising the amino acid sequence as represented in FIG. 14 (SEQ ID NO: 15) wherein said amino acid sequence is modified by substitution at amino acid residue tryptophan 346.

According to a further aspect of the invention there is provided a fusion protein comprising the amino acid sequence as represented in FIG. 15 (SEQ ID NO: 16) wherein said amino acid sequence is modified by substitution at amino acid residue tryptophan 346.

According to a further aspect of the invention there is provided a fusion protein comprising the amino acid sequence as represented in FIG. 16 (SEQ ID NO: 17) wherein said amino acid sequence is modified by substitution at amino acid residue tryptophan 346.

According to a further aspect of the invention there is provided a fusion protein comprising the amino acid sequence as represented in FIG. 17 (SEQ ID NO: 18) wherein said amino acid sequence is modified by substitution at amino acid residue tryptophan 346.

According to a further aspect of the invention there is provided a fusion protein comprising the amino acid sequence as represented in FIG. 18 (SEQ ID NO: 19) wherein said amino acid sequence is modified by substitution at amino acid residue tryptophan 349.

According to a further aspect of the invention there is provided a fusion protein comprising the amino acid sequence as represented in FIG. 19 (SEQ ID NO: 20) wherein said amino acid sequence is modified by substitution at amino acid residue tryptophan 346.

According to a further aspect of the invention there is provided a fusion protein comprising the amino acid sequence as represented in FIG. 20 (SEQ ID NO: 21) wherein said amino acid sequence is modified by substitution at amino acid residue tryptophan 346.

According to a further aspect of the invention there is provided a fusion protein comprising the amino acid sequence as represented in FIG. 21 (SEQ ID NO: 22) wherein said amino acid sequence is modified by substitution at amino acid residue tryptophan 346.

According to a further aspect of the invention there is provided a fusion protein comprising the amino acid sequence as represented in FIG. 22 (SEQ ID NO: 23) wherein said amino acid sequence is modified by substitution at amino acid residue tryptophan 346.

According to a further aspect of the invention there is provided a fusion protein comprising the amino acid sequence as represented in FIG. 23 (SEQ ID NO: 24) wherein said amino acid sequence is modified by substitution at amino acid residue tryptophan 346.

According to a further aspect of the invention there is provided a fusion protein comprising the amino acid sequence as represented in FIG. 24 (SEQ ID NO: 25) wherein said amino acid sequence is modified by substitution at amino acid residue tryptophan 346.

According to a further aspect of the invention there is provided a fusion protein comprising the amino acid sequence as represented in FIG. 25 (SEQ ID NO: 26) wherein said amino acid sequence is modified by substitution at amino acid residue tryptophan 346.

According to a further aspect of the invention there is provided a fusion protein comprising the amino acid sequence as represented in FIG. 26 (SEQ ID NO: 27) wherein said amino acid sequence is modified by substitution at amino acid residue tryptophan 346.

According to a further aspect of the invention there is provided a fusion protein comprising the amino acid sequence as represented in FIG. 27 (SEQ ID NO: 28) wherein said amino acid sequence is modified by substitution at amino acid residue tryptophan 346.

According to a further aspect of the invention there is provided a fusion protein comprising the amino acid sequence as represented in FIG. 28 (SEQ ID NO: 29) wherein said amino acid sequence is modified by substitution at amino acid residue tryptophan 349.

According to a further aspect of the invention there is provided a fusion protein comprising the amino acid sequence as represented in FIG. 29 (SEQ ID NO: 30) wherein said amino acid sequence is modified by substitution at amino acid residue tryptophan 349.

According to a further aspect of the invention there is provided a fusion protein comprising the amino acid sequence as represented in FIG. 30 (SEQ ID NO: 31) wherein said amino acid sequence is modified by substitution at amino acid residue tryptophan 349.

According to a further aspect of the invention there is provided a fusion protein comprising the amino acid sequence as represented in FIG. 31 (SEQ ID NO: 32) wherein said amino acid sequence is modified by substitution at amino acid residue tryptophan 349.

In a preferred embodiment of the invention tryptophan is substituted for alanine.

According to an aspect of the invention there is provided a nucleic acid molecule that encodes a fusion polypeptide according to the invention or a nucleic acid molecule that hybridizes to said nucleic acid molecule and encodes a polypeptide wherein said polypeptide has growth hormone receptor agonist or antagonist activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (allows sequences that share at least 90% identity to hybridize)
Hybridization: 5×SSC at 65° C. for 16 hours
Wash twice: 2×SSC at room temperature (RT) for 15 minutes each
Wash twice: 0.5×SSC at 65° C. for 20 minutes each High Stringency (allows sequences that share at least 80% identity to hybridize)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each Low Stringency (allows sequences that share at least 50% identity to hybridize)
Hybridization: 6×SSC at RT to 55° C. for 16-20 hours
Wash at least twice: 2×-3×SSC at RT to 55° C. for 20-30 minutes each.

According to a further aspect of the invention there is provided a vector comprising a nucleic acid molecule according to the invention.

In a preferred embodiment of the invention said vector is an expression vector adapted to express the nucleic acid molecule according to the invention.

A vector including nucleic acid (s) according to the invention need not include a promoter or other regulatory sequence, particularly if the vector is to be used to introduce the nucleic acid into cells for recombination into the genome for stable transfection. Preferably the nucleic acid in the vector is operably linked to an appropriate promoter or other regulatory elements for transcription in a host cell. The vector may be a bi-functional expression vector which functions in multiple hosts. By "promoter" is meant a nucleotide sequence upstream from the transcriptional initiation site and which contains all the regulatory regions required for transcription. Suitable promoters include constitutive, tissue-specific, inducible, developmental or other promoters for expression in eukaryotic or prokaryotic cells. "Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment the promoter is a constitutive, an inducible or regulatable promoter.

According to a further aspect of the invention there is provided a cell transfected or transformed with a nucleic acid molecule or vector according to the invention.

Preferably said cell is a eukaryotic cell. Alternatively said cell is a prokaryotic cell.

In a preferred embodiment of the invention said cell is selected from the group consisting of; a fungal cell (e.g. *Pichia* spp, *Saccharomyces* spp, *Neurospora* spp); insect cell (e.g. *Spodoptera* spp); a mammalian cell (e.g. COS cell, CHO cell); a plant cell.

In a preferred embodiment of the invention said cell is stably transfected. In an alternative preferred embodiment of the invention said cell is transiently transfected.

According to a further aspect of the invention there is provided a pharmaceutical composition comprising a polypeptide according to the invention including an excipient or carrier.

In a preferred embodiment of the invention said pharmaceutical composition is combined with a further therapeutic agent.

When administered the pharmaceutical composition of the present invention is administered in pharmaceutically acceptable preparations. Such preparations may routinely contain pharmaceutically acceptable concentrations of salt, buffering agents, preservatives, compatible carriers, and optionally other therapeutic agents for example chemotherapeutic agents.

The pharmaceutical compositions of the invention can be administered by any conventional route, including injection. The administration and application may, for example, be oral, intravenous, intraperitoneal, intramuscular, intracavity, intra-articuar, subcutaneous, topical (eyes), dermal (e.g a cream lipid soluble insert into skin or mucus membrane), transdermal, or intranasal.

Pharmaceutical compositions of the invention are administered in effective amounts. An "effective amount" is that amount of pharmaceuticals/compositions that alone, or together with further doses or synergistic drugs, produces the desired response. This may involve only slowing the progression of the disease temporarily, although more preferably, it involves halting the progression of the disease permanently. This can be monitored by routine methods or can be monitored according to diagnostic methods.

The doses of the pharmaceuticals compositions administered to a subject can be chosen in accordance with different parameters, in particular in accordance with the mode of administration used and the state of the subject (i.e. age, sex). When administered, the pharmaceutical compositions of the invention are applied in pharmaceutically-acceptable amounts and in pharmaceutically-acceptable compositions. When used in medicine salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceutical compositions may be combined, if desired, with a pharmaceutically-acceptable carrier. The term "pharmaceutically-acceptable carrier" as used herein means one or more compatible solid or liquid fillers, diluents or encapsulating substances that are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction that would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion.

Compositions suitable for parenteral administration conveniently comprise a sterile aqueous or non-aqueous preparation that is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

According to a further aspect of the invention there is provided a method to treat a human subject suffering from growth hormone deficiency comprising administering an effective amount of at least one polypeptide according to the invention.

In a preferred method of the invention said growth hormone deficiency is childhood growth hormone deficiency.

In a preferred method of the invention said growth hormone deficiency is adult growth hormone deficiency.

The treatment of growth hormone deficiency includes for example the treatment of Turners Syndrome, Prader Willi Syndrome, Interuterine growth retardation, idiopathic short stature, renal failure, catabolic states for example during chemotherapy treatment and in the treatment of AIDS.

According to a further aspect of the invention there is provided a method to treat a human subject suffering from growth hormone excess comprising administering an effective amount of at least one polypeptide according to the invention.

In a preferred method of the invention said growth hormone excess results in gigantism.

In a preferred method of the invention said growth hormone excess results in acromegaly.

According to a further aspect of the invention there is provided a method to treat a human subject suffering from cancer comprising administering an effective amount of at least one polypeptide according to the invention.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumours composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In a preferred method of the invention said cancer is prostate cancer.

In a preferred method of the invention said polypeptide is administered intravenously.

In an alternative preferred method of the invention said polypeptide is administered subcutaneously.

In a further preferred method of the invention said polypeptide is administered daily or at two day intervals; preferably said polypeptide is administered at weekly, 2 weekly or monthly intervals.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE FIGURES

An embodiment of the invention will now be described by example only and with reference to the following figures:

FIG. 1a is the amino acid sequence of human growth hormone receptor extracellular domain (SEQ ID NO: 1); The amino acid sequence of human growth hormone receptor extracellular domain without the signal sequence indicated in the figure is set forth as SEQ ID NO: 69. FIG. 1b (SEQ ID NO: 2) is the amino acid sequence of human growth hormone receptor extracellular domain with a tryptophan 104 to alanine substitution; signal sequence is shown in bold and is optional;

FIG. 2 (SEQ ID NO: 3) is the amino acid sequence of human growth hormone; signal sequence is shown in bold and is optional The amino acid sequence of human growth hormone without the signal sequence indicated in the figure is set forth as SEQ ID NO: 70;

FIG. 3 (SEQ ID NO: 4) is the amino acid sequence of growth hormone fusion protein 1B7-V1; signal sequence is shown in bold and is optional. The corresponding amino acid sequence without the signal sequence is set forth herein as SEQ ID NO: 71;

FIG. 4 (SEQ ID NO: 5) is the amino acid sequence of growth hormone fusion protein 1B7-V2; signal sequence is shown in bold and is optional. The corresponding amino acid sequence without the signal sequence is set forth herein as SEQ ID NO: 72;

FIG. 5 (SEQ ID NO: 6) is the amino acid sequence of growth hormone fusion protein 1B7-V3; signal sequence is shown in bold and is optional. The corresponding amino acid sequence without the signal sequence is set forth herein as SEQ ID NO: 73;

FIG. 6 (SEQ ID NO: 7) is the amino acid sequence of growth hormone fusion protein 1B8-V1; signal sequence is shown in bold and is optional;

FIG. 7 (SEQ ID NO: 8) is the amino acid sequence of growth hormone fusion protein 1B8-V2; signal sequence is shown in bold and is optional;

FIG. 8 (SEQ ID NO: 9) is the amino acid sequence of growth hormone fusion protein 1B8-V3; signal sequence is shown in bold and is optional;

FIG. 9 (SEQ ID NO: 10) is the amino acid sequence of growth hormone fusion protein 1B9-V1; signal sequence is shown in bold and is optional;

FIG. 10 (SEQ ID NO: 11) is the amino acid sequence of growth hormone fusion protein 1B9-V2; signal sequence is shown in bold and is optional;

FIG. 11 (SEQ ID NO: 12) is the amino acid sequence of growth hormone fusion protein 1B9-V3; signal sequence is shown in bold and is optional;

FIG. 12 (SEQ ID NO: 13) is the amino acid sequence of growth hormone fusion protein 1B7-G1-V1; signal sequence is shown in bold and is optional;

FIG. 13 (SEQ ID NO: 14) is the amino acid sequence of growth hormone fusion protein 1B7-G1-V2; signal sequence is shown in bold and is optional;

FIG. 14 (SEQ ID NO: 15) is the amino acid sequence of growth hormone fusion protein 1B7-G2-V1; signal sequence is shown in bold and is optional;

FIG. 15 (SEQ ID NO: 16) is the amino acid sequence of growth hormone fusion protein 1B7-G2-V2; signal sequence is shown in bold and is optional;

FIG. 16 (SEQ ID NO: 17) is the amino acid sequence of growth hormone fusion protein 1B7-G3-V1; signal sequence is shown in bold and is optional;

FIG. 17 (SEQ ID NO: 18) is the amino acid sequence of growth hormone fusion protein 1B7-G3-V2; signal sequence is shown in bold and is optional;

FIG. 18 (SEQ ID NO: 19) is the amino acid sequence of growth hormone fusion protein 1B7-G4-V1; signal sequence is shown in bold and is optional;

FIG. 19 (SEQ ID NO: 20) is the amino acid sequence of growth hormone fusion protein 1B7-G4-V2; signal sequence is shown in bold and is optional;

FIG. 20 (SEQ ID NO: 21) is the amino acid sequence of growth hormone fusion protein 1B8-G1-V1; signal sequence is shown in bold and is optional;

FIG. 21 (SEQ ID NO: 22) is the amino acid sequence of growth hormone fusion protein 1B8-G1-V2; signal sequence is shown in bold and is optional;

FIG. 22 (SEQ ID NO: 23) is the amino acid sequence of growth hormone fusion protein 1B9-G1-V1; signal sequence is shown in bold and is optional;

FIG. 23 (SEQ ID NO: 24) is the amino acid sequence of growth hormone fusion protein 1B9-G1-V2; signal sequence is shown in bold and is optional;

FIG. 24 (SEQ ID NO: 25) is the amino acid sequence of growth hormone fusion protein 1B8-G3-V1; signal sequence is shown in bold and is optional;

FIG. 25 (SEQ ID NO: 26) is the amino acid sequence of growth hormone fusion protein 1B8-G3-V2; signal sequence is shown in bold and is optional;

FIG. 26 (SEQ ID NO: 27) is the amino acid sequence of growth hormone fusion protein 1B9-G3-V1; signal sequence is shown in bold and is optional;

FIG. 27 (SEQ ID NO: 28) is the amino acid sequence of growth hormone fusion protein 1B9-G3-V2; signal sequence is shown in bold and is optional;

FIG. 28 (SEQ ID NO: 29) is the amino acid sequence of growth hormone fusion protein 1B8-G4-V1; signal sequence is shown in bold and is optional;

FIG. 29 (SEQ ID NO: 30) is the amino acid sequence of growth hormone fusion protein 1B8-G4-V2; signal sequence is shown in bold and is optional;

FIG. 30 (SEQ ID NO: 31) is the amino acid sequence of growth hormone fusion protein 1B9-G4-V1; signal sequence is shown in bold and is optional; and FIG. 31 (SEQ ID NO: 32) is the amino acid sequence of growth hormone fusion protein 1B9-G4-V2; signal sequence is shown in bold and is optional.

BRIEF DESCRIPTION OF THE DESCRIBED SEQUENCES

Figure 32:
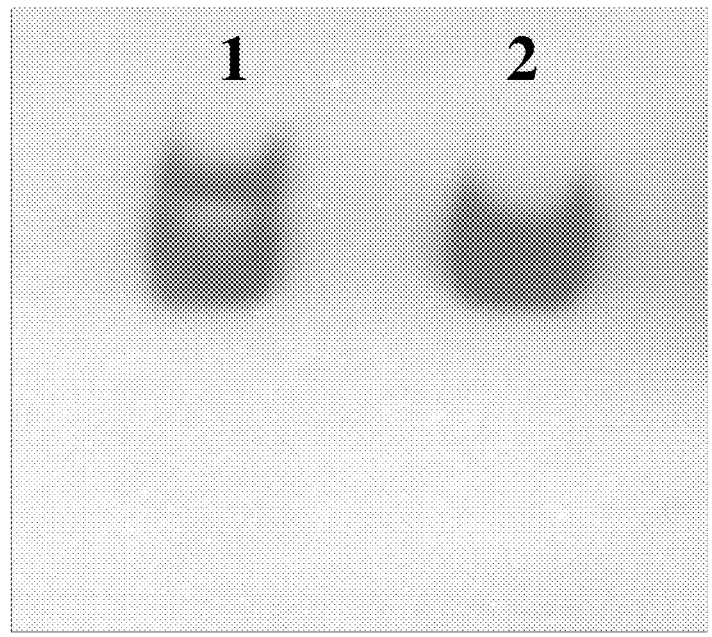
FIG. 32 western blot of native PAGE gel showing the separation of 1B7v2_wildtype, (Lane 1) and 1B7v2_W104 mutant (Lane 2). The image shows that the inclusion of the mutation, W104A in the GHR moiety in 1B7v2_W104 prevents formation of what is thought to be a dimer between 1B7v2 molecules: formation of this dimer is thought to be primarily the results of intermolecular association of GH with GHR.
Figure 33:
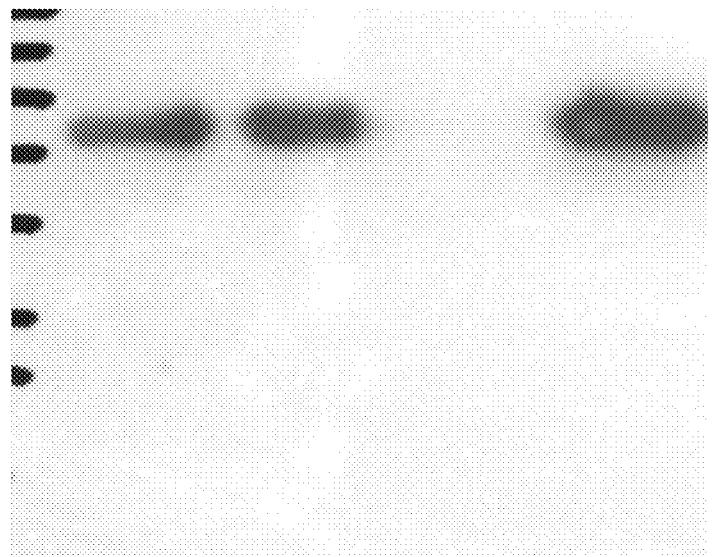
FIG. 33: western blot of SDS-PAGE gel showing separation of 1B7v2_W104A; transfection 1 (lane 1), 1B7v2_W104A; transfection 2, (lane 2) and 1B7v2_wild type (lane 3). Both molecules are detected at around 75 kDa.
Figure 34:
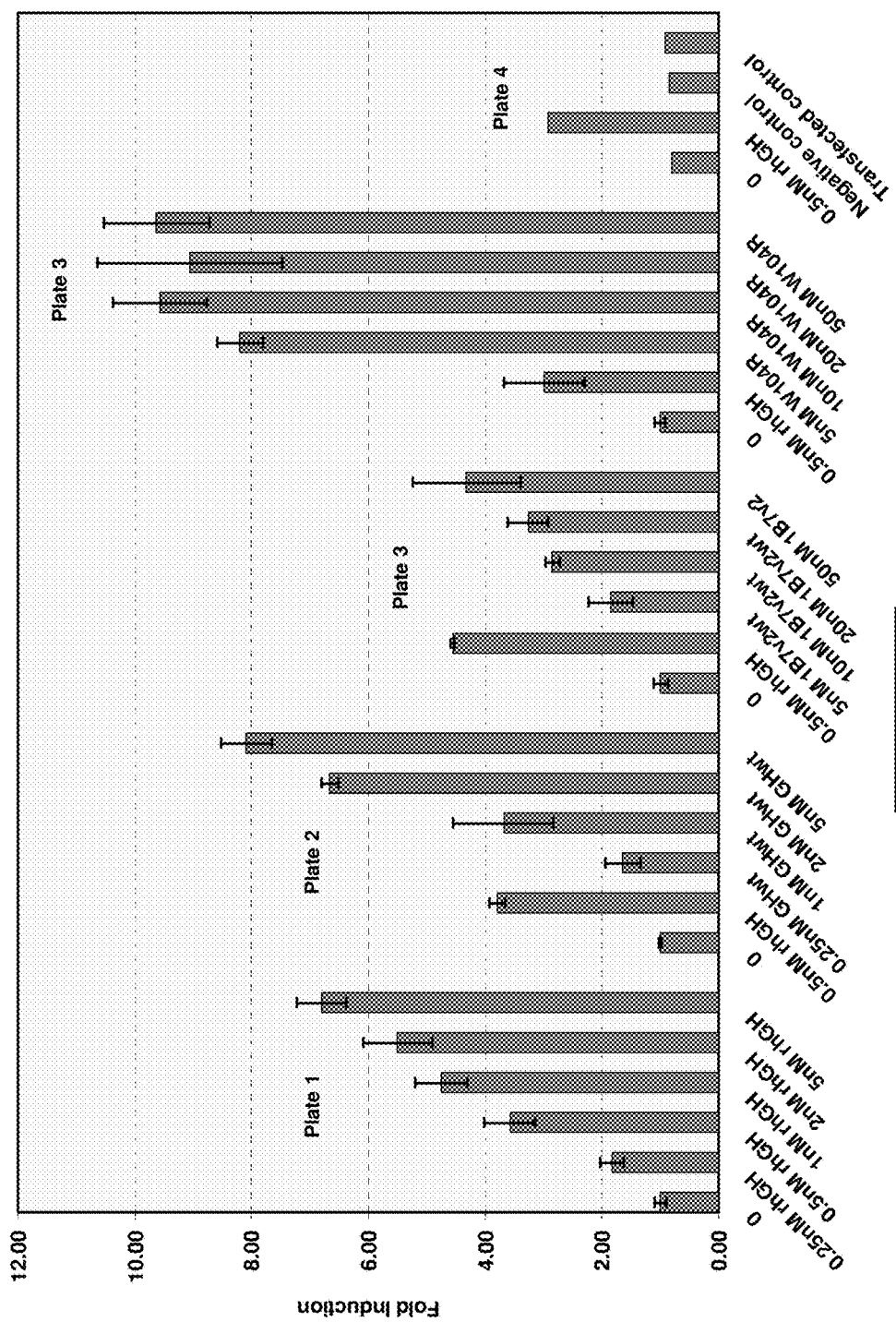
FIG. 34: Corrected luciferase data from a dual luciferase bioassay performed in 293 Hi cells shows increased bioactivity for 1B7V2_Hist_W104 mutant compared to the non-mutant 1B7V2_Hist. This shows that inclusion of the mutant may indeed increase bioactivity of the 1B7V2 molecule.
Figure 35:
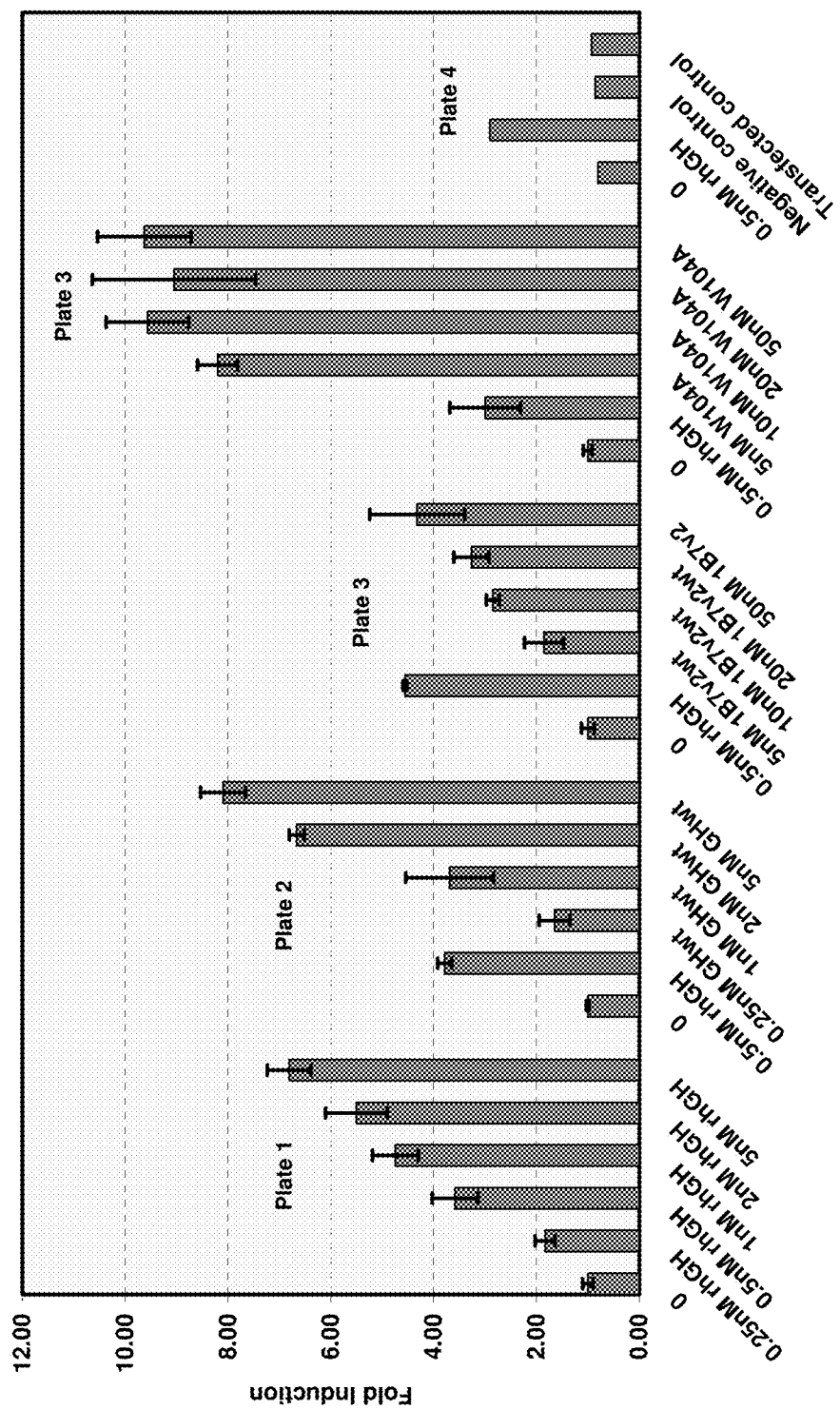
FIG. 35 plate 1: rhGH standard curve; plate 2: media from stable GHwt transfected cells; plate 3: media from stable 1B7v2_wt transfected cells; plate 4: media from stable 1B7v2_W104A transfected cells; plate 5: control media samples.
Figure 36:
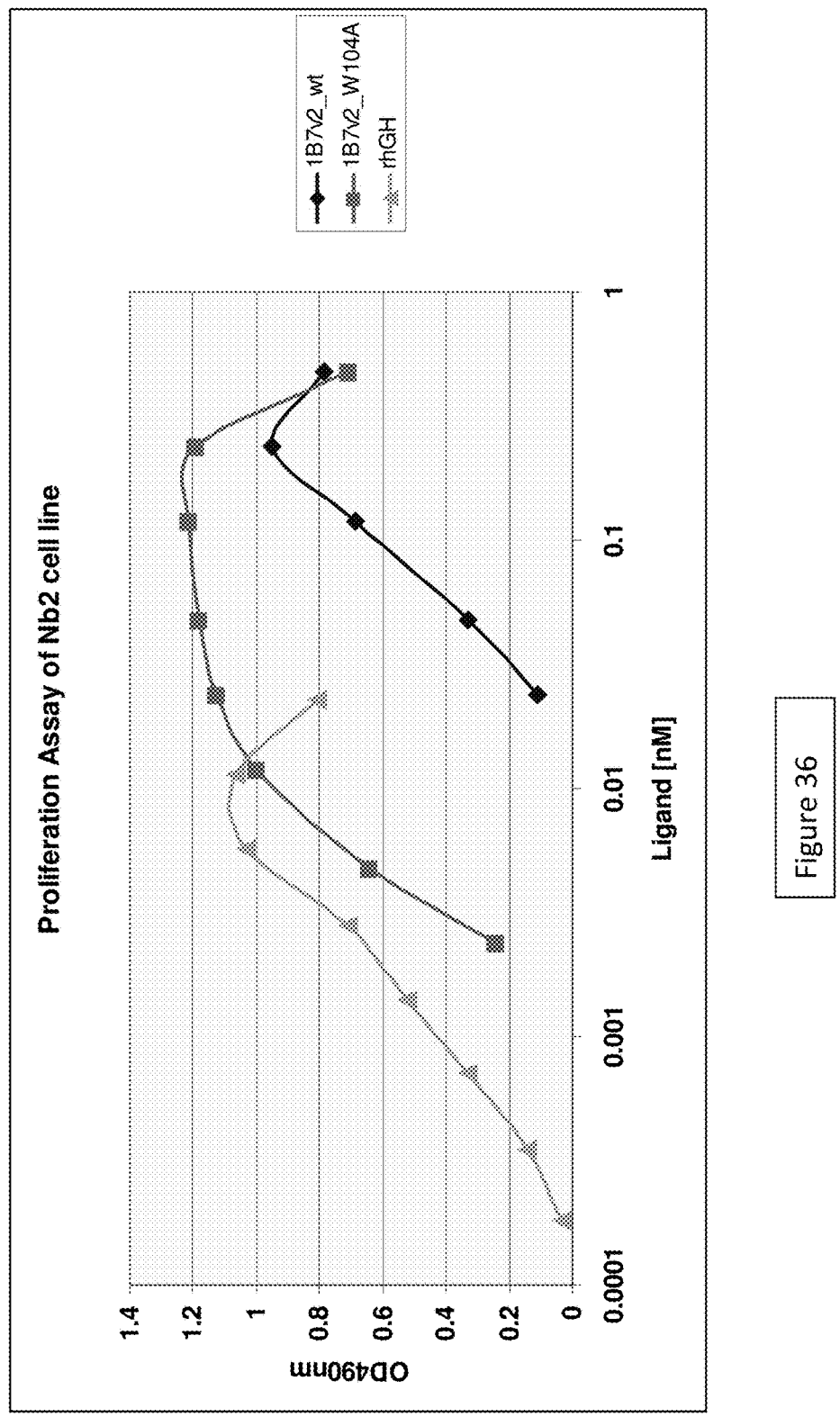
FIG. 36 illustrates the stimulation of proliferation of Nb2 cells by 1B7v2_W104A mutant compared to recombinant human growth hormone and 1B7v2_wt.

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 96064_301_1001 seq.txt, created Oct. 2, 2016, about 164 KB, which is incorporated by reference herein.

EXAMPLES

Materials and Methods

All the materials were purchased from Sigma (Poole, UK) unless otherwise stated. Recombinant GH was purchased from Pfizer, recombinant *E. coli* derived human GH binding protein used in binding assays was a gift from DSL (DSL Research Reagents, Oxfordshire, UK), and iodinated GH a gift from NovoNordisk (NovoNordisk Park, Denmark). GH and GHR mAbs used for purification and characterisation were in-house materials.

Construction Expression and Testing of 1B7v2/v3 Molecules Containing a Tryptophan-104 (W104) to Alanine (A104) Substitution Stage 1: Construction of 1B7v2/v3_Hist Molecules 1. Digest pGHsecTag-1B7v0-Hist using the restriction enzymes EcoRV and AgeI (see FIG. 2.1 (SEQ ID NO: 56) sequence). This molecule contains a histidine tag at the C-terminal and therefore does NOT have a stop codon in this region (see FIG. 2.2 (SEQ ID NO: 57) for sequence)
2. Take pGHsecTag-1B7v2 and v3 molecules (These molecules contain a STOP codon prior to the Hist tag and therefore are not Hist tagged, see FIG. 1.4). Replacing the EcoRV/AgeI sequence in this molecule with the sequence from pGHsecTag-1B7v0-Hist (FIG. 2.2 (SEQ ID NO: 57)) will allow read through to the Hist-tag.

FIG. 2.1: pGHsecTag-1B7v0-Hist (SEQ ID NO: 56)
EcoRV and AgeI sites shown in red. Hist tag shown in italics and underlined. Linker in bold. Signal sequence underlined

```
GCTAGCCACCATGGCTACAGGCTCCCGGACGTCCCTGCTCCTGGCTTTTG

GCCTGCTCTGCCTGCCCTGGCTTCAAGAGGGCAGTGCCTTCCCAACCATT

CCCTTATCCAGGCTTTTTGACAACGCTAGTCTCCGCGCCCATCGTCTGCA

CCAGCTGGCCTTTGACACCTACCAGGAGTTTGAAGAAGCCTATATCCCAA

AGGAACAGAAGTATTCATTCCTGCAGAACCCCCAGACCTCCCTCTGTTTC

TCAGAGTCTATTCCGACACCCTCCAACAGGGAGGAAACACAACAGAAATC

CAACCTAGAGCTGCTCCGCATCTCCCTGCTGCTCATCCAGTCGTGGCTGG

AGCCCGTGCAGTTCCTCAGGAGTGTCTTCGCCAACAGCCTGGTGTACGGC

GCCTCTGACAGCAACGTCTATGACCTCCTAAAGGACCTAGAGGAAGGCAT

CCAAACGCTGATGGGGAGGCTGGAAGATGGCAGCCCCCGGACTGGGCAGA

TCTTCAAGCAGACCTACAGCAAGTTCGACACAAACTCACACAACGATGAC

GCACTACTCAAGAACTACGGGCTGCTCTACTGCTTCAGGAAGGACATGGA

CAAGGTCGAGACATTCCTGCGCATCGTGCAGTGCCGCTCTGTGGAGGGCA

GCTGTGGCTTC**GGCGGCCGCGGTGGCGGAGGTAGTGGTGGCGGAGGTAGC

GGTGGCGGAGGTTCTGGTGGCGGAGGTTCCGAATTC**

TTTTCTGGAAGTGAGGCCACAGCAGCTATCCTTAGCAGAGCACCCTGGAG

TCTGCAAAGTGTTAATCCAGGCCTAAAGACAAATTCTTCTAAGGAGCCTA

AATTCACCAAGTGCCGTTCACCTGAGCGAGAGACTTTTTCATGCCACTGG

ACAGATGAGGTTCATCATGGTACAAAGAACCTAGGACCCATACAGCTGTT

CTATACCAGAAGGAACACTCAAGAATGGACTCAAGAATGGAAAGAATGCC

CTGATTATGTTTCTGCTGGGGAAAACAGCTGTTACTTTAATTCATCGTTT

ACCTCCATCTGGATACCTTATTGTATCAAGCTAACTAGCAATGGTGGTAC

AGTGGATGAAAAGTGTTTCTCTGTTGATGAAATAGTGCAACCAGATCCAC

CCATTGCCCTCAACTGGACTTTACTGAACGTCAGTTTAACTGGGATTCAT
```

-continued

```
GCA:::::CAAGTGAGATGGGAAGCACCACGCAATGCAGATATTCAGA

AAGGATGGATGGTTCTGGAGTATGAACTTCAATACAAAGAAGTAAATGAA

ACTAAATGGAAAATGATGGACCCTATATTGACAACATCAGTTCCAGTGTA

CTCATTGAAAGTGGATAAGGAATATGAAGTaCGcGTGAGATCCAAACAAC

GAAACTCTGGAAATTATGGCGAGTTCAGTGAGGTGCTCTATGTAACACTT

CCTCAGATGAGCCAAAAGCTTTTCGAT:::::

CATCATCACCATCACCAT STOP
```

FIG. 2.2: EcoRV/AgeI Fragment (SEQ ID NO: 57)

```
::::::CAAGTGAGATGGGAAGCACCACGCAATGCAGATATTCAGAA

AGGATGGATGGTTCTGGAGTATGAACTTCAATACAAAGAAGTAAATG

AAACTAAATGGAAAATGATGGACCCTATATTGACAACATCAGTTCCA

GTGTACTCATTGAAAGTGGATAAGGAATATGAAGTaCGcGTGAGATC

CAAACAACGAAACTCTGGAAATTATGGCGAGTTCAGTGAGGTGCTCT

ATGTAACACTTCCTCAGATGAGCCAAAAGCTTTTCGAT:::::
```

FIG. 2.3: pGHsecTag-1B7v2 (SEQ ID NO: 58)
The EcoRV and AgeI sites are shown in red. Linker in bold. Hist tag underlined and in italics. STOP codon in large font

```
GCTAGCCACCATGGCTACAGGCTCCCGGACGTCCCTGCTCCTGGCTT

TTGGCCTGCTCTGCCTGCCCTGGCTTCAAGAGGGCAGTGCCTTCCCA

ACCATTCCCTTATCCAGGCTTTTTGACAACGCTATGCTCCGCGCCCA

TCGTCTGCACCAGCTGGCCTTTGACACCTACCAGGAGTTTGAAGAAG

CCTATATCCCAAAGGAACAGAAGTATTCATTCCTGCAGAACCCCCAG

ACCTCCCTCTGTTTCTCAGAGTCTATTCCGACACCCTCCAACAGGGA

GGAAACACAACAGAAATCCAACCTAGAGCTGCTCCGCATCTCCCTGC

TGCTCATCCAGTCGTGGCTGGAGCCCGTGCAGTTCCTCAGGAGTGTC

TTCGCCAACAGCCTGGTGTACGGCGCCTCTGACAGCAACGTCTATGA

CCTCCTAAAGGACCTAGAGGAAGGCATCCAAACGCTGATGGGAGGC

TGGAAGATGGCAGCCCCCGGACTGGGCAGATCTTCAAGCAGACCTAC

AGCAAGTTCGACACAAACTCACACAACGATGACGCACTACTCAAGAA

CTACGGGCTGCTCTACTGCTTCAGGAAGGACATGGACAAGGTCGAGA

CATTCCTGCGCATCGTGCAGTGCCGCTCTGTGGAGGGCAGCTGTGGC

TTCGGTGGCGGAGGTAGTGGTGGCGGAGGTAGCGGTGGCGGAGGTTC

TGGTGGCGGAGGTTCCGGTGGCGGAGGTAGTTTTTCTGGAAGTGAGG

CCACAGCAGCTATCCTTAGCAGAGCACCCTGGAGTCTGCAAAGTGTT

AATCCAGGCCTAAAGACAAATTCTTCTAAGGAGCCTAAATTCACCAA

GTGCCGTTCACCTGAGCGAGAGACTTTTTCATGCCACTGGACAGATG

AGGTTCATCATGGTACAAAGAACCTAGGACCCATACAGCTGTTCTAT

ACCAGAAGGAACACTCAAGAATGGACTCAAGAATGGAAAGAATGCCC

TGATTATGTTTCTGCTGGGGAAAACAGCTGTTACTTTAATTCATCGT

TTACCTCCATCTGGATACCTTATTGTATCAAGCTAACTAGCAATGGT
```

-continued

```
GGTACAGTGGATGAAAAGTGTTTCTCTGTTGATGAAATAGTGCAACC

AGATCCACCCATTGCCCTCAACTGGACTTTACTGAACGTCAGTTTAA

CTGGGATTCATGCAGATATCCAAGTGAGATGGGAAGCACCACGCAAT

GCAGATATTCAGAAAGGATGGATGGTTCTGGAGTATGAACTTCAATA

CAAAGAAGTAAATGAAACTAAATGGAAAATGATGGACCCTATATTGA

CAACATCAGTTCCAGTGTACTCATTGAAAGTGGATAAGGAATATGAA

GTGCGTGTGAGATCCAAACAACGAAACTCTGGAAATTATGGCGAGTT

CAGTGAGGTGCTCTATGTAACACTTCCTCAGATGAGCCAATAA AAG

CTT TTCGAATAAATCGAT::::: *CATCATCACCATCACCAT*

TGA
```

FIG. 2.4: pGHsecTag-1B7v2_Hist (SEQ ID NO: 59)

```
GCTAGCCCACCATGGCTACAGGCTCCCGGACGTCCCTGCTCCTGGCTT

TTGGCCTGCTCTGCCTGCCCTGGCTTCAAGAGGGCAGTGCCTTCCCAA

CCATTCCCTTATCCAGGCTTTTTGACAACGCTATGCTCCGCGCCCATC

GTCTGCACCAGCTGGCCTTTGACACCTACCAGGAGTTTGAAGAAGCCT

ATATCCCAAAGGAACAGAAGTATTCATTCCTGCAGAACCCCCAGACCT

CCCTCTGTTTCTCAGAGTCTATTCCGACACCCTCCAACAGGGAGGAAA

CACAACAGAAATCCAACCTAGAGCTGCTCCGCATCTCCCTGCTGCTCA

TCCAGTCGTGGCTGGAGCCCGTGCAGTTCCTCAGGAGTGTCTTCGCCA

ACAGCCTGGTGTACGGCGCCTCTGACAGCAACGTCTATGACCTCCTAA

AGGACCTAGAGGAAGGCATCCAAACGCTGATGGGGAGGCTGGAAGATG

GCAGCCCCCGGACTGGGCAGATCTTCAAGCAGACCTACAGCAAGTTCG

ACACAAACTCACACAACGATGACGCACTACTCAAGAACTACGGGCTGC

TCTACTGCTTCAGGAAGGACATGGACAAGGTCGAGACATTCCTGCGCA

TCGTGCAGTGCCGCTCTGTGGAGGGCAGCTGTGGCTTCGGTGGCGGAG

GTAGTGGTGGCGGAGGTAGCGGTGGCGGAGGTTCTGGTGGCGGAGGTT

CCGGTGGCGGAGGTAGTTTTTCTGGAAGTGAGGCCACAGCAGCTATCC

TTAGCAGAGCACCCTGGAGTCTGCAAAGTGTTAATCCAGGCCTAAAGA

CAAATTCTTCTAAGGAGCCTAAATTCACCAAGTGCCGTTCACCTGAGC

GAGAGACTTTTTCATGCCACTGGACAGATGAGGTTCATCATGGTACAA

AGAACCTAGGACCCATACAGCTGTTCTATACCAGAAGGAACACTCAAG

AATGGACTCAAGAATGGAAAGAATGCCCTGATTATGTTTCTGCTGGGG

AAAACAGCTGTTACTTTAATTCATCGTTTACCTCCATCTGGATACCTT

ATTGTATCAAGCTAACTAGCAATGGTGGTACAGTGGATGAAAAGTGTT

TCTCTGTTGATGAAATAGTGCAACCAGATCCACCCATTGCCCTCAACT

GGACTTTACTGAACGTCAGTTTAACTGGGATTCATGCAGATATCCAAG

TGAGATGGGAAGCACCACGCAATGCAGATATTCAGAAAGGATGGATGG

TTCTGGAGTATGAACTTCAATACAAAGAAGTAAATGAAACTAAATGGA

AAATGATGGACCCTATATTGACAACATCAGTTCCAGTGTACTCATTGA
```

-continued

```
AAGTGGATAAGGAATATGAAGTaCGcGTGAGATCCAAACAACGAAACT

CTGGAAATTATGGCGAGTTCAGTGAGGTGCTCTATGTAACACTTCCTC

AGATGAGCCAAAAGCTTTTCGATACCGGT CATCATCACCATCACCAT

░░░
```

Note: same reaction is performed for the construction of 1B7v3_Hist molecule

Stage 2: Construction of W104A GHR Mutation

Use as template pGHsecTag-1B7v2 Hist. After construction of the W104 mutation, the mutation can simply be transferred to other constructs (1B7v2 and GHBP_Hist) using AvrII/HindIII enzymes.

Method 1: PCR Based Method

Aim: The highlighted DNA (see sequence below) will be multiplied by PCR (polymerase Chain reaction) using DNA primers that include both AvrII, EcoRI and W104 mutations. The method produces 2 PCR fragements, both including the W104 mutation. Using overlapping PCR (i.e. both DNA fragments will anneal to each other due to overlapping sequences) we will produce a full length DNA insert with flanking AvrII and EcoRI sites. This can then be digested with both enzymes and ligated into the appropriate vector.

PCR Reactions and Primer Design:

Sequence showing GHR portion of 1B7 molecule: W104A mutation is underlined. AvrII and EcoRV site are shown in orange (SEQ ID NO: 60)

```
TTTTCTGGAAGTGAGGCCACAGCAGCTATCCTTAGCAGAGCACCCTGG

AGTCTGCAAAGTGTTAATCCAGGCCTAAAGACAAATTCTTCTAAGGAG

CCTAAATTCACCAAGTGCCGTTCACCTGAGCGAGAGACTTTTTCATGC

CACTGGACAGATGAGGTTCATCATGGTACAAAGAA░░░░░

ACCCATACAGCTGTTCTATACCAGAAGGAACACTCAAGAATGGACTCA

AGAATGGAAAGAATGCCCTGATTATGTTTCTGCTGGGGAAAACAGCTG

TTACTTTAATTCATCGTTTACCTCCATCGCAATACCTTATTGTATCAA

GCTAACTAGCAATGGTGGTACAGTGGATGAAAAGTGTTTCTCTGTTGA

TGAAATAGTGCAACCAGATCCACCCATTGCCCTCAACTGGACTTTACT

GAACGTCAGTTTAACTGGGATTCATGCA░░░░░ CAAGTGAGATGG

GAAGCACCACGCAATGCAGATATTCAGAAAGGATGGATGGTTCTGGAG

TATGAACTTCAATACAAAGAAGTAAATGAAACTAAATGGAAAATGATG

GACCCTATATTGACAACATCAGTTCCAGTGTACTCATTGAAAGTGGAT

AAGGAATATGAAGTaCGcGTGAGATCCAAACAACGAAACTCTGGAAAT

TATGGCGAGTTCAGTGAGGTGCTCTATGTAACACTTCCTCAGATGAGC

CAA TAA
```

Figure 37:
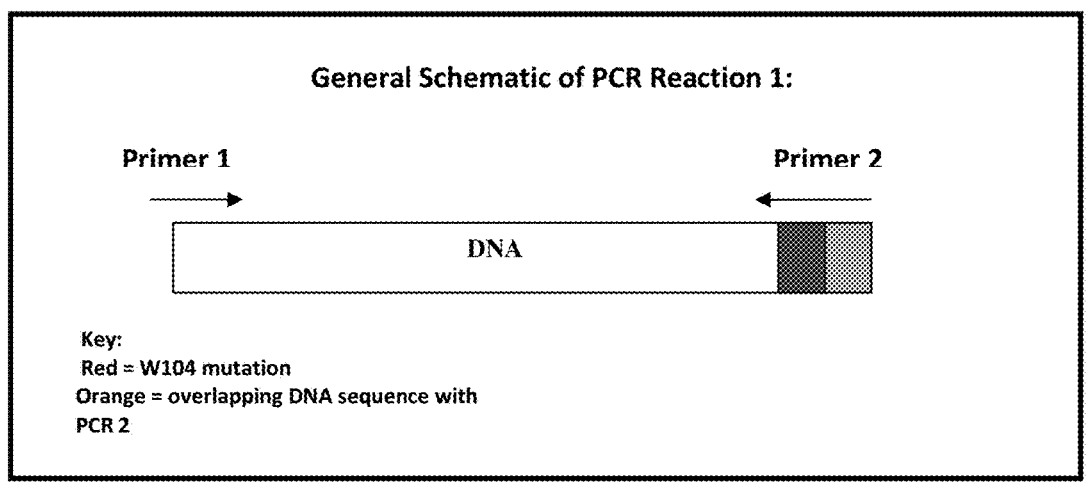
FIG. 37 illustrates the General Schematic of PCR Reaction 1, with primer 1 and primer 2.
Figure 38:
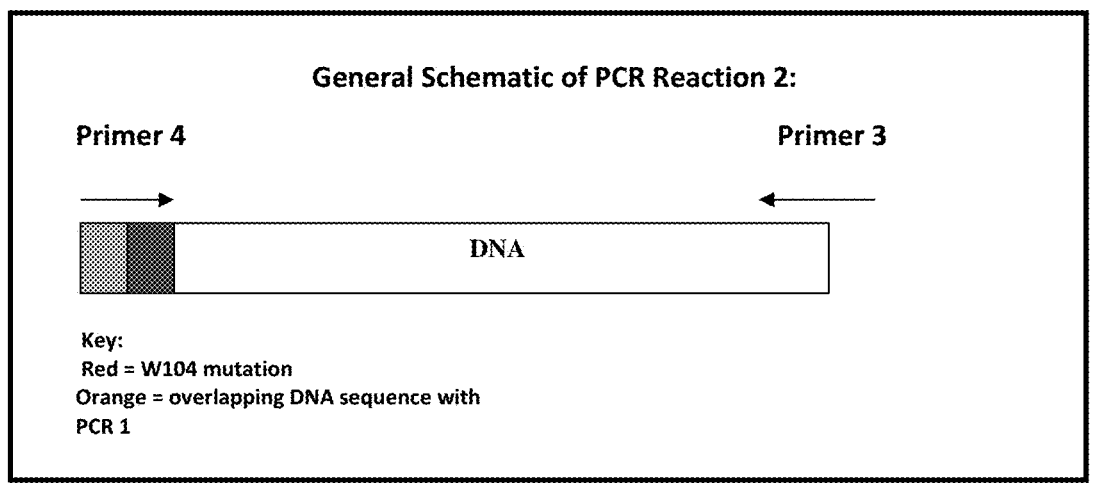
FIG. 38 illustrates the General Schematic of PCR Reaction 2, with primer 4 and primer 3.

PCR Reaction 1: (see FIG. 37)

Primer 1=GHR-AvrII: Forward primer: Binds 5' end of GHR and includes the endogenous restriction site AvrII (C>CTAGG). The AvrII site is shown underlined, GHR sequence is in italics (5'>3'). Tm=60 C. 28mer (SEQ ID NO: 61)
aaatttCCTAGG *ACCCATACAGCTGTTC*

Primer 2=GHR_W104rev: Reverse primer contains the W104 mutation (W>A, TGG>GCA). Also contains overlapping sequence to PCR reaction 2.

Tm for overhang=30 C, Tm for 3'end=58 C. 38mer (SEQ ID NO 62)
AATTCATCGTTTACCTCCATC [GCA] ATACCTTATTGT (SEQ ID NO: 63)
TTAAGTAGCAAATGGAGGTAG [CGT] TATGGAATAACA (SEQ ID NO: 64)
Flip: *ACAATAAGGTAT* [TGC] *GATGGAGGTAAACGATGAATT*

Primer 3=GHR_EcoRVrev. Reverse primer binds to the 3'end of GHR and includes the endogenous restriction site EcoRV. The EcoRV site is shown in square brackets. The GHR sequence is shown in italics. Tm=62 C 34mer (SEQ ID NO: 65)
CAGTTTAACTGGGATTCATGCA [GATATC]

(SEQ ID NO: 66)
GTCAAATTGACCCTAAGTACGT [CTATAG]

(SEQ ID NO: 67)
Flip: aaattt [GATATC] *TGCATGAATCCCAGTTAAACTG*

Primer 4:=GHR_W104for: Forward primer contains the W104 mutation (W>A, TGG>GCA)

Tm=60 C. Tm for overhang=26 C. 34mer (SEQ ID NO 68)
CCTCCATC [GCA] *ATACCTTATTGTATCAAGCTAAC*

Stage 3: Generation of PCR Fragments

PCR Reaction 1

Using expand enzyme system. Gel isolate PCR fragments on 1% agarose/TAE gel using Qiagen gel isolation kit.

Master Mix 1

|  | X1 |
|---|---|
| Template: 1B7v2 | 1 uL (100 ng) |
| GHR_AvrII (10 pmol/ul = 10 uM) | 1 ul |
| GHR_W104rev (10 pmol/ul = 10 uM) | 1 ul |
| dNTPs (10 mM) | 1.25 ul |
| Sterile water | 21.75 ul |

NB: Add template last to the reaction mix. Add water and dNTP first to prevent contamination by template. Do not take out MM2 material until MMI has been prepared to avoid cross contamination. Place MMI on ice until ready.

Master Mix 2:

|  | X1 |
|---|---|
| 10x polymerase buffer + MgCl2 (1.5 mM final) | 5 ul |
| Sterile water | 19.15. ul |
| Expand Polymerase | 0.85 ul |

Positive control; sample known to produce product under PCR conditions: GH template (GHstop template with GH1-23 and GH Hindrev primers). Negative controls are above reaction but no template. Mix 25 ul of MMI with 25 ul MMII and overlay with mineral oil.

Figure 39:
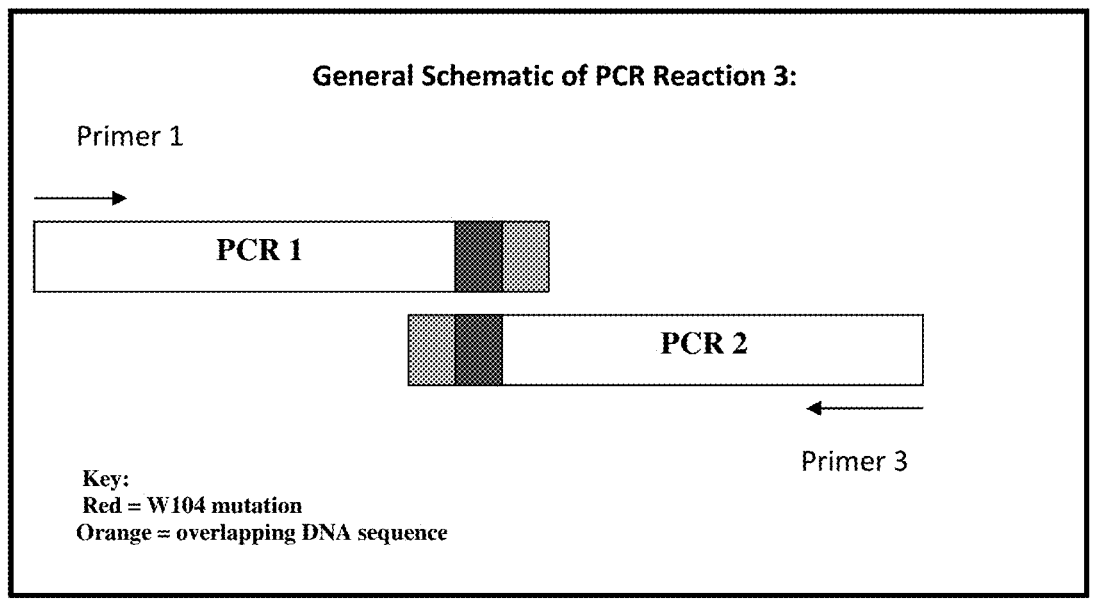
FIG. 39 illustrates the General Schematic of PCR Reaction 3, with primer 1 and primer 3.

PCR Reaction:
95 C for 2 min, [95 C for 30 sec; 54 C for 30 sec; 72 C for 30 sec] 25 cycles, 72 C for 10 min The above PCR reaction is repeated for PCR2 (replace with appropriate primers)
PCR Reaction 3 (See FIG. 39)

Overlapping PCR reaction. PCR fragments from reactions 1 and 2 are annealed and PCR amplified using appropriate forward and reverse primers that include the restriction enztme sites AvrII and EcoRI.
Master Mix 1

|  | X1 |
| --- | --- |
| PCR1 fragment (50 ng) | X ul |
| PCR2 fragment (50 ng) | X ul |
| GHR_Ayrll (10 pmol/ul = 10 uM) | 1 ul |
| GHR_EcoRV (10 pmol/ul = 10 uM) | 1 ul |
| dNTPs (10 mM stock) | 1.25 ul |
| Sterile water | X ul |
| Total Volume (ul) | 50 |

NB: Add template last to the reaction mix. Add water and dNTP first to prevent contamination by template. Do not take out MM2 material until MMI has been prepared to avoid cross contamination.
Master Mix 2:

|  | X1 |
| --- | --- |
| 10x polymerase buffer + MgCl2 (1.5 mM final) | 5 ul |
| Sterile water | 19.15. ul |
| Expand Polymerase | 0.85 ul |

PCR Reaction:

| Stage | Time | Temperature |
| --- | --- | --- |
| Denaturation | 2 min | 94 deg C. |
| 25 cycles @ | 30 s | 94 deg C. |
|  | 30 s | 54 deg C. |
|  | 30 s | 72 deg C. |
| Extension | 10 min | 72 deg C. |

Stage 4: Cloning of PCR Reaction 3
Digestion of PCR Reaction 3
Gel isolate PCR fragment on 1% agarose/TAE gel using Qiagen gel isolation kit. Restriction digest reaction will be set up as follows:

|  | volume | Stock concentration | Final concentration |
| --- | --- | --- | --- |
| PCR fragment | 25 ul | — | — |
| 10x buffer XX | 4 ul | 10x | 1x |
| Avrll | 2 ul | 10 U/ul | 20 U |
| EcoRV | 2 ul | 10 U/ul | 20 U |
| acBSA | 4 ul | 1 mg/ml | 100 ug/ml |
| Sterile water | 3 ul | — | — |

24 hours at 37 C. Isolate digested fragment and analyse digests by TAE/Agarose. Estimate concentration by agarose gel running against standards or use Nanodrop 260 nm.
Stage 5: Ligation of Sticky/Blunt Ends
Set up an initial ratio of plasmid to insert of 1:3 (molar) in a total volume of 10-15 ul Calculate amount of fragment to use as follows (Taken from Promega T4 DNA ligase data sheet)

$$\frac{ng\ vector \times kb\ size\ of\ insert}{Kb\ size\ of\ vector} \times \frac{molar\ ratio\ of\ insert}{vector} = ng\ of\ insert$$

|  | R1 | C1 | C2 |
| --- | --- | --- | --- |
| PCR fragment | X ul | — | — |
| pSecTag link, vector | X ul (~50-100 ng) | X ul | X ul |
| 10x ligase buffer | 1.5 ul | 1.5 ul | 1.5 ul |
| Sterile water | X ul | X ul | X ul |
| T4 DNA ligase | 1 ul | 1 ul | — |

Leave @ 37 C for 3 hours or o/n. Also set up reaction without ligase.
Stage 6: Transformation of Ligation:
Took 5 ul of above ligation and added to XL1-blue chemically competent cells. Leave for 30 minutes on ice, then heat shock @ 42 C. Leave on ice for a further 30 minutes. Plate out ligation mix onto freshly prepared agar plates containing 100 ug/ml Carbenicillin. Leave o/n 37 C.
Analysis of Clones:
Prepare plasmid from +ve clones and check authenticity by restriction digestion using Nhe1/HindIII (produces full length clone). These ligations produce the following constructs:
Stage 7: Verify Clones by PCR Screening and Sequencing:
A—Screening ligation clones by PCR using Taq Polymerase
Pick isolated single colony and streak into an agar grid plate, and then add remainder to 5 ul SDW as template.
Master Mix 1:
Add the 5 ul template last to the reaction mix:

|  | X1 |
| --- | --- |
| FP (10 pmol/ul = 10 uM) | 1 ul |
| RP (10 pmol/ul = 10 uM) | 1 ul |
| dNTPs (10 mM) | 1.25 ul |
| Sterile water | 16.75 ul |

Master Mix 2:

|  | X1 |
| --- | --- |
| 10x polymerase buffer + MgCl2 | 5 ul |
| Sterile water | 19.8 ul |
| Taq polymerase | 0.2 ul |

Negative control is reaction with above primers but no template.
PCR Reaction:
95 C for 2 min, [95 C for 30 sec; 52 C for 30 sec; 72 C for 30 sec] 35 cycles, 72 C for 10 min
Stage 8: Sequencing of Clones (Completed at Sheffield University):
Submit at least 2 clones for sequencing: send each plasmid in at least 10 ul @ 100 ng/ul (1 ug total) along with relevant primers @ 1 pmol/ul (send at least 10 ul)
Transient Cell Expression of 1B7v2 and 1B7v2 W104A
1. Use Trypsin-EDTA to remove CHO cells from a flask and resuspend in DMEM+10% FCS, 4 mM L-glutamine.

2. Seed @ 2×10E5 CHO cells into wells of a 24 well-plate, using 1 ml per well.
Remember to leave room for a non-transfected control. Leave o/n to attach.
3. The following day transfect using Fugene-6 (or Mirus) at a ratio of 3:2 to DNA i.e. add 4 microg DNA to 6 ul Fugene-6 in a volume of 100 ul serum free media. Briefly, warm Fugene-6 to RmT and premix by vortexing. Pippette 6 ul into 100 ul serum free media. Gently mix by flicking, add DNA, and again mix by flicking gently. Leave at RmT for 15 minutes. Pippette transfection mix into individual wells, swirl well contents to ensure even distribution. Do not allow Fugene-6 to come into contact with the plastic sides of the tubes being used.
4. Leave cells for 24 hrs and change media if required to serum free. Leave cells 48-72 hrs post treatment before harvesting media.
5. Product titre normally levels off after about 3-5 days.
6. Test expression using both Native and SDS-PAGE Stable Cell Expression A mammalian expression system has been established using a modified Invitrogen vector pSecTag-V5/FRT-Hist. This vector is used in Invitrogen's Flp-In system to direct integration of the target gene into the host cell line, allowing rapid generation of stable clones into specific sites within the host genome for high expression.

Culturing Flp-In Cell lines; followed manufactures instruction using basic cell culture techniques.

Stable cell lines were generated in 6-well plates using Fugene-6 as the transfection reagent. The CHO Flp-In cells were co-transfected with the expression vector and pOG44, a plasmid that expresses flp recombinase an enzyme which causes the recombination of the LR-fusion gene into a "hot-spot" of the cell chromosome. Hygromycin B was used to select for cells with positive recombinants.

Purification of GH-exGHR Fusions.

Human GH and GH receptor were amplified by RT-PCR from human pituitary and liver respectively and cloned into the vector, pSecTag-V5/FRT/Hist-TOPO (Invitrogen, Paisley, UK) under the human GH secretion signal sequence. Four repeats of a $Gly_4Ser$ linker were used to link the native C-terminus of human GH to the native N-terminus of the human GHR. Stable clones were made in CHO Flp-In cells (Invitrogen, Paisley, UK), adapted to protein free media and grown in suspension culture. LR-fusion expression was confirmed by an in-house ELISA. Affinity purification was performed using a GH mAb column.

Transcription Bioassays

These were performed as previously described in human 293 cells stably expressing the human GHR[16]. ELISA. An in house GH and fusion ELISA has been established based on the sandwich ELISA format. In the assay, standards (GH or fusion), controls and unknowns are incubated with biotin-labelled mouse antibody to human GH (mAb 7F8) in wells pre-coated with a mouse antibody to human GH antibody (mAb 10A7). The detection limit for the assay is 2.5 pg and the intra and inter assay CV is <10%. The IGF-I ELISA was purchased from DSL (DSL-10-2900 ACTIVE mouse/rat IGF-I kit; DSL Research Reagents, Oxfordshire, UK).

Nb2 Proliferation Assay

The ability of the Cell line Nb2 to proliferate in the presence of lactogen and assaying of endogenous dehydrogenase activity using the Celltitre Assay reagent (Promega) Non-Radioactive Proliferation Assay Reagents (Cat# G358C, Lot# 24464403, Ready to use One Solution Reagent: add 20 ul directly to media)

Basic Method
1. Take Nb2 cells and wash twice with ~20 ml of Assay media. Resuspend at 5.5×10E5 cells per ml in Assay media.
2. Grow cells o/n in T75 flasks to deplete the cells of lactogen @ 37 C, 5% CO2.
3. For the assay: Count cells and adjust density to ~2×10E4 cells in 50 ul (4×10E5 cells per ml) in Assay media. Plate on a 96 well plate (Require 100×50×(2×10E4)=2×10E6 cells)
4. Prepare a series of PRL standards as show in table below. Prepare sample and control dilutions as shown. Add 50 ul of each to allocated wells.
5. Grow cells in the presence of Standards and test samples for ~3 days @ 37C/5%CO2.
6. To Assay: Add 20 ul of CellTitre reagent (Promega CellTitre 96 Aqueous) and leave at 37 C for 2-6 hrs
7. Record the A490 nm reading of each well using a microplate reader.

Pharmacokinetic Studies

Seven week old normal Sprague Dawley rats from Janvier (Le Genest Saint Isle, France) were used for pharmacokinetic studies. Sc or iv administration (penile vein) and blood withdrawal (orbital sinus) were conducted under isoflurane anaesthesia. The rats (n=4-6/group) were injected iv or sc with of 0.1 mg/kg rhGH or fusion. Blood samples were collected from the retro-orbital plexus. Serum was harvested and stored at −70° C. until assays. Pharmacokinetic parameters were estimated by fitting values of hormone concentration versus time to compartmental models using non-linear least-squares regression analysis. Clearance values were normalized to animal weight. Clearance rate per animal weight and terminal half lives ($t_{1/2}$) were calculated using the coefficient and exponents obtained from the iv bolus model fits.

Primate Pharmacokinetic Study

The test substances were formulated in solutions containing 11.9 mM sodium and potassium phosphates, 137 mM sodium chloride, 2.7 mM potassium chloride, 0.01% polysorbate 80; pH of the solution was adjusted to 7.4.

Blood samples were obtained from all animals throughout the study in order to determine the concentration of the appropriate test material in serum. These samples were taken at a number of time points throughout the study.

Clinical Endpoints and Measurements

The serum concentration of IB7v2 and IB7v3 was determined using a validated ELISA method. The pharmacokinetic profile for each of the protein was determined by plotting the concentration for each of the protein in serum versus time using WinNonlin Pro (v4.0.1) software.

Growth Studies

The growth studies used hypophysectomized rats and were performed on Sprague Dawley rats from Charles River Laboratories (Larbresle, France). Rats were hypophysectomized under isoflurane anaesthesia at 4 weeks of age by the breeder and delivered one week after selection on body weight criteria for successful surgery. Animals were individually caged and allowed another week of rest before entering the experimental phase. The injection solutions of excipient, rhGH and fusion never exceeded 2 ml/kg. The rats were weighed daily and depending on the administration protocol, received injections of the test substances for 10 days.

Characterisation of Growth Hormone Fusions

Conformation of the fusion protein was examined using a panel of 16 conformationally sensitive hGH receptor mAbs. Denaturing, native gels and western blotting were used to analyse the LR-fusion and western blotting performed with non-conformationally sensitive to GH. The form of the LR-fusion protein in solution was defined by gel filtration using a Superose G200 analytical column and analytical ultracentrifugation. Analytical ultracentrifugation (AUC) was performed by sedimentation velocity (Analytical service, Dr Andy Barry, Astbury, Leeds University, Leeds, UK).

Statistics

Two groups were compared with a Student's test if their variance was normally distributed or by a Student-Satterthwaite's test if not normally distributed. Distribution was tested with an F test. One-way ANOVA was used to compare the means of 3 or more groups and if the level of significance was p<0.05 individual comparisons were performed with Dunnett's tests. All statistical tests were two-sided at the 5% level of significance and no imputation was made for missing values.

Example 1

GHwt as expected shows comparable activity to rhGH; 1B7v2_wt shows lower activity than rhGH at equivalent concentrations (usually 10-20 fold less). However, the mutant 1B7v2_W104A mutant shows increased activity at all concentrations studied. This may imply that the presence of the W104A mutation which prevents dimerisation of the 1B7v2 molecule, increases its activity by increasing the bioavailability of monomeric 1B7v2.

Example 2

The Nb2 cell line shows a greater level of proliferation in the presence of the 1B7v2_W104A mutant when compared to 1B7v2_wt. The growth curve for 1B7v2_W104A is shifted closer to rhGH. This may imply that the presence of the W104A mutation which prevents dimerisation of the 1B7v2 molecule, increases its activity by increasing the bioavailability of monomeric 1B7v2.

References

1. Woodhouse, L. J., Mukherjee, A., Shalet, S. M. & Ezzat, S. The influence of growth hormone status on physical impairments, functional limitations, and health-related quality of life in adults. Endocr Rev. 27, 287317 (2006).
2. Clark, R. et al. Long-acting growth hormones produced by conjugation with polyethylene glycol. Journal of Biological Chemistry. 271, 2196921977 (1996).
3. Cook, D. M. et al. The pharmacokinetic and pharmacodynamic characteristics of a long-acting growth hormone (GH) preparation (nutropin depot) in GH-deficient adults. J Clin Endocrinol Metab. 87, 450814 (2002).
4. Reiter, E. O. et al. A multicenter study of the efficacy and safety of sustained release GH in the treatment of naive pediatric patients with GH deficiency. J Clin Endocrinol Metab. 86, 47006 (2001).
5. Jostel, A., Mukherjee, A., Alenfall, J., Smethurst, L. & Shalet, S. M. A new sustained-release preparation of human growth hormone and its pharmacokinetic, pharmacodynamic and safety profile. Clin Endocrinol (Oxf). 62, 6237 (2005).
6. Laursen, T. et al. Long-term effects of continuous subcutaneous infusion versus daily subcutaneous injections of growth hormone (GH) on the insulin-like growth factor system, insulin sensitivity, body composition, and bone and lipoprotein metabolism in GH-deficient adults. J Clin Endocrinol Metab. 86, 12228 (2001).
7. Laursen, T., Jorgensen, J. O., Jakobsen, G., Hansen, B. L. & Christiansen, J. S. Continuous infusion versus daily injections of growth hormone (GH) for 4 weeks in GH-deficient patients. J Clin Endocrinol Metab. 80, 24108 (1995).
8. Muller-Newen, G., Kohne, C. & Heinrich, P. C. Soluble receptors for cytokines and growth factors. [Review] [58 refs]. International Archives of Allergy & Immunology. 111, 99106 (1996).
9. Baumann, G., Amburn, K. D. & Buchanan, T. A. The effect of circulating growth hormone-binding protein on metabolic clearance, distribution, and degradation of human growth hormone. J Clin Endocrinol Metab. 64, 65760 (1987).
10. Baumann, G. Growth hormone heterogeneity: genes, isohormones, variants, and binding proteins. Endocrine Reviews 12, 424449 (1991).
11. Baumann, G., Shaw, M. A. & Buchanan, T. A. In vivo kinetics of a covalent growth hormone-binding protein complex. Metabolism. 38, 3303 (1989).
12. Clark, R. G. et al. Recombinant human growth hormone (GH)-binding protein enhances the growth-promoting activity of human GH in the rat. Endocrinology. 137, 43084315 (1996).
13. Baumann, G. Growth hormone binding protein--errant receptor or active player? [editorial]. Endocrinology. 136, 377378 (1995).
14. Ayling, R. M. et al. A dominant-negative mutation of the growth hormone receptor causes familial short stature. Nature Genetics. 16, 1314 (1997).
15. Ross, R. J. et al. A short isoform of the human growth hormone receptor functions as a dominant negative inhibitor of the full-length receptor and generates large amounts of binding protein. Molecular Endocrinology. 11, 265273 (1997).
16. Ross, R. J. M. et al. Binding and functional studies with the growth hormone receptor antagonist, B2036-PEG (pegvisomant), reveal effects of pegylation and evidence that it binds to a receptor dimer. Journal of Clinical Endocrinology & Metabolism. 86, 17161723 (2001).
17. Cunningham, B. C. et al. Dimerization of the extracellular domain of the human growth hormone receptor by a single hormone molecule. Science. 254, 821825 (1991).
18. Huston, J. S., Tai, M. S., McCartney, J., Keck, P. & Oppermann, H. Antigen recognition and targeted delivery by the single-chain Fv. Cell Biophys. 22, 189-224 (1993).
19. Herington, A. C., Smith, A. I., Wallace, C. & Stevenson, J. L. Partial purification from human serum of a specific binding protein for human growth hormone. Mol Cell Endocrinol. 53, 2039 (1987).
20. Frick, G. P., Tai, L. R., Baumbach, W. R. & Goodman, H. M. Tissue distribution, turnover, and glycosylation of the long and short growth hormone receptor isoforms in rat tissues. Endocrinology. 139, 282430 (1998).
21. Mannor, D. A., Winer, L. M., Shaw, M. A. & Baumann, G. Plasma growth hormone (GH)-binding proteins: effect on GH binding to receptors and GH action. J Clin Endocrinol Metab. 73, 304 (1991).
22. Lim, L., Spencer, S. A., McKay, P. & Waters, M. J. Regulation of growth hormone (GH) bioactivity by a recombinant human GH-binding protein. Endocrinology. 127, 128791 (1990).

23. Haffner, D., Schaefer, F., Girard, J., Ritz, E. & Mehls, O. Metabolic clearance of recombinant human growth hormone in health and chronic renal failure. J Clin Invest. 93, 116371 (1994).
24. Johnson, V. & Maack, T. Renal extraction, filtration, absorption, and catabolism of growth hormone. American Journal of Physiology 233, F185F196 (1977).
25. Veldhuis, J. D. et al. Impact of experimental blockade of peripheral growth hormone (GH) receptors on the kinetics of endogenous and exogenous GH removal in healthy women and men. Journal of Clinical Endocrinology & Metabolism 87, 57375745 (2002).
26. Osborn, B. L. et al. Albutropin: a growth hormone-albumin fusion with improved pharmacokinetics and pharmacodynamics in rats and monkeys. Eur J Pharmacol 456, 14958 (2002).
27. de Vos, A. M., Ultsch, M. & Kossiakoff, A. A. Human growth hormone and extracellular domain of its receptor: crystal structure of the complex. Science 255, 306312 (1992).

We claim:

1. A fusion protein agonist comprising:

a growth hormone polypeptide as set forth in SEQ ID NO: 70, wherein the polypeptide is linked either directly or indirectly to a polypeptide comprising the amino acid sequence of a growth hormone receptor polypeptide as set forth in SEQ ID NO: 69, wherein said receptor polypeptide is modified by deletion or substitution of tryptophan 104.

2. The fusion protein agonist according to claim 1, wherein said receptor polypeptide is modified by substitution at amino acid residue tryptophan 104.

3. The fusion protein agonist according to claim 2, wherein the tryptophan 104 is substituted with alanine.

4. The fusion protein agonist according to claim 1 wherein said growth hormone polypeptide is linked to said receptor polypeptide by a peptide linker.

5. The fusion protein agonist according to claim 4 wherein said peptide linking molecule comprises at least one copy of the peptide Gly Gly Gly Gly Ser [SEQ ID NO: 55].

6. The fusion protein agonist according to claim 5 wherein said peptide linking molecule comprises 2, 3, 4, 5, 6 or 7 copies of the peptide Gly Gly Gly Gly Ser [SEQ ID NO: 55].

7. The fusion protein agonist according to claim 1 wherein said protein comprises or consists of an amino acid sequence as set forth in SEQ ID NO: 4 or SEQ ID NO: 71.

8. The fusion protein agonist according to claim 1 wherein said protein comprises or consists of an amino acid sequence as set forth in SEQ ID NO: 5 or SEQ ID NO: 72.

9. The fusion protein agonist according to claim 1 wherein said protein comprises or consists of an amino acid sequence as set forth in SEQ ID NO: 6 or SEQ ID NO: 73.

10. A nucleic acid molecule that encodes a fusion protein according to claim 1.

11. A vector comprising a nucleic acid molecule according to claim 10.

12. A cell transfected or transformed with a vector according to claim 11.

13. A pharmaceutical composition comprising the fusion protein agonist according to claim 1 including an excipient or carrier.

14. A method to treat a human subject suffering from growth hormone deficiency comprising administering an effective amount of a fusion protein according to claim 1.

15. The method according to claim 14 wherein said growth hormone deficiency is childhood growth hormone deficiency.

16. The method according to claim 14 wherein said growth hormone deficiency is adult growth hormone deficiency.

* * * * *